US009873882B2

(12) United States Patent
Meulewaeter et al.

(10) Patent No.: US 9,873,882 B2
(45) Date of Patent: Jan. 23, 2018

(54) ENHANCED SELECTIVE EXPRESSION OF TRANSGENES IN FIBER PRODUCING PLANTS

(71) Applicants: Bayer CropScience NV, Diegem (BE); Texas Tech University, Lubbock, TX (US)

(72) Inventors: Frank Meulewaeter, Merelbeke (BE); Zhixin Xie, Lubbock, TX (US); Gengxiang Jia, Lubbock, TX (US); Arnab Ghosh, Lubbock, TX (US); Forrest Sheng Bao, Akron, OH (US)

(73) Assignees: Bayer CropScience NV, Diegem (BE); Texas Tech University, Lubbock, TX (US)

( * ) Notice: Subject to any disclaimer, the term of this patent is extended or adjusted under 35 U.S.C. 154(b) by 12 days.

(21) Appl. No.: 14/890,191

(22) PCT Filed: May 13, 2014

(86) PCT No.: PCT/EP2014/059778
§ 371 (c)(1),
(2) Date: Nov. 10, 2015

(87) PCT Pub. No.: WO2014/184196
PCT Pub. Date: Nov. 20, 2014

(65) Prior Publication Data
US 2016/0108413 A1    Apr. 21, 2016

Related U.S. Application Data

(60) Provisional application No. 61/823,297, filed on May 14, 2013.

(51) Int. Cl.
| | | |
|---|---|---|
| C12N 15/82 | (2006.01) | |
| A01H 5/00 | (2006.01) | |
| A01H 5/10 | (2006.01) | |
| C12N 9/10 | (2006.01) | |

(52) U.S. Cl.
CPC ........... *C12N 15/8218* (2013.01); *A01H 5/10* (2013.01); *C12N 9/1051* (2013.01); *C12N 15/8216* (2013.01); *C12N 15/8261* (2013.01)

(58) Field of Classification Search
None
See application file for complete search history.

(56) References Cited

U.S. PATENT DOCUMENTS

| | | | |
|---|---|---|---|
| 5,004,863 A | 4/1991 | Umbeck | |
| 5,792,933 A | 8/1998 | Ma | |
| 6,166,294 A | 12/2000 | Kasukabe et al. | |
| 6,259,003 B1 | 7/2001 | Fujisawa et al. | |
| 6,483,013 B1 | 11/2002 | Reynaerts et al. | |
| 8,314,290 B2 * | 11/2012 | Allen | C12N 15/8216 435/419 |
| 2003/0106097 A1 | 6/2003 | Pirola et al. | |
| 2013/0081154 A1 | 3/2013 | Meulewaeter et al. | |

FOREIGN PATENT DOCUMENTS

| | | |
|---|---|---|
| EP | 1339859 B1 | 12/2001 |
| WO | 92/15675 | 9/1992 |
| WO | 98/00549 | 1/1998 |
| WO | 98/30698 | 7/1998 |
| WO | 00/71733 | 11/2000 |
| WO | 02/10377 | 2/2002 |
| WO | 02/10413 | 2/2002 |
| WO | 02/45485 | 6/2002 |
| WO | 2005/017157 A1 | 2/2005 |
| WO | 2006/111512 A1 | 10/2006 |
| WO | 2006/136351 A2 | 12/2006 |
| WO | 2006/138638 A1 | 12/2006 |
| WO | 2007/039454 A1 | 4/2007 |
| WO | 2007/047016 A2 | 4/2007 |
| WO | 2008/012058 A1 | 1/2008 |
| WO | 2008/083969 A2 | 7/2008 |
| WO | 2008/133643 A2 | 11/2008 |
| WO | 2009/003078 A2 | 12/2008 |
| WO | 2010/042575 A1 | 4/2010 |
| WO | 2011/089021 A1 | 7/2011 |
| WO | 2012/048807 A1 | 4/2012 |
| WO | 2012/093032 A1 | 7/2012 |

OTHER PUBLICATIONS

Kwak et al, 2009, BMC Genomics, 10:1-11.*
Sunkar et al, 2006, The Plant Cell, 18:2051-2065.*
Kwak et al, 2009, BMC, 10:1-11.*
Allen, Edwards, et al., microRNA-Directed Phasing during Trans-Acting siRNA Biogenesis in Plants, Cell, Apr. 22, 2005, vol. 121, pp. 207-221.
Cuperus, Josh T., et al., Evolution and Functional Diversification of MIRNA Genes, The Plant Cell, Feb. 2011, vol. 23, pp. 431-442.
Graves, D.A., et al., Chronology of the differentiation of cotton (*Gossypium hirsutum* L.) fiber cells, Planta, 1988, vol. 175, pp. 254-258.
Harvey, Jagger J.W., et al., An Antiviral Defense Role of AGO2 in Plants, 2011, PLoS One, 6: e14639.
Hayashi, Takahisa, et al., Xyloglucan in the cell walls of cotton fiber, Carbohydrate Research, 1988, vol. 181 pp. 273-277.
Huwyler, H.R., et al., Changes in the Composition of Cotton Fibre Cell Walls during Development, Planta, 1979, vol. 146, pp. 635-642.
Jaubert, Marianne, et al., Argonaute2 Mediates RNA-Silencing Antiviral Defenses against Potato virus X in *Arabidopsis*1, Plant Physiology, Jul. 2011, vol. 156, pp. 1556-1564.
Johansen, Lisa K., et al., Silencing on the Spot. Induction and Suppression of RNA Silencing in the Agrobacterium-Mediated Transient Expression System, Plant Physiol., 2001, vol. 126, pp. 930-938.

(Continued)

*Primary Examiner* — Jason Deveau Rosen

(57) ABSTRACT

Methods and means are provided to enhance the selective expression of transgenes under control of a fiber-selective promoter, in fiber cells, particularly cotton fiber cells by including target sites for naturally occurring microRNAs with a specific expression profile, particularly with a differential expression profile between cells leading to fibers and other cells of the fiber producing plant, into the transcribed region of genes of interest.

15 Claims, 7 Drawing Sheets

(56) References Cited

OTHER PUBLICATIONS

Jones-Rhoades, Matthew W., et al., MicroRNAs and Their Regulatory Roles in Plants, 2006, Annual Rev. Plant Biol., vol. 57, pp. 19-53.
Kasschau, Kristin D., et al., P1/HC-Pro, a Viral Suppressor of RNA Silencing, Interferes with *Arabidopsis* Development and miRNA Function, Developmental Cell, Feb. 2003, vol. 4, pp. 205-217.
Kim, Hee Jin, et al., Cotton Fiber Growth in Planta and in Vitro. Models for Plant Cell Elongation and Cell Wall Biogenesis, Plant Physiology, Dec. 2001, vol. 127, pp. 1361-1366.
Kwak, Pieter Bas, et al., Enrichment of a set of microRNAs during the cotton fiber development, BMC Genomics, 2009, vol. 10, pp. 457.
Mallory, Allison, et al., Form, Function, and Regulation of Argonaute Proteins, The Plant Cell, Dec. 2010, vol. 22, pp. 3879-3889.
Meinert, Maureen C., et al., Changes in Biochemical Composition of the Cell Wail of the Cotton Fiber During Development, Plant Physiol., 1977, vol. 59, pp. 1088-1097.
Pang, Mingxiong, et al., Genome-wide analysis reveals rapid and dynamic changes in miRNA and siRNA sequence and expression during ovule and fiber development in allotetraploid cotton (*Gossypium hirsutum* L.), Genome Biology 2009, vol. 10, R122.
Peng, Liangcai, et al., Sitosterol-b-glucoside as Primer for Cellulose Synthesis in Plants, Science, Jan. 2002, vol. 295, pp. 147-150.
Pfluger, Jennifer, et al., Cell growth: The power of symplastic isolation, 2001, Current Biology 11: R436-R439.
Qi, Xiaopeng, et al., Small RNA Deep Sequencing Reveals Role for *Arabidopsis thaliana* RNA-Dependent RNA Polymerases in Viral siRNA Biogenesis, 2009, PLoS One, 4: e4971.
Ruan, Yong-Ling Ruan, et al., A Fiberless Seed Mutation in Cotton Is Associated with Lack of Fiber Cell Initiation in Ovule Epidermis and Alterations in Sucrose Synthase Expression and Carbon Partitioning in Developing Seeds1, Plant Physiol., 1998, vol. 118, pp. 399-406.

Ruan, Yong-Ling, et al., Pathway and control of sucrose import into initiating cotton fibre cells, Aust. J. Plant Physiol., 2000, vol. 27, pp. 795-800.
Valoczi, Anna, et al., Sensitive and specific detection of microRNAs by northern blot analysis using LNA-modified oligonucleotide probes, Nucleic Acids Research, 2004, vol. 32, No. 22, e175.
Van't Hof, Jack, Increased Nuclear DNA Content in Developing Cotton Fiber Cells, American Journal of Botany, 1999, vol. 86(6), pp. 776-779.
Vaucheret, Herve, Plant Argonautes, Trends in Plant Science, 2008, vol. 13, No. 7.
Wang, Xian-Bing, et al., The 21-Nucleotide, but Not 22-Nucleotide, Viral Secondary Small Interfering RNAs Direct Potent Antiviral Defense by Two Cooperative Argonautes in *Arabidopsis thaliana*, The Plant Cell, Apr. 2011, vol. 23, pp. 1625-1638.
Wang, Zheng-Ming, et al., A Comparative miRNAome Analysis Reveals Seven Fiber Initiation-Related and 36 Novel miRNAs in Developing Cotton Ovules, Molecular Plant, Jul. 2012, vol. 5, No. 4, pp. 889-900.
Xiang, Chengbin, et al., A mini binary vector series for plant transformation, Plant Molecular Biology, 1999, vol. 40, pp. 711-717.
Xie, Zhixin, et al., Dicer-Like 4 functions in trans-acting small interfering RNA biogenesis and vegetative phase change in *Arabidopsis thaliana*, PNAS USA, 2005, vol. 102, pp. 12984-12989.
Xie, Zhixin, et al., Expression of *Arabidopsis* MIRNA Genes1[w], Plant Physiology, Aug. 2005, vol. 138, pp. 2145-2154.
Xiong, Liming, et al., High Throughput Screening of Signal Transduction MutantsWith Luciferase Imaging, Plant Molecular Biology Reporter, 1999, vol. 17, pp. 159-170.
International Search Report for PCT Application No. PCT/EP2014/059778, Nov. 20, 2014.
Basra, Amarjit S., et al., Development of the Cotton Fiber, 1984, Int Rev of Cytology, vol. 89, pp. 65-113.
Ruan, Yong-Ling, et al., The Control of Single-Celled Cotton Fiber Elongation by Developmentally Reversible Gating of Plasmodesmata and Coordinated Expression of Sucrose and K + Transporters and Expansin, The Plant Cell, Jan. 2001, vol. 13, pp. 47-60.

* cited by examiner

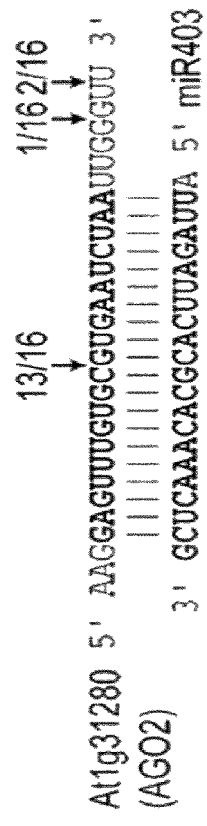

■ miR403 in *Arabidopsis thaliana* and *Gossypium hirsutum*

>Ghi_miR403 TTAGATTCACGCACAAACTCG
>Ath_miR403 TTAGATTCACGCACAAACTCG

■ miR403-interacting site in *Arabidopsis* AGO2 (At1g31280) mRNA

At1g31280   5' AAGGAGUUUGUGGCGUGAAUCUAA<u>UUGGGUU</u> 3'
(AGO2)            |||||||||||||||||||||||
            3'    GCUCAAACACGCACUUAGAUUA 5' miR403

13/16 ↑    1/16 2/16 ↑↑

■ miR403 target sequence for engineered REPORTER

>Ath_miR403 target 5'-AAGGGAGTTTGTGCGTGAATCTAATTG-3'
>Ath_miR403_R      3'-----GCTCAAACACGCACTTAGATTa----5'
>Ghi_miR403_R      3'-----GCTCAAACACGCACTTAGATT-----5'

Figure 3

1. Ghi_miR408 in FM958 (major & minor forms detected)

```
>ghi-miR408.1       5'-AUGCACUGCCUCUUCCCUGGC_-3'
>ghi-miR408.2        5'_UGCACUGCCUCUUCCCUGGCU-3'
```

2. Proposed artificial miR408 target sequence
(To be engineered into the 3'UTR of the transgene of choice)

```
>miR408_Target   5'-gacGCCGGTGAAGAGGCAGTGCAAgac-3'
                       ...°.x.............x
>ath_miR408_R       3'-CGGTCCCTTCTCCGTCACGTA-5'
```

Figure 4

```
Ghi_miRcan1230 (1)   5'-.   aguUUUAAAGUAGUGCCAUGCAUUuuu.-3'    A.
                            ||||||||||||||||  ||||||
                     3'-UAAAAUUUCAUCACAGUACGUU-5'

Ghi_miRcan1230 (2)   5'-..aguUUUAAAGUAGUGCCAUGCAUUuuu.-3'
                            ||||||||||||||||  ||||||
                     3'-AAAAUUUCAUCACAGUACGUUU-5'

Ghi_miRcan1230 (3)   5'-.  agaGUAGUGUCAUGCAAAGCCAGCAaug.-3'
                           |||||||||||||||||||  ||
                     3'-CAUCACAGUACGUUUCGGU-GU-5'

Ghi_miR398           5'-...gccATTGGGCGACCTGGGAACACTaga...-3'    B.
                           ||||||||||||  |||||
                     3'-GUCCCCGCUGGACUCUUGUGU-5'
```

Figure 5

ENHANCED SELECTIVE EXPRESSION OF TRANSGENES IN FIBER PRODUCING PLANTS

CROSS-REFERENCE TO RELATED APPLICATIONS

This application is a §371 U.S. National Stage of International Application No. PCT/EP14/059778 filed May 13, 2014, which claims the benefit of the U.S. Patent Application Ser. No. 61/823,297, filed May 14, 2013, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "BCS13-2006.ST25," created on Nov. 10, 2015, and having a size of 142 kilobytes and is filed concurrently with the specification. The sequence listing contained in this ASCII formatted document is part of the specification and is herein incorporated by reference in its entirety.

FIELD OF THE INVENTION

This invention relates to the field of agricultural biotechnology, more specifically to the use of molecular biology techniques to alter the expression pattern of transgenes in fiber-producing plants such as cotton. Naturally occurring microRNAs with a specific expression profile, particularly with a differential expression profile between cells leading to fibers and other cells of the fiber producing plant, are provided. By engineering and including target sites for such microRNAs in genes, particularly in transgenes, the expression profile of the gene comprising such microRNA target site will reflect (mirror) the expression profile of the microRNA in plants. Such microRNAs and the corresponding target sites can be used to enhance the selective expression of transgenes under control of a fiber-selective promoter, in fibers, particularly cotton fibers.

BACKGROUND OF THE INVENTION

Cotton (*Gossypium* spp.) is the world's most important natural textile fiber and is also a significant oilseed crop. Cotton production provides income for approximately 100 million families, and approximately 150 countries are involved in cotton import and export. Its economic impact is estimated to be approximately $500 billion/year worldwide. World consumption of cotton fiber is approximately 115 million bales or approximately 27 million metric tons per year (National Cotton Council, on the world wide web at cotton.org, 2006). The genus *Gossypium* is relatively complex and includes approximately 45 diploid (2n=2x=26) and five tetraploid (2n=4x=52) species, all exhibiting disomic patterns of inheritance. Diploid species (2n=26) fall into eight genomic groups (A-G, and K). The African Glade, comprising the A, B, E, and F genomes, occurs naturally in Africa and Asia, while the D genome Glade is indigenous to the Americas. A third diploid Glade, including C, G, and K, is found in Australia. All 52 chromosome species, including *Gossypium hirsutum* and *Gossypium barbadense*, are classic natural allotetraploids that arose in the New World from interspecific hybridization between an A genome-like ancestral African species and a D genome-like American species. The closest extant relatives of the original tetraploid progenitors are the A genome species *Gossypium herbaceum* (A1) and *Gossypium arboreum* (A2) and the D genome species *Gossypium raimondii* (D5) 'Ulbrich'. Polyploidization is estimated to have occurred 1 to 2 million years ago, giving rise to five extant allotetraploid species. Interestingly, the A genome species produce spinnable fiber and are cultivated on a limited scale, whereas the D genome species do not. More than 95% of the annual cotton crop worldwide is *G. hirsutum*, Upland or American cotton, and the extra-long staple or Pima cotton (*G. barbadense*) accounts for less than 2% (National Cotton Council, on the world wide web at cotton.org, 2006).

Each cotton fiber is a differentiated single epidermal cell of the ovule. Approximately half a million fibers are produced per cotton boll, some forming fuzz and some forming lint. Initiation of an epidermal cell into fiber requires a change in cell fate, which is a fundamental biological process involving genetic, physiological and developmental "switches". Genetic mutations, polyploidy, pollination/fertilization, and hormonal regulation can affect the number of cells developing into fibers or alter fiber cell properties (fuzz vs. lint). However, it is unclear how these factors control gene expression changes that orchestrate the pattern and tempo in early stages of fiber development.

In contrast, the morphological development of cotton fibers is well documented in the art. Cotton fibers undergo four overlapping developmental stages: fiber cell initiation, elongation, secondary wall biosynthesis, and maturation. Fiber initiation is a rapid process. The white fluffy fibers begin to develop immediately after anthesis and continue up to 3 days post-anthesis (DPA), which is followed by fiber cell elongation (until 20 DPA). Secondary wall biosynthesis initiates around 15 dpa and continues to 45 DPA, followed by a maturation process at 45-60 DPA. Cotton fibers are derived from ovular epidermal cells (maternal tissues). However, only ~25-30% of the epidermal cells differentiate into the commercially important lint fibers. The majority of cells does not differentiate into fibers or develop into short fibers or fuzz. For the cells committed to fiber development, cell initiation and elongation are nearly synchronous on each ovule, indicating that changes in gene expression are orchestrated during fiber differentiation and development through intercellular signaling and/or timing mechanisms.

In many instances, it may be advantageous to preferentially, selectively or specifically express genes in fiber developing cells or fibers. Such expression can influence the fiber development and result in longer or stronger fibers. WO 98/00549 describes the expression of cellulose synthase gene in fiber-developing cells. WO 08/012058 and WO02/45485 describe expression of sucrose synthase genes in cotton fiber developing cells. WO05/017157 describes reduction of the expression of β-1,3-glucanase in fiber-developing cells.

Cotton fiber consists of cellulose, a natural polymer composed of many molecules of the sugar glucose. Its unique structure is ideally suited for textile production. Each fiber is basically a hollow tube a few centimeters in length that, when spun and woven, provides the very special characteristic "feel" of cotton. Natural cellulose containing fibers, however, do not possess the chemical versatility of synthetic fibers, due to the relative inert nature of the cellulose consisting of β-1-4 linked glucose monomers.

WO06/136351, WO11/089021 and WO12/048807 all describe methods and means for altering cell wall reactivity in fibers of fiber producing plants such as cotton, by inclusion of positively charged oligosaccharides or polysaccharides into the cell wall. To this end, N-acetylglucosamine transferases, including chitin synthases, are expressed in fibers of the plants, and optionally also glutamine:fructose-6-phosphate amidotransferase. Although, chitin could be efficiently produced in cotton plant cell walls, it was also observed that the transgenic plants usually exhibited some reduced growth which may be attributed to a negative effect of the expression of the transgene in cotton outside of the cotton fibers.

It would thus be advantageous to be able to increase the tissue-selectivity of the expression of transgenes in fiber-producing plants, in particular to be able to increase the selectivity of expression in fibers and/or fiber-developing cells, while expression in other cells of the fiber-producing plant is substantially reduced or abolished. This could be conveniently achieved by including into the recombinant DNA construct of interest, a target site for a microRNA, preferably an endogenous miRNA, differentially expressed between fibers and the rest of the plant, preferably absent in fibers and fiber-developing cells and ubiquitously expressed in all other parts of the plant, so that expression of the miRNA in cells other than fiber or fiber-developing cells directs the post-transcriptional cleavage of any messenger RNA originating by adventitious transcription of the recombinant DNA construct of interest incorporating the miRNA target site, in cells outside the fiber developing cells or fibers. A mirroring selectivity profile (ie. expression limited to cells outside of the fiber developing cells) can also be envisaged.

Incorporation of miRNA target sequences in chimeric constructs has also been described as a trigger for the production of so-called tasiRNAs (trans-acting siRNAs) see e.g. WO 2006/138638 or WO2007/039454.

WO2006/111512 describes improved methods controlling gene expression in the field of genetics, especially plant genetics, and provides agents capable of controlling gene expression. The document specifically provides sequences of naturally occurring, tissue-specifically expressed microRNAs. The patent application further provides for transgenic expression constructs comprising sequences interacting with said microRNAs. By incorporation of the microRNA encoding sequence the expression from said expression construct is specifically silenced in the tissue where the naturally occurring microRNA is naturally expressed. Thereby the expression profile resulting from the promoter is modulated and leakiness is reduced. The document further provides for a method for modulating transgenic expression by incorporating sequences encoding said microRNAs into transgenic expression constructs. The compositions and methods of the invention can be used to enhance performance of agricultural relevant crops and for therapy, prophylaxis, research and diagnostics in diseases and disorders, which afflict mammalian species.

WO2007/047016 describes methods for producing non-natural hybrid seed. Also disclosed are miRNAs and miRNA recognition sites useful for conferring inducible sterility on a crop plant, and recombinant DNA construct including such exogenous miRNA recognition sites.

WO2008/133643 discloses novel microRNAs and their precursors, and recombinant DNA constructs including such novel miRNAs, miRNA precursors, miRNA promoters, and miRNA recognition sites corresponding to the miRNAs. Included are novel miRNA and miRNA precursors that exhibit nutrient-responsive expression. Also disclosed are miRNA decoy sequences. Further provided are non-natural transgenic plant cells, plants, and seeds containing in their genome a recombinant DNA construct as described in the patent application and methods of controlling gene expression using such recombinant DNA constructs.

WO2009/003078 provides molecular constructs and methods for the temporally specific control of gene expression in plants or in plant pests or pathogens. More specifically, this patent application provides plant miRNA genes having novel circadian expression patterns that are useful for designing recombinant DNA constructs for temporally specific expression of at least one gene. Also provided are non-natural transgenic plant cells, plants, and seeds containing in their genome a recombinant DNA construct of this invention.

Kwak et al. (BMC Genomics 2009, 10:457 entitled "Enrichment of a set of microRNAs during the cotton fiber development" describes a deep sequencing approach to investigate global expression and complexity of small RNAs during cotton fiber initiation and development. Two small RNA libraries were prepared and analyzed from wild-type and fuzz/lintless cotton ovules. The study demonstrated significant differences in expression abundance of miRNAs between the wild-type and mutant and suggests that these differentially expressed miRNAs potentially regulate transcripts distinctly involved in cotton fiber development.

Wang et al. (Molecular Plant 2012, Volume 5 Number 4, pages 889-900 entitled "A comparative miRNAome analysis reveals seven fiber initiation-related and 36 novel miRNAs in developing cotton ovules" describes high throughput sequencing combined with computational analysis to characterize miRNAomes from the ovules of wild-type upland cotton and a fibreless mutant during fiber initiation.

The art does remains deficient in describing microRNA molecules with the appropriate expression profile, in particular microRNAs which are expressed and processed in some or all parts of fiber producing plants, particularly cotton plants, except for fibers or fiber developing cells, and whose target sequences could be used to increase the specificity of expression of transgenes (including N-acetylglucosamine transferase and/or glutamine:fructose-6-phosphate amidotransferase) in fibers or fiber-developing cells (compared to the rest of the plant). These and other problems are solved as described hereinafter in the different embodiments, examples and claims.

SUMMARY OF THE INVENTION

In one embodiment of the invention, a recombinant gene for spatially selective expression in a fiber-producing plant is provided comprising the following operably linked elements:
(a) a plant-expressible promoter, such as a constitutive promoter, an inducible-promoter, a tissue-specific promoter, a developmentally regulated promoter or such as a fiber-preferential or fiber-selective promoter, including a promoter selected from the group of a promoter from cotton from a fiber-specific β-tubulin gene, a promoter from cotton from a fiber-specific actin gene, a promoter from a fiber specific lipid transfer protein gene from cotton, a promoter from an expansin gene from cotton, or a promoter from a chitinase gene in cotton; a promoter from cotton from a glucanase gene, a promoter of the cotton FS18 gene, a promoter of the SCW-PRP gene from cotton, a promoter of the FB8-like gene from cotton;
(b) a region encoding a biologically active RNA molecule;
(c) optionally a 3' transcription termination and polyadenylation region characterized in that the recombinant gene further comprises a target sequence recognized by a miRNA, such as a microRNA endogenous to the plant, the miRNA being differentially expressed in cells leading to fibers in the fiber producing plant compared to cells of the fiber-producing plants other than the cells leading to the fibers. Preferably, the target sequence recognized by the miRNA is heterologous to at least one of the elements of the recombinant gene and may be located in a 3' untranslated region of the recombinant gene. The target sequence may be additionally introduced in the recombinant gene or may be obtained by modification of the sequence of one of the operably linked elements, preferably one of the operably linked elements other than the plant-expressible promoter.

In one aspect of the invention, the miRNA is less abundantly or substantially not expressed in cells leading to fibers in the fiber producing plants compared to cells of the fiber-producing plants other than the cells leading to the fibers and may be selected from the group consisting of Ghi_miR403, Ghi_miR408, Ghi_miRcan1230 and Ghi_miR398 or have a nucleotide sequence selected from the nucleotide sequence of SEQ ID No. 1, SEQ ID No. 2, SEQ ID No. 3, SEQ ID No. 4, SEQ ID No. 20, SEQ ID No. 21 or SEQ ID No. 22. The target sequence recognized by the miRNA may thus have the nucleotide sequence of SEQ ID No. 5, SEQ ID No. 5 from nucleotide position 4 to nucleotide position 24, SEQ ID No. 6, SEQ ID No. 6 from nucleotide position 4 to nucleotide position 24, SEQ ID No. 7 or SEQ ID No. 8, SEQ ID No. 23, SEQ ID No. 23 from nucleotide position 4 to 24, SEQ ID No. 23 from nucleotide position 11 to 32, SEQ ID No. 23 from nucleotide positions 4 to 32 or may have a nucleotide sequence which is complementary to the nucleotide sequence of Ghi_miR403, Ghi_miR408, Ghi_miRcan1230, Ghi_miR398, SEQ ID No. 1, SEQ ID No. 2, SEQ ID No. 3, or SEQ ID No. 4, SEQ ID No 20, SEQ ID No 21 or SEQ ID No 22 whereby one or more of the following mismatches may occur:
  (a) a mismatch between the nucleotide at the 5' end of the miRNA and the corresponding nucleotide sequence in the target RNA sequence;
  (b) a mismatch between any one of the nucleotides in position 1 to position 9 of the miRNA and the corresponding nucleotide sequence in the target RNA sequence;
  (c) three mismatches between any one of the nucleotides in position 12 to position 21 of the miRNA and the corresponding nucleotide sequence in the target RNA sequence provided that there are no more than two consecutive mismatches; and
  (d) no mismatch is allowed at positions 10 and 11 of the miRNA.

The recombinant gene according to the invention may encode any protein or polypeptide including a polypeptide with N-acetylglucosamine transferase activity such as a NODC-type N-acetylglucosamine transferase, an N-acetylglucosamine transferase activity comprising a signal anchor sequence selected from the signal anchor sequence of a rat sialyl transferase, the signal anchor sequence of a human galactosyl transferase, the signal anchor sequence of the *Arabidopsis* homologue of the yeast HDEL receptor (AtERD2), the signal anchor sequence of the α-2,6-sialyltransferase, the signal anchor sequence of β1,2-xylosyltransferase from *Arabidopsis thaliana*, the signal anchor sequence of N-acetylgluosoaminyl transferase I from tobacco or the amino acid sequence YYHDL (SEQ ID No. 26) or LKLEI (SEQ ID No:27), or chitin synthase 2 of *Saprolegnia monoica*. The polypeptide may also be glutamine:fructose-6-phosphate amidotransferase.

The invention also provides plant cells, particularly plant cells capable of developing into a fiber cell, as well as plants, parts or tissue thereof or seeds of a plant, comprising a recombinant gene or construct according to the invention. An example of such a plant is a cotton plant.

The invention further relates to a method of producing a fiber-producing plant, such as a cotton plant, with spatially selective expression of a recombinant gene, comprising the steps of
  (a) Introducing a recombinant gene according to the invention into at least one cell of the fiber producing plant; and
  (b) Optionally, regenerating a fiber-producing plant from the at least one cell comprising the recombinant gene.

In yet another aspect of the invention, microRNA from cotton is provided selected from the group of Ghi_miR403, Ghi_miR408, Ghi_miRcan1230, or Ghi_miR398 or having the nucleotide sequence of any one of SEQ ID No. 1, SEQ ID No. 2, SEQ ID No. 3, SEQ ID No. 4, SEQ ID No. 20, SEQ ID No. 21 or SEQ ID No. 22.

The invention also provides target sites recognized by a microRNA according to the invention including target sites having the nucleotide sequence of any one of SEQ ID Nos 5 to 8, SEQ ID 8 from nucleotide position 4 to nucleotide position 24, SEQ ID No. 6 from nucleotide position 4 to nucleotide position 24, SEQ ID No. 8 from nucleotide position 4 to 24, SEQ ID No. 23, SEQ ID No. 23 from nucleotide position 4 to 24, SEQ ID No. 23 from nucleotide position 11 to 32, SEQ ID No. 23 from nucleotide positions 4 to 32, or a nucleotide sequence complementary to a miRNA having a nucleotide sequence according to any one of SEQ ID Nos 1 to 4, SEQ ID No. 20, SEQ ID No. 21 or SEQ ID No. 22 whereby one or more of the following mismatches may occur:
  (a) a mismatch between the nucleotide at the 5' end of the miRNA and the corresponding nucleotide sequence in the target RNA sequence;
  (b) a mismatch between any one of the nucleotides in position 1 to position 9 of the miRNA and the corresponding nucleotide sequence in the target RNA sequence;
  (c) three mismatches between any one of the nucleotides in position 12 to position 21 of the miRNA and the corresponding nucleotide sequence in the target RNA sequence provided that there are no more than two consecutive mismatches; and
  (d) no mismatch is allowed at positions 10 and 11 of the miRNA.

In yet another embodiment of the invention, use of a micro RNA and/or a target site according to the invention is provided to increase the selectivity of fiber-selective expression of a recombinant gene in a fiber-producing cell of a fiber-producing plant, such as a cotton plant.

In still another embodiment of the invention, pre-microRNAs from cotton are provided having a nucleotide sequence of any one of SEQ ID NOs: 9, 10, 11 or 12 or a nucleotide sequence essentially similar or identical thereto wherein the microRNA region and optionally the region complementary to the microRNA region (microRNA* region) have been altered.

The invention also provides a method for producing fibers from a fiber-producing plant, such as cotton, comprising the steps of growing a plant comprising a recombinant gene according to the invention and harvesting fibers from the grown plants as well as plant fibers, such as cotton fibers obtained by such method.

BRIEF DESCRIPTION OF THE FIGURES

The following Examples, not intended to limit the invention to specific embodiments described, may be understood in conjunction with the accompanying Figures, incorporated herein by reference.

Panel A. Spatial and temporal expression pattern for Ghi_miR403 as determined by small RNA deep sequencing. Y-axis: miRNA abundance (reads/million). X-axis: Sample number.

Panel B. Spatial and temporal expression pattern for Ghi_miR403 as determined by Northern blot assays. Shown in the upper panel is a northern blot probed for miR403. GFP-derived, 21- and 24-nt synthetic RNA oligos were used as size markers for endogenous small RNAs. The arrow indicates mature miR403. The lower panel shows the ethidium bromide-stained gel section corresponding to the 5S rRNA and tRNA zone. Sample numbers are indicated below panels.

Panel C. Spatial and temporal expression pattern for Ghi_miR408 as determined by small RNA deep sequencing. Y-axis: miRNA abundance (reads/million). X-axis: Sample number.

Panel D. Spatial and temporal expression pattern for Ghi_miR408 as determined by Northern blot assays. Shown in the upper panel is a northern blot probed for miR408. GFP-derived, 21- and 24-nt synthetic RNA oligos were used as size markers for endogenous small RNAs. The arrow indicates mature miR408. The lower panel shows the ethidium bromide-stained gel section corresponding to the 5S rRNA and tRNA zone. Sample numbers are indicated below panels.

Panel E. Spatial and temporal expression pattern for Ghi_miR398 as determined by Northern blot assays. Shown in the upper panel is a northern blot probed for miR398. GFP-derived, 21- and 24-nt synthetic RNA oligos were used as size markers for endogenous small RNAs. The arrow indicates mature miR398. The lower panel shows the ethidium bromide-stained gel section corresponding to the 5S rRNA and tRNA zone. Sample numbers are indicated below panels.

Panel F. Spatial and temporal expression pattern for Ghi_miRcan1230 as determined by small RNA deep sequencing. Y-axis: miRNA abundance (reads/million). X-axis: Sample number.

Panel G. Spatial and temporal expression pattern for Ghi_miRcan1230 as determined by Northern blot assays. Shown in the upper panel is a northern blot probed for miR1230. GFP-derived, 21- and 24-nt synthetic RNA oligos were used as size markers for endogenous small RNAs. The arrow indicates miRcan1230. The lower panel shows the ethidium bromide-stained gel section corresponding to the 5S rRNA and tRNA zone. Sample numbers are indicated below panels.

Figure 2:
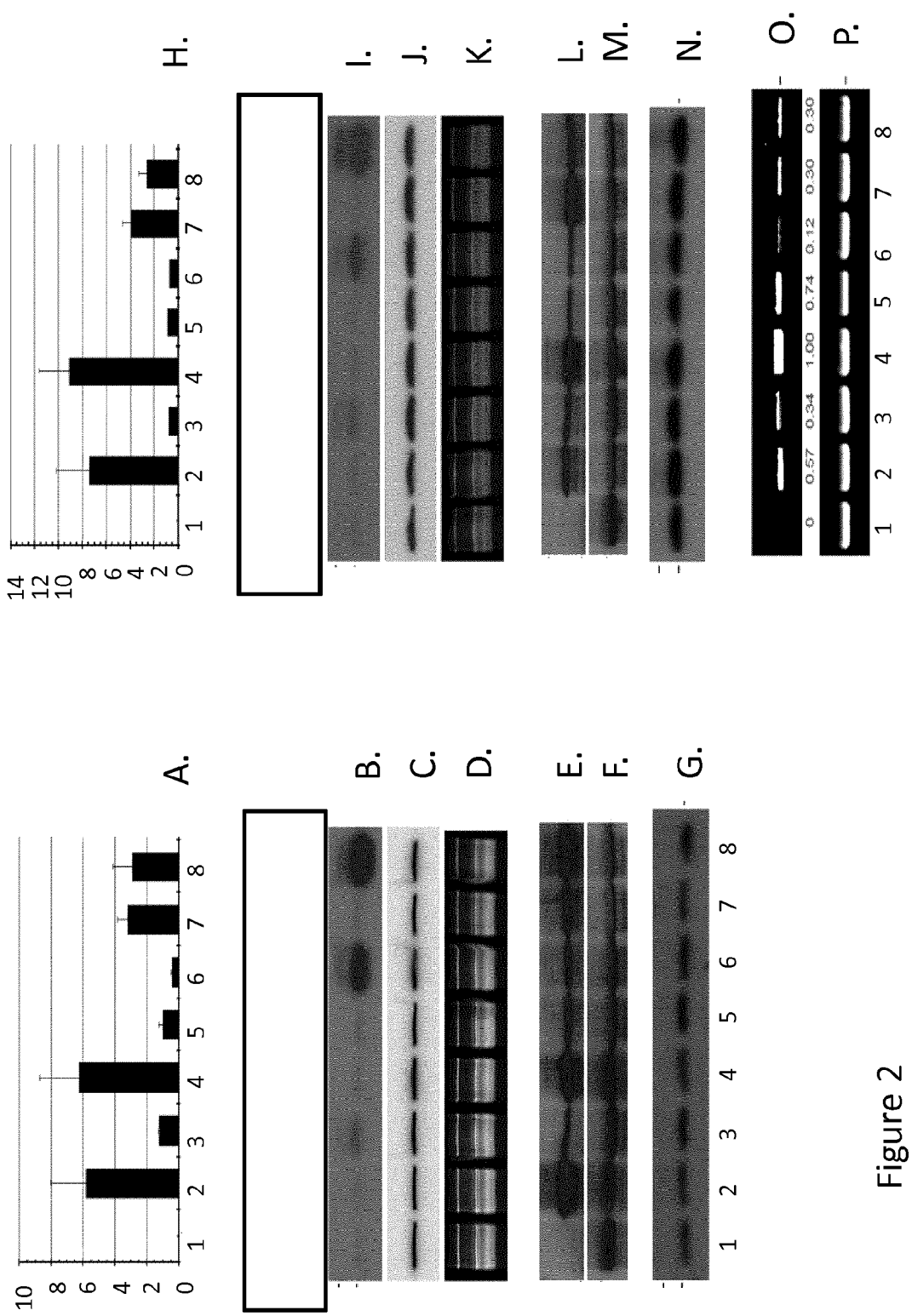

FIG. 2. Validation of miR403-mediated repression of LUC reporter gene expression in an *Agrobacterium*-mediated transient assay system on *Nicotiana benthamiana*. The numbers refer to the following experimental set-up: 1): injection of *Agrobacterium* containing control vector only; 2) injection of *Agrobacterium* containing a T-DNA vector expressing a firefly luciferase (LUC)-based reporter under control of a CaMV35S promoter; 3) injection of *Agrobacterium* containing a T-DNA vector expressing a firefly luciferase (LUC)-based reporter under control of a CaMV35S promoter engineered with a miR403 target site in its 3'UTR; 4) injection of *Agrobacterium* containing T-DNA vector expressing a firefly luciferase (LUC) based reporter under control of a CaMV35S promoter engineered with a mutated miR403 interacting site in its 3'UTR; 5) Co-injection of *Agrobacterium* containing a T-DNA vector expressing a firefly luciferase (LUC)-based reporter under control of a CaMV35S promoter engineered with a miR403 target site in its 3'UTR and *Agrobacterium* containing a control T-DNA vector; 6) Co-injection of *Agrobacterium* containing a T-DNA vector expressing a firefly luciferase (LUC) based reporter under control of a CaMV35S promoter engineered with a miR403 target site in its 3'UTR and a *Agrobacterium* containing a T-DNA vector expressing miR403 pre-miRNA under control of a CaMV35S promoter; 7) Co-injection of *Agrobacterium* containing a T-DNA vector expressing a firefly luciferase (LUC)-based reporter under control of a CaMV35S promoter engineered with a mutated miR403 interacting site in its 3'UTR and a *Agrobacterium* containing a control T-DNA vector; 8) Co-injection of *Agrobacterium* containing a T-DNA vector expressing a firefly luciferase (LUC)-based reporter under control of a CaMV35S promoter engineered with a mutated miR403-interacting site in its 3'UTR and a *Agrobacterium* containing a T-DNA vector expressing miR403 pre-miRNA under control of a CaMV35S promoter.

Panel A and Panel H. LUC activity detected from *Nicotiana benthamiana* leaf tissues sampled at 2 day post injection (dpi) (panel A) or 3 dpi (panel H). Y-axis: Relative LUC activity ($\times 10^7$ unit/mg Fresh Weight); X-axis: sample number.

Panel B and Panel I. Accumulation of miR403 in *Nicotiana benthamiana* leaf tissues sampled at (B) 2 and (I) 3 days post injection as detected by Northern blots. GFP-derived, 21- and 24-nt synthetic RNA oligos were used as size markers for small RNAs.

Panel C and Panel J. Northern blots of panels B and I, probed with U6 small nuclear RNA as control.

Panel D and Panel K. Ethidiumbromide-stained gel section corresponding to the 5S rRNA and tRNA zone from *Nicotiana benthamiana* leaf tissues sampled at 2 day post injection (dpi) (panel D) or 3 dpi (panel K).

Panel E and Panel L. Detection of luciferase protein by immunoblot assay of *Nicotiana benthamiana* leaf tissues sampled at 2 day post injection (panel E) or 3 dpi (panel L) using monoclonal anti-Luciferase antibody produced in mouse.

Panel F and Panel M. Detection of elongation factor 1α protein by immunoblot assay of *Nicotiana benthamiana* leaf tissues sampled at 2 day post injection (panel F) or 3 dpi (panel M) using polyclonal anti-E1F serum antibody produced in rabbit.

Panel G and Panel N. Accumulation of miR168 in *Nicotiana benthamiana* leaf tissues sampled at (G) 2 and (N) 3 days post injection as detected by Northern blots.

Panel O and Panel P. Accumulation of LUC mRNA detected from *Nicotiana benthamiana* leaf tissues sampled at 3 days post injection. Shown in the panel O are the RT-PCR products resolved in an ethidium bromide-stained agarose gel. The relative band intensity reflects the level of intact LUC mRNAs that did not undergo miR403-directed cleavage. Panel P shows the products of control RT-PCR reactions for mRNAs encoding *N. benthamiana* heat shock protein 70-like. Numbers underneath panel O indicate the relative signal intensity as measured by Image Quant.

FIG. 3. Nucleotide sequence of miR403 and miR403-interacting site (target site) (sequences are included in the sequence listing as SEQ ID No 1 for the Ghi_miR403 and Ath_miR403; as SEQ ID No. 18 for the target nucleotide sequence in *Arabidopsis* AGO2 mRNA; as SEQ ID No. 19 for the miR403 form reproduced under the target site; as SEQ ID No. 5 for the miR403 engineered target site; as SEQ ID NO 5 for Ath_miR403_R; and as SEQ ID No. 1 for Ghi_miR403_R).

FIG. 4. Nucleotide sequence of major and minor forms of mature miR408 detected in cotton and of a miR408 target sequence. (Sequences are included in the sequence listing as SEQ ID No. 2 for ghi-miR408.1; as SEQ ID No. 20 for ghi-miR408.2; as SEQ ID No. 6 for miR408-target and as SEQ ID No. 2 for ath-MiR408_R).

FIG. 5. Nucleotide sequence of target sequence (top) and miRNA sequence for the following miRNA detected in cotton: (A) Ghi_miRcan1230-three forms; (B) Ghi_miR398. (Sequences are included in the sequence listing as SEQ IDs No. 10 and 23 for the target sequence of miRcan1230 (1) and combined for miRcan1230 (2) (3) respectively; as SEQ ID No. 3 for miRcan1230 (1) as SEQ ID 21 for miRcan1230 (2), as SEQ ID 22 for miRcan1230 (3); as SEQ ID NO. 4 for miR398 and as SEQ ID No. 8 for the target sequence of miR398. The target sequence for miRcan1230 (3) corresponds to SEQ ID No. 23 from nucleotide 11 to 35, preceded by 5'-a g a-3'.

Figure 6:
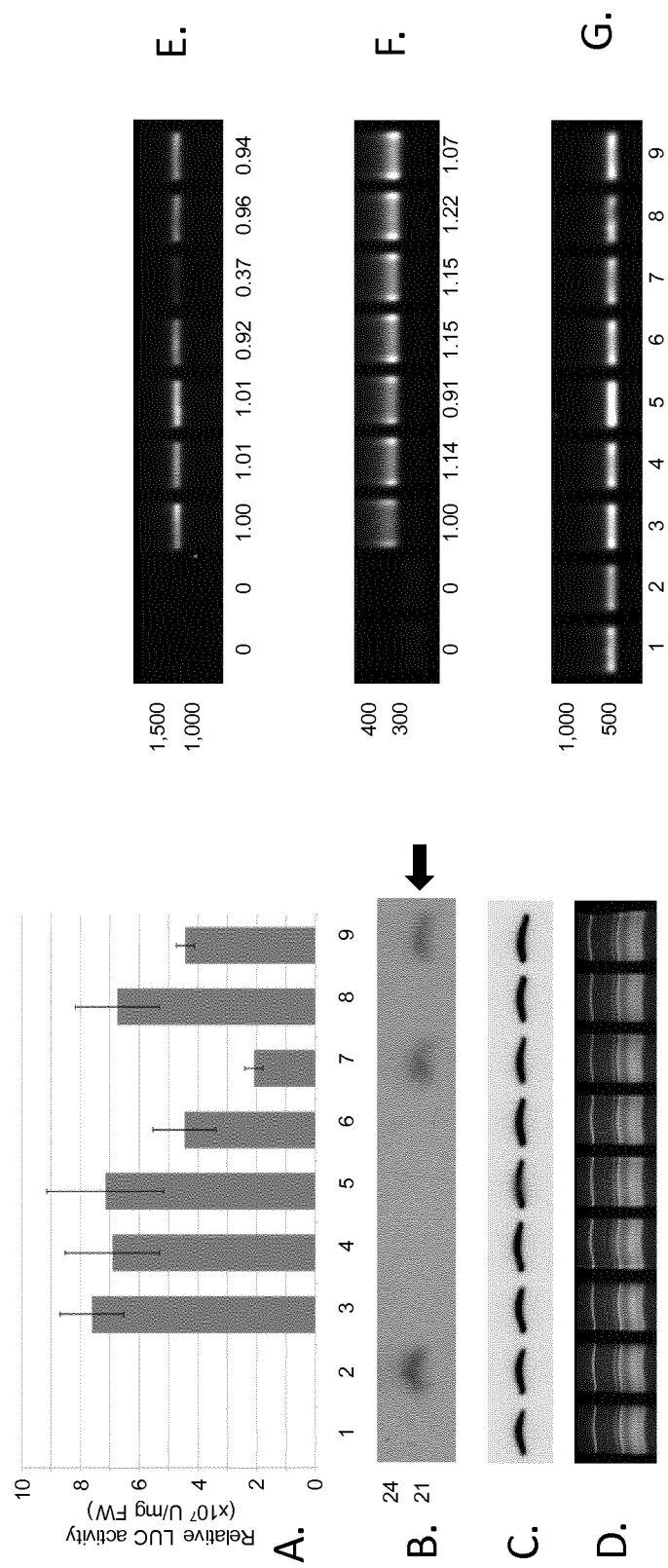

FIG. 6. Validation of miRcan1230-mediated repression of LUC reporter gene expression in an *Agrobacterium*-mediated transient assay system on *Nicotiana benthamiana*. The numbers refer to the following experimental set-up: 1): injection of *Agrobacterium* containing control vector only; 2) injection of *Agrobacterium* containing a T-DNA vector expressing a miRcan1230 pre-microRNA under control of a CaMV35S promoter; 3) injection of *Agrobacterium* containing a T-DNA vector expressing a firefly luciferase (LUC)-based reporter under control of a CaMV35S promoter; 4) injection of *Agrobacterium* containing a T-DNA vector expressing a firefly luciferase (LUC)-based reporter under control of a CaMV35S promoter engineered with a miRcan1230 target site in its 3'UTR; 5) injection of *Agrobacterium* containing T-DNA vector expressing a firefly luciferase (LUC) based reporter under control of a CaMV35S promoter engineered with a mutated miRcan1230 interacting site in its 3'UTR; 6) Co-injection of *Agrobacterium* containing a T-DNA vector expressing a firefly luciferase (LUC)-based reporter under control of a CaMV35S promoter engineered with a miRcan1230target site in its 3'UTR and *Agrobacterium* containing a control T-DNA vector; 7) Co-injection of *Agrobacterium* containing a T-DNA vector expressing a firefly luciferase (LUC) based reporter under control of a CaMV35S promoter engineered with a miRcan1230 target site in its 3'UTR and a *Agrobacterium* containing a T-DNA vector expressing miRcan1230 pre-miRNA under control of a CaMV35S promoter; 8) Co-injection of *Agrobacterium* containing a T-DNA vector expressing a firefly luciferase (LUC)-based reporter under control of a CaMV35S promoter engineered with a mutated miRcan1230 interacting site in its 3'UTR and a *Agrobacterium* containing a control T-DNA vector; 8) Co-injection of *Agrobacterium* containing a T-DNA vector expressing a firefly luciferase (LUC)-based reporter under control of a CaMV35S promoter engineered with a mutated miRcan1230-interacting site in its 3'UTR and a *Agrobacterium* containing a T-DNA vector expressing miRcan1230 pre-miRNA under control of a CaMV35S promoter.

Panel A. LUC activity detected from *Nicotiana benthamiana* leaf tissues sampled at 3 day post injection (dpi). Y-axis: Relative LUC activity ($\times 10^7$ unit/mg Fresh Weight); X-axis: sample number.

Panel B. Accumulation of miRcan1230 in *Nicotiana benthamiana* leaf tissues sampled at 3 days post injection as detected by Northern blots. GFP-derived, 21- and 24-nt synthetic RNA oligos were used as size markers for small RNAs.

Panel C. Northern blots of panel B, probed with U6 small nuclear RNA as control.

Panel D. Ethidiumbromide-stained gel section corresponding to the 5S rRNA and tRNA zone from *Nicotiana benthamiana* leaf tissues sampled at 3 day post injection (dpi).

Panel E and Panel F. Accumulation of LUC mRNA detected from *Nicotiana benthamiana* leaf tissues sampled at 3 days post injection. Shown in the panel E and F are the RT-PCR products resolved in an ethidium bromide-stained agarose gel. The relative band intensity reflects the level of 5' region of LUC mRNAs that did not undergo miRcan1230-directed cleavage (panel E) or the 3' region of LUC mRNAs (panel F).

Panel G shows the products of control RT-PCR reactions for mRNAs encoding *N. benthamiana* heat shock protein 70-like. Numbers underneath panel E and F indicate the relative signal intensity as measured by Image Quant.

DETAILED DESCRIPTION OF PREFERRED EMBODIMENTS

The current invention is based on the fortuitous identification of miRNA molecules (and pre-miRNA molecules as well as target recognitions sites) from cotton (*Gossypium hirsutum*) which are not expressed in developing cotton fiber cells while present in most if not all other cotton plant parts. Such miRNAs, and/or their target sites may be conveniently used to enhance tissue selectivity of expression in a fiber-producing plant, such as cotton.

Thus, in a first embodiment, the invention provides a method for spatially selective expression in a fiber-producing plant, such as cotton, comprising the steps of introducing a recombinant gene into at least one cell of the fiber producing plant, such as cotton, and optionally regenerating a plant from said at least one cell comprising the recombinant construct or gene, whereby the recombinant construct or gene comprises the following operably linked elements (such as DNA elements):

(a) a plant-expressible promoter;
(b) a region encoding a biologically active RNA molecule;
(c) optionally a 3' transcription termination and polyadenylation region and
wherein the recombinant gene or construct further comprises a target sequence recognized by a miRNA which is differentially expressed in cells leading to fibers in the fiber producing plant compared to cells of the fiber-producing plants other than said cells leading to said fibers.

As used herein, the term "promoter" denotes any DNA which is recognized and bound (directly or indirectly) by a DNA-dependent RNA-polymerase during initiation of transcription. A promoter includes the transcription initiation site, and binding sites for transcription initiation factors and RNA polymerase, and can comprise various other sites (e.g., enhancers), at which gene expression regulatory proteins may bind.

As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S, the subterranean clover virus promoter No 4 or No 7, or T-DNA gene promoters and the like.

It will be clear that constitutive plant-expressible promoters may be suitable for the invention. In such cases, the spatial selectivity or tissue-specificity will be provided by the expression profile of the microRNA, which will in turn determine in which tissues or plants of the parts, the transcription products of the recombinant gene incorporating a target sequence for the miRNA, will be processed post-transcriptionally by the miRNA (and associated proteins) to cleave that transcript and thus suppress or prevent further activity of the biologically active RNA (e.g. prevent translation of a peptide or protein encoded by the biologically active RNA).

It is also clear that inducible promoters, such as a temperature inducible or a chemically inducible promoter or a promoter which is responsive to developmental cues, may be used in accordance with the invention. The resulting expression profile of the recombinant gene will be a combined expression profile, mirroring the spatial distribution of the miRNA in the plant and the response to the inducing or repressing factors of the promoter used.

Tissue selective promoters may also be used. In a preferred embodiment of the invention a fiber-preferential or fiber-selective promoter is used.

The term "fiber specific" or "fiber cell specific" or "fiber-selective", with respect to the expression of a gene or with respect to a promoter, refers to, for practical purposes, the highly specific, expression of a gene or expression directed by a promoter, in fiber cells of plants, such as cotton plants. In other words, transcript levels of a DNA in tissues different of fiber cells is either below the detection limit or very low (less than about 0.2 picogram per microgram total RNA).

The term "fiber-preferential" or "fiber-cell preferential" with respect to the expression of a DNA in accordance with this invention, refers to an expression pattern whereby the DNA is expressed predominantly in fiber cells or fibers, but expression can be identified in other tissues of the plant. Preferably, the expression in fiber cells is about 2 to about 10 times higher in the fiber cells than in other tissues.

Such promoters (all herein incorporated by reference) include the promoter from cotton from a fiber-specific β-tubulin gene (as described in WO0210377), the promoter from cotton from a fiber-specific actin gene (as described in WO0210413), the promoter from a fiber specific lipid transfer protein gene from cotton (as described in U.S. Pat. No. 5,792,933), a promoter from an expansin gene from cotton (WO9830698) or a promoter from a chitinase gene in cotton (US2003106097) or the promoters of the fiber specific genes described in U.S. Pat. No. 6,259,003 or U.S. Pat. No. 6,166,294. Fiber selective promoters as described in WO08/083969 (from cotton glucanase genes), WO12/093032 (from cotton FS18 or SCW-PRP gene) or in U.S. application Ser. No. 13/630,119 (from cotton FB8-like genes) are also suitable plant-expressible promoters. Also suitable for the invention is the promoter comprising the nucleotide sequence of SEQ ID 13 from nucleotide position 61 to nucleotide position 1499.

As used herein, a "miRNA" is an RNA molecule of about 20 to 22 nucleotides in length which can be loaded into a RISC complex and direct the cleavage of another RNA molecule, wherein the other RNA molecule comprises a nucleotide sequence essentially complementary to the nucleotide sequence of the miRNA molecule whereby one or more of the following mismatches may occur: a mismatch between the nucleotide at the 5' end of said miRNA and the corresponding nucleotide sequence in the target RNA molecule; a mismatch between any one of the nucleotides in position 1 to position 9 of said miRNA and the corresponding nucleotide sequence in the target RNA molecule; three mismatches between any one of the nucleotides in position 12 to position 21 of said miRNA and the corresponding nucleotide sequence in the target RNA molecule provided that there are no more than two consecutive mismatches. no mismatch is allowed at positions 10 and 11 of the miRNA (all miRNA positions are indicated starting from the 5' end of the miRNA molecule).

A miRNA is processed from a "pre-miRNA" molecule by proteins, such as DCL proteins, present in any plant cell and loaded onto a RISC complex where it can guide the cleavage of the target RNA molecules.

As used herein, a "pre-miRNA" molecule is an RNA molecule of about 100 to about 200 nucleotides, preferably about 100 to about 130 nucleotides which can adopt a secondary structure comprising a double stranded RNA stem and a single stranded RNA loop and further comprising the nucleotide sequence of the miRNA (and its complement sequence) in the double stranded RNA stem. Preferably, the miRNA and its complement are located about 10 to about 20 nucleotides from the free ends of the miRNA double stranded RNA stem. The length and sequence of the single stranded loop region are not critical and may vary considerably, e.g. between 30 and 50 nt in length. Preferably, the difference in free energy between unpaired and paired RNA structure is between −20 and −60 kcal/mole, particularly around −40 kcal/mole. The complementarity between the miRNA and the miRNA* need not be perfect and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex, it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds.

One set of miRNA suitable for methods according to the invention includes miRNAs which are less abundantly expressed in cells leading to fibers in fiber producing plants compared to cells of those fiber-producing plants other than cells leading to said fibers. Especially suited are miRNAs which are substantially not expressed in cells leading to fibers in a fiber-producing plant but ubiquitously expressed in cells other than said cells leading to fibers.

Such miRNAs include the following microRNAs isolated from *Gossypium hirsutum*: Ghi_miR403, Ghi_miR408, Ghi_miRcan1230 and Ghi_miR398. These microRNAs comprise a nucleotide sequence selected from SEQ ID No. 1, SEQ ID No. 2, SEQ ID No. 3, or SEQ ID No. 4 (see also FIGS. 3, 4 and 5). They are processed in *Gossypium hirsutum* from pre-miRNAs comprising the nucleotide sequence of SEQ ID Nos 9, 10, 11 or 12, or a nucleotide sequence essentially similar thereto.

The indication miRcanXXXX refers to the provisional number allocation for new microRNAs, in correspondence with the naming conventions for microRNA.

It will be clear that orthologs of these miRNA or pre-miRNA can be isolated, or identified and used, also in other plants, particularly fiber-producing plants.

"A target sequence recognized by a miRNA" refers to the nucleotide sequence within an RNA molecule towards which the miRNA guides the RISC complex with which it is associated, so that the RNA molecule is cleaved by the ribonuclease activity of an Argonaute protein (AGO) central to the RISC complex. The target sequence is essentially complementary, or complementary to the miRNA nucleotide sequence. As used herein, a nucleotide sequence which is complementary to another nucleotide sequence is a nucleotide sequence with opposite polarity in the phosphor-ribose backbone as the other sequence and which has a nucleotide sequence which allows base-pairing between the bases of the sequence and the other sequence. Base-pairing in this context includes G:U base-pairs as well as standard Watson-Crick base-pairing. It will also be clear that when RNA sequences are the nucleotide sequences to be essentially complementary with DNA sequences, thymine (T) in the DNA sequence is considered equal to uracil (U) in the RNA sequence.

It has been observed that one or more of the following mismatches may occur in the base-pairing between the nucleotides of the target site and the nucleotides of the miRNA:

(a) a mismatch between the nucleotide at the 5' end of said miRNA and the corresponding nucleotide sequence in the target RNA sequence;
(b) a mismatch between any one of the nucleotides in position 1 to position 9 of said miRNA and the corresponding nucleotide sequence in the target RNA sequence;
(c) three mismatches between any one of the nucleotides in position 12 to position 21 of the miRNA and the corresponding nucleotide sequence in the target RNA sequence provided that there are no more than two consecutive mismatches; and
(d) no mismatch is allowed at positions 10 and 11 of the miRNA.

Thus target sites suitable for the invention may comprise a nucleotide sequence which is complementary to the nucleotide sequence of any of the nucleotide sequences of SEQ ID Nos 1 to 4 or which is essentially similar to those nucleotide sequences, and wherein one or more of the above mentioned mismatches occur. Examples of target sites recognized by miRNAs suitable for the invention can be found in FIGS. 3, 4 and 5 and in the sequence listing under entries SEQ ID Nos 5 to 8 and SEQ ID 23 for an engineered target sequence recognized by microRNA Ghi_miRcan1230(2) and (3) respectively. The core target sequence recognized by microRNA Ghi_miRcan1230(2) corresponds to SEQ ID 23 from nucleotide 4 to 24. The core target sequence recognized by microRNA Ghi_miRcan1230(3) corresponds to SEQ ID 23 from nucleotide 11 to 32.

The use of a target site or sequence complementary to the miRNA nucleotide sequence (so-called core target site) will generally be sufficient, but it may be advantageous to include one, two, three or more nucleotides which are flanking the core target site in the nucleotide sequence of the natural target RNA molecule. An example thereof can be found in SEQ ID No 5 where the nucleotide sequence from nucleotide position 4 to nucleotide position 24 corresponds to the core target sequence of miR403, while the additional nucleotide sequence 1 to 3 and 25-27 correspond to the sequences flanking the core target sequence in the natural target RNA molecule. Similarly, an example thereof can be found in SEQ ID No 6 where the nucleotide sequence from nucleotide position 4 to nucleotide position 24 corresponds to the core target sequence of miR408, while the additional nucleotide sequence 1 to 3 and 25-27 correspond to the sequences flanking the core target sequence in the natural target RNA molecule.

Exogenous target site for miRNA may be introduced in the recombinant construct of interest in various manners. The target site nucleotide sequence may be inserted as additional nucleotide sequence. In another embodiment, the miRNA target site may be engineered by modifying a naturally occurring sequence with a sufficient degree of similarity to the target site, according to the rules mentioned elsewhere, to arrive a nucleotide sequence recognized by the miRNAs according to the invention.

The exogenous target sites for miRNA may be introduced anywhere in the transcribed region of the recombinant construct. However, if the transcribed biologically active RNA molecule encodes a polypeptide, care has to be taken that potential introduction of the target site for miRNA in the coding region, preferably does not disrupt the open reading frame or otherwise alters the amino acid sequence of the encoded polypeptide. The target sites for miRNA can be conveniently included in the untranslated regions of the transcript, such as the 5' untranslated region or the 3' untranslated region.

It will be clear to the skilled artisan that the methods and means described herein can be used to obtain spatially selective expression of any gene of interest. However, the methods of the invention can be used to enhance the specificity of expression of genes coding for potentially deleterious products if and when expressed in cells other than fiber cells (and limit such expression substantially to fiber cells in fiber producing plants).

Examples of such nucleotide sequences have been described and include a nucleic acid encoding a polypeptide with N-acetylglucosamine transferase activity which may be an N-acetylglucosamine transferase of the NODC-type, such as a NODC-type N-acetylglucosamine transferase obtainable from a *Rhizobium* species, an *Azorhizobium* species, a *Bradyrhizobium* species, a *Mesorhizobium* species, a *Ralstonia* species, a *Streptomyces* species, a *Burkholderia* species, a *Cupriavidus* species or a *Sinorhizobium* species. The nucleic acid may also encode an N-acetylglucosamine transferase activity, including chitin synthase, further comprising a signal anchor sequence selected from the signal anchor sequence of a rat sialyl transferase, the signal anchor sequence of a human galactosyl transferase, the signal anchor sequence of the *Arabidopsis* homologue of the yeast HDEL receptor (AtERD2), the signal anchor sequence of the α-2,6-sialyltransferase, the signal anchor sequence of β1,2-xylosyltransferase from *Arabidopsis thaliana*, the signal anchor sequence of N-acetylgluosoaminyl transferase I from tobacco or the amino acid sequence YYHDL (SEQ ID No. 26) or LKLEI (SEQ ID No:27). The N-acetylglucosamine transferase may comprise an amino acid sequence encoded by the nucleotide sequence of SEQ ID No. 13 from nucleotide position 1503 to nucleotide position 4439. (Also described in WO 06/136351 incorporated herein by reference). The N-acetylglucosamine transferase may also be chitin synthase, preferably chitin synthase 2 of *Saprolegnia monoica* as described in WO11/089021 (herein incorporated by reference).

The biologically active RNA transcribed from the recombinant DNA, gene or construct according to the invention may also encode a glutamine:fructose-6-phosphate amidotransferase, such as a glutamine:fructose-6-phosphate amidotransferase comprising an amino acid sequence encoded by the nucleotide sequence of SEQ ID No. 13 from nucleotide position 6202 to nucleotide position 8031 or a glutamine:fructose-6-phosphate amidotransferase from *Volvariella volvacea* comprising an amino acid sequence as represented in Genbank entry AAT75220 (incorporated herein by reference).

The invention is also directed towards recombinant constructs or genes as herein described in particular towards a recombinant gene for spatially selective expression in a fiber-producing plant comprising the following operably linked elements:
  (a) a plant-expressible promoter;
  (b) a region encoding a biologically active RNA molecule;
  (c) optionally a 3' transcription termination and polyadenylation region characterized in that the recombinant gene further comprises a target sequence recognized by a miRNA which is differentially expressed in cells leading to fibers in said fiber producing plant compared to other cells of fiber-producing plants.

A "fiber", such as a "cotton fiber", as used herein, refers to a seed trichome, more specifically a single cell of a fiber-producing plant, such as cotton, that initiates from the epidermis of the outer integument of the ovules, at or just prior to anthesis. The morphological development of cotton fibers has been well documented (Basra and Malik, 1984, Int Rev of Cytology 89: 65-113; Graves and Stewart, 1988, supra; Ramsey and Berlin, 1976, American Journal of Botany 63 (6): 868-876; Ruan and Chourey, 1998, Plant Physiology 118: 399-406; Ruan et al. 2000, Aust. J. Plant Physiol. 27:795-800; Stewart, 1975, Am. J. Bot. 62, 723-730). Cotton fibers, in particular from *Gossypium hirsutum*, undergo four overlapping developmental stages: fiber cell initiation, elongation, secondary cell wall biosynthesis, and maturation. Fiber cell initiation is a rapid process. White fuzzy fibers begin to develop immediately after anthesis and continue up to about 3 days post-anthesis (DPA), which is followed by fiber cell elongation (until about 10 to about 17 DPA). Depending upon growth conditions, secondary cell wall biosynthesis initiates and continues to about 25 to about 45 DPA, followed by a maturation process from about 45 to about 60 DPA. The secondary cell wall synthesis and maturation phase are herein commonly referred to as "fiber strength building phase". Only about 25 to 30% of the epidermal cells differentiate into the commercially important lint fibers (Kim and Triplett, 2001). The majority of cells does not differentiate into fibers or develop into short fibers or fuzz. During fiber elongation and secondary wall metabolism, the fiber cells elongate rapidly, synthesize secondary wall components, and show dramatic cellular, molecular and physiological changes. Fiber elongation is coupled with rapid cell growth and expansion (Seagull, 1991. In *Biosynthesis and biodegradation of cellulose* (Haigler, C. H. & Weimer, P. J., eds) pp. 1432163, Marcel Dekker, New York) and constant synthesis of a large amount of cell metabolites and cell wall components such as cellulose. About 95% of the dry-weight in mature cotton fibers is cellulose (Pfluger and Zambryski, 200, Curr Biol 11: R436-R439; Ruan et al., 2001, Plant Cell 13: 47-63). Non-celluloid components are also important to fiber cell development (Hayashi and Delmer, 1988, Carbohydr. Res. 181: 273-277; Huwyler et al., 1979, Planta 146: 635-642; Meinert and Delmer, 1977, Plant Physiol 59: 1088-1097; Peng et al., 2002, Science 295: 147-150). Compared to other plant cells, cotton fibers do not contain lignin in secondary walls but have large vacuoles that are presumably related to rapid cell growth and expansion (Basra and Malik, 1984, supra; Kim and Triplett, 2001, Plant Physiology 127: 1361-1366; Mauney, 1984, supra; Ruan and Chourey, 1998, supra; Ruan et al., 2000, supra; Van't Hof, 1999, American Journal of Botany 86: 776-779).

A "fiber-producing plant" refers to a plant species that produces fibers as defined above, such as a cotton plant. Of the *Gossypium* species, the A genome diploid *Gossypium* species and AD genome allotetraploid *Gossypium* species are known to produce spinnable fiber. Botanically, there are three principal groups of cotton that are of commercial importance. The first, *Gossypium hirsutum* (AADD), is native to Mexico and Central America and has been developed for extensive use in the United States, accounting for more than 95% of U.S. production. This group is known in the United States as American Upland cotton, and their fibers vary in length from about ⅞ to about 1 5/16 inches (about 22-about 33 mm) Worldwide it accounts for about 90% of the cotton production. A second botanical group, *G. barbadense* (AADD), which accounts for about 5% of U.S. production and about 8% of the worldwide production, is of early South American origin. With fibers varying in length from about 1¼ to about 1 9/16 inches (about 32-about 40 mm), it is known in the United States as American Pima, but is also commonly referred to as Extra Long Staple (ELS) cotton. A third group, *G. herbaceum* (AA) and *G. arboreum* (AA), embraces cotton plants with fibers of shorter length, about ½ to about 1 inch (about 13-about 25 mm), that are native to India and Eastern Asia. None from this group is cultivated in the United States.

The term "gene" means a DNA sequence comprising a region (transcribed region), which is transcribed into an RNA molecule (e.g. into a pre-mRNA, comprising intron sequences, which is then spliced into a mature mRNA, or directly into a mRNA without intron sequences) in a cell, operable linked to regulatory regions (e.g. a promoter). A gene (genomic DNA) may thus comprise several operably linked sequences, such as a promoter, a 5' leader sequence comprising e.g. sequences involved in translation initiation, a (protein) coding region (with introns) and a 3' non-translated sequence comprising e.g. transcription termination sites. "cDNA sequence" refers to a nucleic acid sequence comprising the 5' untranslated region, the coding region without introns and the 3' untranslated region and a polyA tail. "Endogenous gene" is used to differentiate from a "foreign gene", "transgene" or "chimeric gene", and refers to a gene from a plant of a certain plant genus, species or variety, which has not been introduced into that plant by transformation (i.e. it is not a "transgene"), but which is normally present in plants of that genus, species or variety, or which is introduced in that plant from plants of another plant genus, species or variety, in which it is normally present, by normal breeding techniques or by somatic hybridization, e.g., by protoplast fusion. Similarly, an "endogenous allele" of a gene is not introduced into a plant or plant tissue by plant transformation, but is, for example, generated by plant mutagenesis and/or selection, introgressed from another plant species by, e.g., marker-assisted selection, or obtained by screening natural populations of plants.

"Expression of a gene" or "gene expression" refers to the process wherein a DNA region, which is operably linked to appropriate regulatory regions, particularly a promoter, is transcribed into an RNA molecule. The RNA molecule is then processed further (by post-transcriptional processes) within the cell, e.g. by RNA splicing and translation initiation and translation into an amino acid chain (polypeptide), and translation termination by translation stop codons. The term "functionally expressed" is used herein to indicate that a functional, i.e. biologically active, protein is produced; the term "not functionally expressed" to indicate that a protein with significantly reduced or no functionality (biological activity) is produced or that no or a significantly reduced amount of protein is produced.

Methods to transform plants are well known in the art and are of minor relevance for the current invention. Methods to transform cotton plants are also well known in the art. *Agrobacterium*-mediated transformation of cotton has been described e.g. in U.S. Pat. No. 5,004,863 or in U.S. Pat. No. 6,483,013 and cotton transformation by particle bombardment is reported e.g. in WO 92/15675.

The chimeric genes according to the invention may be introduced into plants in a stable manner or in a transient manner using methods well known in the art. The chimeric genes may be introduced into plants, or may be generated inside the plant cell as described e.g. in EP 1339859.

The invention is also directed towards fiber-producing plants comprising a recombinant construct according to the invention. Preferred fiber-producing plants include cotton.

"Cotton" as used herein includes *Gossypium hirsutum, Gossypium barbadense, Gossypium arboreum* and *Gossypium herbaceum*. "Cotton progenitor plants" include *Gossypium arboreum, Gossypium herbaceum, Gossypium raimondii, Gossypium longicalyx* and *Gossypium kirkii*.

The methods and means of the current invention may also be employed for other plant species such as hemp, jute, flax and woody plants, including but not limited to *Pinus* spp., *Populus* spp., *Picea* spp., *Eucalyptus* spp. etc.

The plants according to the invention can be used in a conventional breeding scheme to produce more plants with the same characteristics or to introduce the chimeric gene according to the invention in other varieties of the same or related plant species, or in hybrid plants. Seeds obtained from the transformed plants contain the chimeric genes of the invention as a stable genomic insert and are also encompassed by the invention.

The invention is also directed towards a method for producing fibers from fiber-producing plants such as cotton, comprising the steps of a) growing a plant comprising a recombinant construct according to the invention and b) harvesting fibers from the grown plants. Fibers, such as cotton fibers, obtained from these plants are also within the scope of the invention.

The invention also provides novel pre-miRNAs from cotton, in particular pre-microRNAs from cotton having a nucleotide sequence of any one of SEQ ID NOs: 9, 10, 11 or 12. Such pre-miRNAs can be used for any purpose pre-miRNAs are used in the art, including replacing or adapting the microRNA and microRNA* region to obtain a pre-miRNA with a nucleotide sequence essentially similar or identical thereto wherein the microRNA region and optionally the region complementary to the microRNA region (microRNA* region) have been altered and recognize novel target sites. Such engineered pre-miRNAs may be expressed from their naturally associated promoter region, and the engineered miRNA may thereby gain an expression profile similar to that of the miRNAs (e.g. fiber-specific or expression in all plant parts except fibers).

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region, which is functionally or structurally defined, may comprise additional DNA regions etc.

The following non-limiting examples describe the identification of microRNAs from cotton which have a low or no expression in fibers at different developmental stages and use of target sites corresponding to these microRNAs in transgenes.

Unless states otherwise in the Examples, all recombinant techniques are carried out according to standard protocols as described in "Sambrook J and Russell D W (eds.) (2001) Molecular Cloning: A Laboratory Manual, 3rd Edition, Cold Spring Harbor Laboratory Press, New York" and in "Ausubel F A, Brent R, Kingston R E, Moore D D, Seidman J G, Smith J A and Struhl K (eds.) (2006) Current Protocols in Molecular Biology. John Wiley & Sons, New York".

Standard materials and references are described in "Croy RDD (ed.) (1993) Plant Molecular Biology LabFax, BIOS Scientific Publishers Ltd., Oxford and Blackwell Scientific Publications, Oxford" and in "Brown T A, (1998) Molecular Biology LabFax, 2nd Edition, Academic Press, San Diego". Standard materials and methods for polymerase chain reactions (PCR) can be found in "McPherson M J and Møller S G (2000) PCR (The Basics), BIOS Scientific Publishers Ltd., Oxford" and in "PCR Applications Manual, 3rd Edition (2006), Roche Diagnostics GmbH, Mannheim or on the world wide web at roche-applied-science.com".

In the description and examples, reference is made to the following sequences:

SEQ ID No. 1: nucleotide sequence of microRNA Ghi_miR403

SEQ ID No. 2: nucleotide sequence of microRNA Ghi_miR408

SEQ ID No. 3: nucleotide sequence of microRNA Ghi_miR-can1230(1)

SEQ ID No. 4: nucleotide sequence of microRNA Ghi_miR398

SEQ ID No. 5: nucleotide sequence of engineered target sequence recognized by microRNA Ghi_miR403

SEQ ID No. 6: nucleotide sequence of engineered target sequence recognized by microRNA Ghi_miR408

SEQ ID No. 7: nucleotide sequence of target sequence recognized by microRNA Ghi_miRcan1230(1) or (2)
SEQ ID No. 8: nucleotide sequence of target sequence recognized by microRNA Ghi_miR398
SEQ ID No. 9: nucleotide sequence of pre-microRNA Ghi_miR403
SEQ ID No. 10: nucleotide sequence of pre-microRNA Ghi_miR408
SEQ ID No. 11: nucleotide sequence of pre-microRNA Ghi_miRcan1230
SEQ ID No. 12: nucleotide sequence of pre-microRNA Ghi_miR398
SEQ ID No. 13: nucleotide sequence of pTBI312
SEQ ID No. 14: nucleotide sequence of pTEA1_v2
SEQ ID No. 15: nucleotide sequence of pEA2
SEQ ID No. 16: nucleotide sequence of pTEA3
SEQ ID No. 17: nucleotide sequence of pTEA6
SEQ ID No. 18: target sequence of the miR403-interacting site in *Arabidopsis* AGO2 mRNA
SEQ ID No. 19: miR403 from *A. thaliana*
SEQ ID No. 20: minor form of Ghi_miR408
SEQ ID No. 21: nucleotide sequence of alternative form microRNA Ghi_miRcan1230(2)
SEQ ID No. 22: nucleotide sequence of alternative form microRNA Ghi_miRcan1230(3)
SEQ ID No. 23: nucleotide sequence of engineered target sequence recognized by microRNA Ghi_miRcan1230(2) and (3)
SEQ ID No. 24: nucleotide sequence of pTEA9
SEQ ID No. 25: nucleotide sequence of pTEA10
SEQ ID No. 26: Golgi targeting signal from the *Arabidopsis* protein DAGAT1
SEQ ID No. 27: Golgi targeting signal from the *Arabidopsis* protein DAGAT2

EXAMPLES

Example 1. Materials and Methods

Total RNA Extraction and Small RNA Fractionation.
Total RNAs including the low molecular weight (LMW) RNA fraction were extracted from plant materials and sRNAs were isolated by 17% polyacrylamide gel electrophoresis (PAGE) essentially as previously described [Qi, X., Bao, F. S., and Xie, Z. (2009). Small RNA deep sequencing reveals role for *Arabidopsis thaliana* RNA-dependent RNA polymerases in viral siRNA biogenesis. PLoS One 4, e4971].

Small RNA Library Construction and Illumina Sequencing.
PAGE-purified small RNAs were used for custom small RNA library construction essentially as described previously [Qi et al. supra], except that the 5' RNA adapter does not include any custom index sequences. PAGE-purified cDNAs for each small RNA library were submitted for sequencing on Illumina's Hi-Seq2000 instrument.

Plasmid Constructs and Transient Expression Assay.
All binary vectors were constructed using the backbone of pCB302 [Xiang, C., Han, P., Lutziger, I., Wang, K., and Oliver, D. J. (1999). A mini binary vector series for plant transformation. Plant Mol Biol 40, 711-717]. The *Agrobacterium* strain GV2260 transformed with desired binary vectors were used for transient expression assay following established procedure [Johansen, L. K., and Carrington, J. C. (2001). Silencing on the spot. Induction and suppression of RNA silencing in the *Agrobacterium*-mediated transient expression system. Plant Physiol 126, 930-938].

Luciferase Activity Assay.
Luciferase activity was measured using a Luciferase Assay Systems (Promega) following the manufacturer's instructions.

Small RNA Detection by Northern Blot.
LMW RNA blot was done as described previously [Xie, Z., Allen, E., Wilken, A., and Carrington, J. C. (2005). DICER-LIKE 4 functions in trans-acting small interfering RNA biogenesis and vegetative phase change in *Arabidopsis thaliana*. Proc Natl Acad Sci USA 102, 12984-12989]. A locked nucleic acid (LNA) probe (Exiqon) was used for miR403 detection with enhanced sensitivity [Valoczi, A., Hornyik, C., Varga, N., Burgyan, J., Kauppinen, S., and Havelda, Z. (2004). Sensitive and specific detection of microRNAs by northern blot analysis using LNA-modified oligonucleotide probes. Nucleic Acids Res 32, e175].

Analysis of Luciferase mRNA Levels by Reverse Transcription Coupled with Polymerase Chain Reaction (RT-PCR).
Total RNA extracts were enriched for poly (A)$^+$ mRNAs using the Oligotex (Qiagen) procedure following the manufacturer's instructions. The poly (A)$^+$-enriched RNAs (~125 ng) were then used for reverse transcription with Superscript III (Invitrogen), following by PCR using gene-specific primers.

Detection of Luciferase Protein by Immunoblot Assay.
Immunoblot assays were done essentially as described previously [Kasschau, K. D., Xie, Z., Allen, E., Llave, C., Chapman, E. J., Krizan, K. A., and Carrington, J. C. (2003). P1/HC-Pro, a viral suppressor of RNA silencing, interferes with *Arabidopsis* development and miRNA function. Dev Cell 4, 205-217] using a monoclonal anti-Luciferase antibody produced in mouse (Sigma). The control blot for elongation factor 1-alpha was done using polyclonal anti-EF1A serum prepared in rabbit (Agrisera).

Example 2. Identification and Experimental Validation of miRNAs with Desired Expression Patterns Utilization of currently available "tissue-specific promoters" in plant genetic engineering does not always lead to satisfactory outcomes due to "leaky" expression of transgenes outside the desired expression domains. To achieve enhanced tissue- and developmental stage-specific expression of transgenes for genetic engineering of cotton fiber, we use endogenous microRNA (miRNA)-based strategy to eliminate the undesired transgene expression outside the developing cotton fiber. Specifically, when a transgene of interest is engineered with an interaction site for an endogenous miRNA, expression of the transgene would be repressed by such a miRNA when their expression domains overlap spatially or temporally. Endogenous miRNAs that are absent in the developing fiber but are expressed in other tissues could therefore be used as natural agents to knockdown undesired transgene expression outside the fiber.

The recently emerged next-generation DNA sequencing (NGS) technology allows expression profiling of small RNAs using high-throughput platforms in a relatively cost-effective manner Illumina's Sequencing-by-synthesis (SBS) platform was used to obtain the expression profile of cotton miRNAs among different tissue types as well as developmental stages. A total of 12 sampling point points were included for small RNA expression profiling by deep sequencing (sRNA-seq; Table 1). Over 100 million (M) high quality reads were obtained from each small RNA library. Using an in-house-built computational pipeline, putative miRNAs that are conserved in multiple plant species were first identified. A computational approach for de novo identification of miRNAs that have not been reported from any other plant species was then developed.

TABLE 1

Tissue Sampling for Small RNA Expression Profiling

| Sample No. | Tissue type | Developmental Stage | Samle Designation |
|---|---|---|---|
| 1 | Root | 2-leaf stage | Root |
| 2 | Cotyledons | Seedling | Cotyledons |
| 3 | Leaf | 2-leaf stage | Leaf (1) |
| 4 | Leaf | Flowering stage | Leaf (2) |
| 5 | Stem | 2-leaf stage | Stem (1) |
| 6 | Stem | Flowering stage | Stem (2) |
| 7 | Shoot apical meristems | Vegetative growth | SAM |
| 8 | Developing fiber | 8 dpa | Fiber (8 dpa) |
| 9 | Developing fiber | 15 dpa | Fiber (15 dpa) |
| 10 | Developing fiber | 20 dpa | Fiber (20 dpa) |
| 11 | Developing fiber | 25 dpa | Fiber (25 dpa) |
| 12 | Developing fiber | 30 dpa | Fiber (30 dpa) |

The comprehensive small RNA datasets that have been generated allowed extensive and meaningful expression profiling using a computational approach. Several plant miRNAs were identified in cotton which exhibit an interesting expressional pattern and could otherwise be considered as candidates for the purpose of this invention.

However, the majority of these miRNAs turned out to only represent mature miRNAs arising from a subset of paralogous MIRNA loci that form multi-member miRNA families. These miRNAs were removed from the list because certain paralogous MIRNA loci appear to exhibit quite different expression patterns, while the mature miRNAs arising from these loci may be nearly identical in sequence and therefore may share regulatory targets.

The remaining candidates are those miRNAs likely arising from only one or very few paralogous loci. miR403 was present at low abundance in non-fiber samples but was nearly absent in the developing fibers. miR408 which is deeply conserved in land plants, exhibited a similar profile. Others include Ghi_miRcan1230 and Ghi_miR398.

Figure 1:
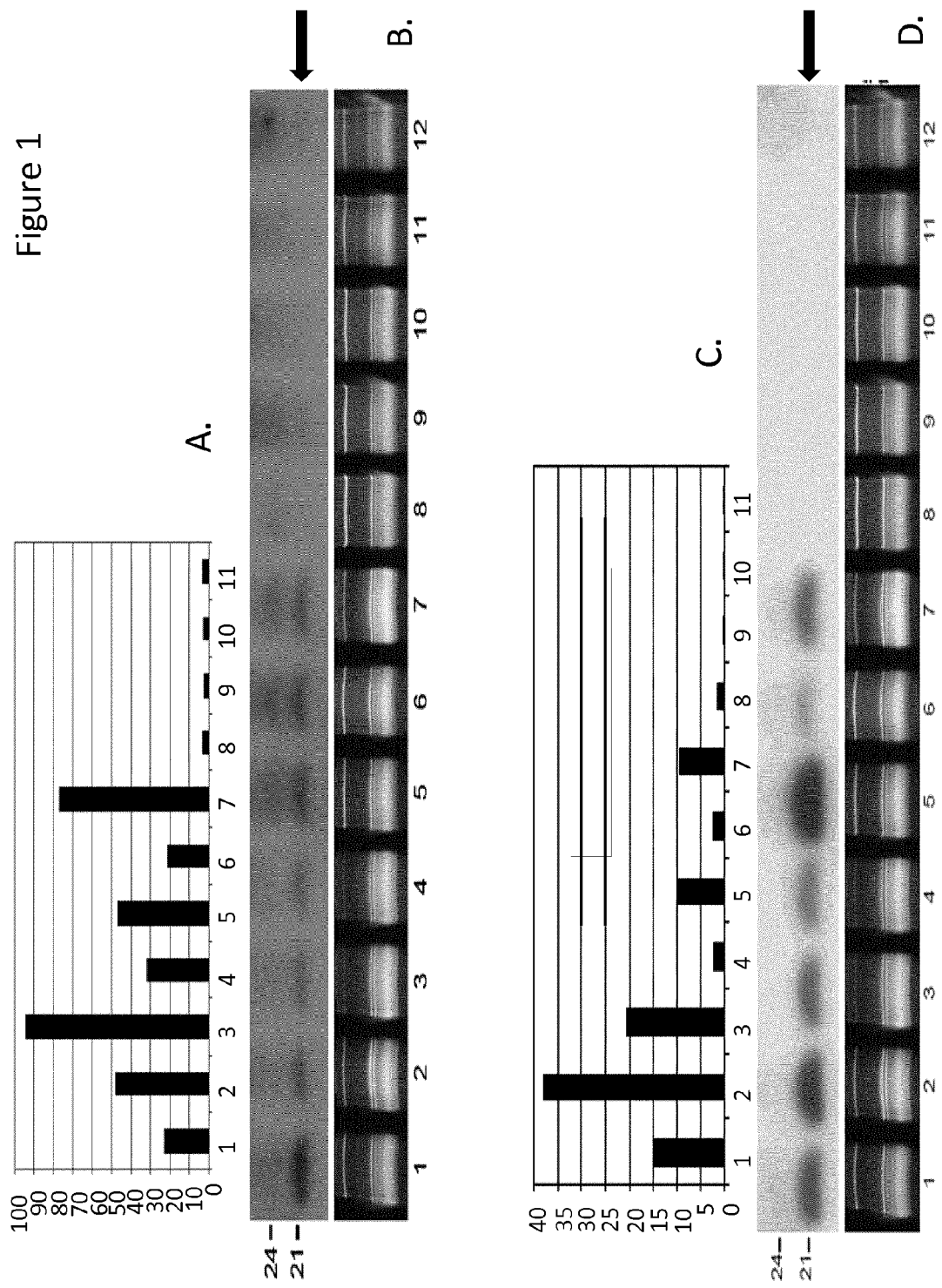
FIG. 1. Experimental validation of spatial and temporal expression pattern for various miRNA in cotton (*Gossypium hirsutum* L. var. FM958) showing a differential pattern between fibers and other parts of the plant. The following sample numbers apply to all panels: 1) Root sampled at 2-leaf stage; 2) cotyledon sampled at seedling stage; 3) Leaf sampled at 2-leaf stage; 4) Leaf sampled at flowering stage; 5) Stem sampled at 2-leaf stage; 6) Stem sampled at flowering stage; 7) Shoot apical meristems (SAM) sampled during vegetative growth; 8) Developing fiber 8 days post-anthesis (dpa); 9) Developing fiber 15 dpa; 10) Developing fiber 20 dpa; 11) Developing fiber 25 dpa; 12) Developing fiber 30 dpa.
Figure 1:
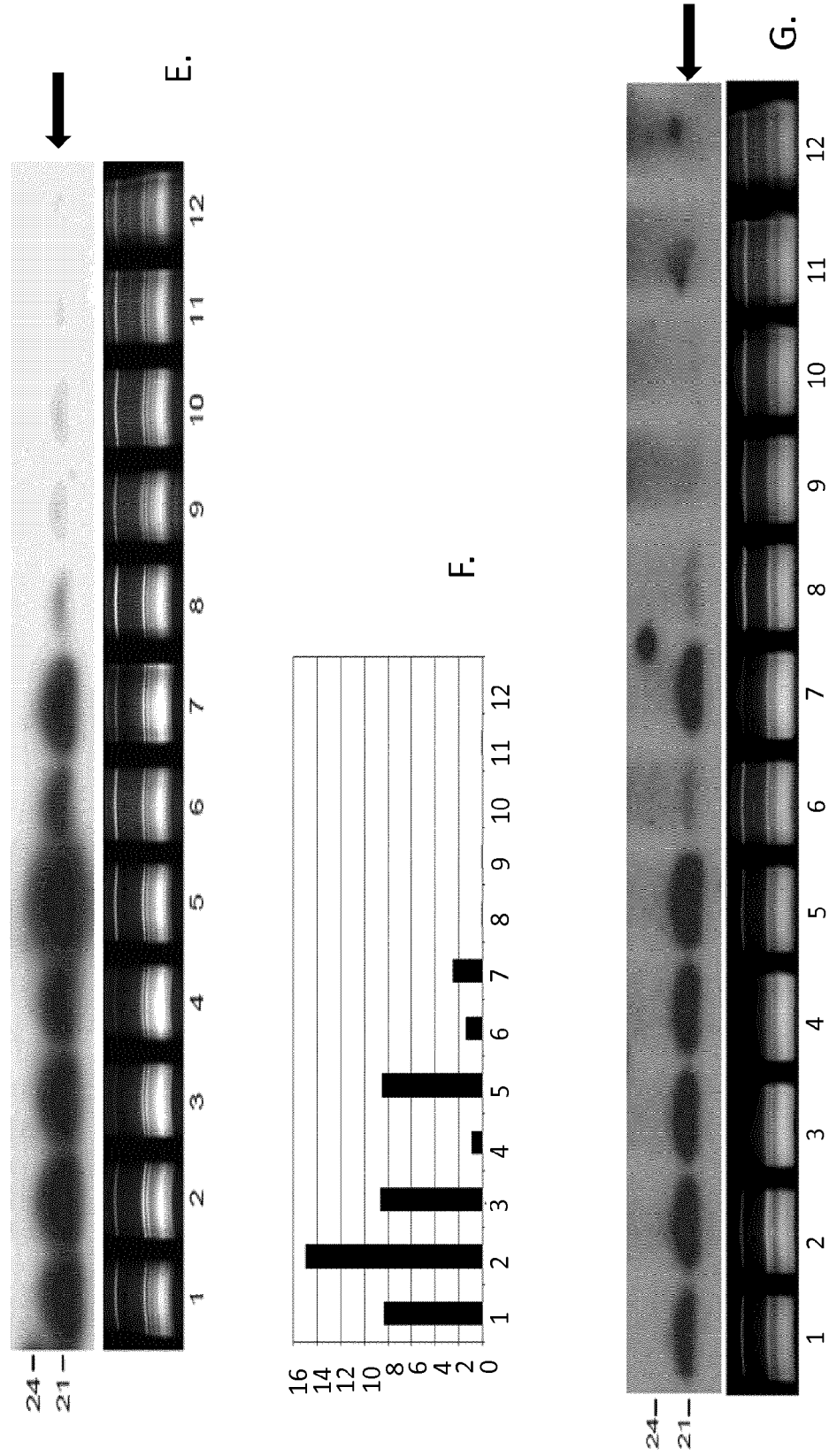

These expression patterns were experimentally validated and confirmed by Northern blot-based assays (FIG. 1).

Example 3. Validation of miR403-Mediated Repression of LUC Reporter in a Transient Assay System Although multiple miRNAs may be considered for use as a natural agent for clearance of undesired transgene expression in the non-fiber tissues in cotton, we have chosen miR403 as the first subject for further experimental validation due to its conserved nature and well-established interactions with its target in $Arabidopsis$. Briefly, miR403 is a semi-conserved plant miRNA that has been found only in the dicotyledonous species [Cuperus, J. T., Fahlgren, N., and Carrington, J. C. (2011). Evolution and functional diversification of MIRNA genes. Plant Cell 23, 431-442]. In $Arabidopsis$, miR403 has been shown to target the 3' untranslated region (3' UTR) of mRNA for ARGONAUTE2 (AGO2), one of 10 AGO family proteins in this reference plant species [Jones-Rhoades, M. W., Bartel, D. P., and Bartel, B. (2006). MicroRNAs and their regulatory roles in plants. Annu Rev Plant Biol 57, 19-53; Vaucheret, H. (2008). Plant ARGONAUTES. Trends Plant Sci 13, 350-358]. The outcome of the interaction between miR403 and its target involves cleavage of AGO2 mRNA [Allen, E., Xie, Z., Gustafson, A. M., and Carrington, J. C. (2005). microRNA-directed phasing during trans-acting siRNA biogenesis in plants. Cell 121, 207-221; Xie, Z., Allen, E., Fahlgren, N., Calamar, A., Givan, S. A., and Carrington, J. C. (2005). Expression of $Arabidopsis$ MIRNA genes. Plant Physiol 138, 2145-2154]. The $Arabidopsis$ AGO2 is believed to play a role in defense against certain viral pathogens [Harvey, J. J., Lewsey, M. G., Patel, K., Westwood, J., Heimstadt, S., Carr, J. P., and Baulcombe, D. C. (2011). An antiviral defense role of AGO2 in plants. PLoS One 6, e14639; Jaubert, M., Bhattacharjee, S., Mello, A. F., Perry, K. L., and Moffett, P. (2011). ARGONAUTE2 mediates RNA-silencing antiviral defenses against Potato virus X in $Arabidopsis$. Plant Physiol 156, 1556-1564; Wang, X. B., Jovel, J., Udomporn, P., Wang, Y., Wu, Q., Li, W. X., Gasciolli, V., Vaucheret, H., and Ding, S. W. (2011). The 21-nucleotide, but not 22-nucleotide, viral secondary small interfering RNAs direct potent antiviral defense by two cooperative argonautes in $Arabidopsis$ $thaliana$. Plant Cell 23, 1625-1638]. However, AGO2 does not appear to play an essential role for normal growth and development, as loss-of-function mutations in AGO2 do not appear to result in any notable defect [Vaucheret, H. (2008). Plant ARGONAUTES. Trends Plant Sci 13, 350-358; Mallory, A., and Vaucheret, H. (2010). Form, function, and regulation of ARGONAUTE proteins. Plant Cell 22, 3879-3889].

Taking advantage of the well-characterized sequences involved in miR403-target interaction in $Arabidopsis$, a firefly luciferase (LUC)-based reporter has been designed [Xiong, L., David, L., Stevenson, B., and Zhu, J. (1999). High throughput screening of signal transduction mutant with luciferase imaging. Plant Molecular Biology Reporter 17, 159-170] engineered with a miR403 target site in its 3'UTR (designated as 35S::LUC-TAR$^{miR403}$). The efficacy of miR403-mediated down-regulation of LUC reporter expression was assessed by expressing the 35S::LUC-TAR$^{miR403}$, either alone or co-expressed with a 35S promoter-driven MIR403-producing construct (designated 35S::miR403) in an $Agrobacterium$-mediated transient assay system on $Nicotiana$ $benthamina$ [Johansen, L. K., and Carrington, J. C. (2001). Silencing on the spot. Induction and suppression of RNA silencing in the $Agrobacterium$-mediated transient expression system. Plant Physiol 126, 930-938]. LUC reporter constructs either lacking the miR403 target site (designated 35S::LUC) or harboring a mutated miR403 interacting site (designated as 35S::LUC-TAR$^{miR403m}$) were also made to serve as controls.

The following scheme for co-injection was used.
1. Control vector only
2. 35S::LUC alone
3. 35S::LUC-TAR$^{miR403}$ alone
4. 35S::LUC-TAR$^{miR403m}$ alone
5. 35S::LUC-TAR$^{miR403}$+control vector
6. 35S::LUC-TAR$^{miR403}$+35S::miR403
7. 35S::LUC-TAR$^{miR403m}$+control vector
8. 35S::LUC-TAR$^{miR403m}$+35S::miR403

At two days post injection (2 d.p.i.), luciferase activities were readily detectable from leaves infiltrated with 35S::LUC, but not from those infiltrated with the vector control (FIG. 2A). In leaves infiltrated with a miR403-targetable version of the LUC construct (35S::LUC-TAR$^{miR403}$), however, substantially lower luciferase activities were detected when compared to the 35S::LUC (FIG. 2A), presumably due to a repression caused by the endogenous miR403 naturally expressed in the $N.$ $benthamiana$ leaves. Small RNA Northern blot assays confirmed that this was indeed the case, as low levels of miR403 accumulation were detected from the leaves infiltrated with the vector control (FIGS. 2B and I). Consistent with an efficient posttranscriptional "knock down" of 35S::LUC-TAR$^{miR403}$ expression by the endogenous miR403 from the *N. benthamiana* leaves, mutations that disrupt the miR403 interaction site in the engineered LUC reporter restored the luciferase activity to a level that is comparable to that detected from the 35S::LUC (FIG. 2A; see the sample labeled with 35S::LUC-TAR$^{miR403m}$). Such a general trend in luciferase activity was also observed in samples taken at 3d.p.i. (FIG. 2B). To examine the effect of exogenous miR403 on the expression of LUC reporter, we also included in our experiment the "two-component" *Agrobacterium* injection treatments where the LUC reporter is co-expressed with transgenic miR403. As shown in FIG. 2, substantially elevated levels of miR403 accumulation were observed whenever the 35S::MIR403 construct was included in the co-infiltration (FIGS. 2B and I). When the miR403-targetable version of the LUC construct (35S::LUC-TAR$^{tR403}$) was co-injected with 35S::MIR403, a further reduction in the luciferase activity was observed when compared with the control co-injection with the vector (FIGS. 2A and H), an indication that transgenically expressed miR403 further reinforced the silencing effect of endogenous miR403 upon its targets. As expected, regardless of co-injection with either the 35S::MIR403 or the vector control, the LUC reporter harboring a mutated miR403 interaction site (35S::LUC-TAR$^{miR403m}$) exhibited elevated luciferase activities when compared with its miR403 targetable counterpart (FIGS. 2A and H). These data were consistent with, and further substantiated by, the levels of full-length LUC mRNAs detected by RT-PCR based assays (FIGS. 2 O and P).

In summary, consistent results were obtained showing that the expression of 35S::LUC-TAR$^{miR403}$ can be effectively repressed by the *N. benthamiana* endogenous miR403, while the expression of a non-targeted LUC (35S::LUC) or the LUC with a mutated miR403 target (35S::LUC-TAR$^{miR403m}$) was not affected. The expression of 35S::LUC-TAR$^{miR403}$ can be further down-regulated when it is co-expressed with 35S::MIR403 which provides additional mature miR403.

Example 4. Validation of miRcan1230-Mediated Repression of LUC Reporter in a Transient Assay System Using the candidate target sequences involved in miRcan1230-target interaction in *Arabidopsis*, a firefly luciferase (LUC)-based reporter has been designed [Xiong, L., David, L., Stevenson, B., and Zhu, J. (1999). High throughput screening of signal transduction mutant with luciferase imaging. Plant Molecular Biology Reporter 17, 159-170] engineered with a miRcan1230 target site in its 3'UTR (designated as 35S::LUC-TAR$^{miRcan1230}$). The efficacy of miRcan1230-mediated down-regulation of LUC reporter expression was assessed by expressing the 35S::LUC-TAR$^{miRcan1230}$, either alone or co-expressed with a 35S promoter-driven MIRcan1230-producing construct (designated 35S::miRcan1230) in an *Agrobacterium*-mediated transient assay system on *Nicotiana benthamina* [Johansen, L. K., and Carrington, J. C. (2001). Silencing on the spot. Induction and suppression of RNA silencing in the *Agrobacterium*-mediated transient expression system. Plant Physiol 126, 930-938]. LUC reporter constructs either lacking the miRcan1230 target site (designated 35S::LUC) or harboring a mutated miRcan1230 interacting site (designated as 35S::LUC-TAR$^{miRcan1230m}$) were also made to serve as controls.

The following scheme for co-injection was used.
1. Control vector only
2. 35S::LUC-TAR$^{miRcan1230}$ alone
3. 35S::LUC alone
4. 35S::LUC-TAR$^{miRcan1230}$ alone
5. 35S::LUC-TAR$^{miRcan1230m}$ alone
6. 35S::LUC-TAR$^{miRcan1230}$+control vector
7. 35S::LUC-TAR$^{miRcan1230}$+35S::miRcan1230
8. 35S::LUC-TAR$^{miRcan1230m}$+control vector
9. 35 S::LUC-TAR$^{miRcan1230m}$+35S::miRcan1230

At three days post injection (3 d.p.i.), luciferase activities were readily detectable from leaves infiltrated with 35S::LUC, but not from those infiltrated with the vector control (FIG. 6A lanes 3 and 1). In leaves infiltrated with a miRcan1230-targetable version of the LUC construct alone (lane 4) (35S::LUC-TAR$^{miRcan1230}$), luciferase activities were detected comparable to the 35S::LUC (FIG. 6A, lane 3), as there appears to be no repression which can be caused by endogenous miRcan1230 in the *N. benthamiana* leaves, as cotton miRcan1230 is not conserved in other species. Small RNA Northern blot assays indicated that miRcan1230 accumulation was detected only from the leaves infiltrated with the 35S:miRcan1230 construct only (FIG. 6B, lanes 2, 7 and 9).

To examine the effect of exogenously expressed miRcan1230 on the expression of LUC reporter, we included in our experiment the "two-component" *Agrobacterium* injection treatments where the LUC reporter is co-expressed with transgenic miRcan1203. As shown in FIG. 6, substantially elevated levels of miRcan1230 accumulation were observed whenever the 35S::MIRcan1230 construct was included in the co-infiltration and only then (FIG. 6B). When the miRcan1230-targetable version of the LUC construct (35S::LUC-TAR$^{miRcan1230}$) was co-injected with 35S::MIRcan1230, a significant reduction in the luciferase activity was observed when compared with the control co-injection with the vector (FIG. 6A), an indication that transgenically expressed miRcan1230 exercised the silencing effect of miRcan1230 upon its targets. As expected, regardless of co-injection with either the 35S::MIRcan1230 or the vector control, the LUC reporter harboring a mutated miRcan1230 interaction site (35S::LUC-TAR$^{miRcan1230m}$) exhibited elevated luciferase activities when compared with its miRcan1203 targetable counterpart (FIG. 6A).

These data were consistent with, and further substantiated by, the levels of LUC mRNAs detected by RT-PCR based assays (FIGS. 6 E and F). The RT-PCR based assays distinguished between detection of the 5' part of the LUC mRNA (region A) upstream of the miRcan1230 target site or the 3' part of the LUC mRNA (region B), downstream of the miRcan1230 target site. Region A cannot be detected when no 35S::LUC vector (with or without target site) has been injected (lanes 1 and 2) but is also significantly reduced when the 35S::LUC TAR$^{miRcan1230}$ is coexpressed with 35S:MIRcan1230. Region B can always be detected except when no 35S::LUC vector (with or without target site) has been injected.

In summary, consistent results were obtained showing that the expression of 35S::LUC-TAR$^{miRcan1230}$ can be effectively repressed by the *N. benthamiana* only when it is co-expressed with 35S::MIRcan1230 which provides mature miRcan1230.

Example 5. miR403-Mediated or miR408-Mediated Repression of Chitin Synthase and/or Glutamine:Fructose-6-Phosphate Amidotransferase in Cotton Fibers Using recombinant DNA techniques the following recombinant genes were constructed by operably linking the following DNA elements:

Recombinant construct chitin synthase+miR408 binding site
The Pscw-prpr promoter
A DNA region coding for golgi-targeting signal from Xy1T35 fused to the coding sequence from chitin synthase from *Neurospora crassa*
A sequence including the binding site of microRNA408
The 3'UTR fragment from the CaMV 35S gene
Further details are included in Table 2 referring to SEQ ID No. 15.

Recombinant glutamine:fructose-6-phosphate amidotransferase+miR408 binding site
The Pscw-prpr promoter
A DNA region coding for the glutamine:fructose-6-phosphate amidotransferase of *Escherichia coli*
A sequence including the binding site of microRNA408
3' untranslated region of the histone H4 gene of *Arabidopsis thaliana*
Further details are included in Table 3 referring to SEQ ID No. 14.

Recombinant construct chitin synthase+miR403 binding site
The Pscw-prpr promoter
A DNA region coding for golgi-targeting signal from Xy1T35 fused to the coding sequence from chitin synthase from *Neurospora crassa*
A sequence including the binding site of microRNA403
The 3'UTR fragment from the CaMV 35S gene
Further details are included in Table 4 referring to SEQ ID No. 13.

Recombinant glutamine:fructose-6-phosphate amidotransferase+miR403 binding site
The Pscw-prpr promoter
A DNA region coding for the glutamine:fructose-6-phosphate amidotransferase of *Escherichia coli*
A sequence including the binding site of microRNA403
3' untranslated region of of the histone H4 gene of *Arabidopsis thaliana*
Further details are included in Table 4 referring to SEQ ID No. 13.

The recombinant constructs were inserted in various combinations in T-DNA vectors together with a selectable marker, such as a plant-expressible glyphosate tolerance gene. Examples of such T-DNA vectors include pTEA1 (comprising recombinant glutamine:fructose-6-phosphate amidotransferase followed by miRNA408 binding site; SEQ ID No. 14) and pTDBI312 (comprising recombinant glutamine:fructose-6-phosphate amidotransferase followed by miRNA403 binding site and recombinant chitin synthase followed by miRNA403 binding site; SEQ ID No. 13) pTEA6 (containing glutamine:fructose-6-phosphate amidotransferase with a miR403 target site in its 3' UTR and chitin synthase with a miR408 target site in its 3' UTR; Table 6 and SEQ ID No. 17) or pTEA3 (containing glutamine:fructose-6-phosphate amidotransferase and chitin synthase both with a miR408 target site in their 3' UTR; Table 5 and SEQ ID No. 16).

These T-DNA vectors were introduced into *Agrobacterium* strains containing a helper Ti-plasmid and used in cotton transformation essentially as described in WO00/71733.

Transgenic cotton plants were regenerated and the expression of glutamine:fructose-6-phosphate amidotransferase and chitin synthase in cotton fibers is determined. Transgenic cotton plants comprising recombinant constructs with miRNA target sites in their 3'UTR show less disadvantageous phenotypes (small plants etc.) than transgenic cotton plants comprising recombinant constructs without miRNA target sites in their 3'UTR.

Example 6. miRcan1230-Mediated or miR398-Mediated Repression of Chitin Synthase and/or Glutamine: Fructose-6-Phosphate Amidotransferase in Cotton Fibers Using recombinant DNA techniques the following recombinant genes were constructed by operably linking the following DNA elements:

Recombinant construct chitin synthase+miR398 binding site
The Pscw-prp promoter
A DNA region coding for golgi-targeting signal from Xy1T35 fused to the coding sequence from chitin synthase from *Neurospora crassa*
A sequence including the binding site of microRNA398
The 3'UTR fragment from the CaMV 35S gene
Further details are included in Table 7 referring to SEQ ID No. 24.

Recombinant glutamine:fructose-6-phosphate amidotransferase+miRcan1230 binding site
The Pscw-prp promoter
A DNA region coding for the glutamine:fructose-6-phosphate amidotransferase of *Escherichia coli*
A sequence including the binding site of microRNA398
3' untranslated region of the histone H4 gene of *Arabidopsis thaliana*
Further details are included in Table 7 referring to SEQ ID No. 24.

Recombinant construct chitin synthase+miRcan1230 binding site
The Pscw-prp promoter
A DNA region coding for golgi-targeting signal from Xy1T35 fused to the coding sequence from chitin synthase from *Neurospora crassa*
A sequence including the binding site of microRNAcan1230
The 3'UTR fragment from the CaMV 35S gene
Further details are included in Table 8 referring to SEQ ID No. 25.

Recombinant glutamine:fructose-6-phosphate amidotransferase+miRcan1230 binding site
The Pscw-prp promoter
A DNA region coding for the glutamine:fructose-6-phosphate amidotransferase of *Escherichia coli*
A sequence including the binding site of microRNAcan1230
3' untranslated region of of the histone H4 gene of *Arabidopsis thaliana*
Further details are included in Table 8 referring to SEQ ID No. 25.

The recombinant constructs were inserted in various combinations in T-DNA vectors together with a selectable marker, such as a plant-expressible glyphosate tolerance gene. Examples of such T-DNA vectors include pTEA9 (comprising recombinant glutamine:fructose-6-phosphate amidotransferase followed by miRNA398 binding site and recombinant chitin synthase followed by miRNA398 binding site; SEQ ID No. 24) and pTEA10 (containing glutamine:fructose-6-phosphate amidotransferase with a miRcan1230 target site in its 3' UTR and chitin synthase with a miRcan1230 target site in its 3' UTR; SEQ ID No. 25).

These T-DNA vectors were introduced into *Agrobacterium* strains containing a helper Ti-plasmid and used in cotton transformation essentially as described in WO00/71733.

Transgenic cotton plants were regenerated and the expression of glutamine:fructose-6-phosphate amidotransferase and chitin synthase in cotton fibers is determined. Transgenic cotton plants comprising recombinant constructs with miRNA target sites in their 3'UTR show less disadvantageous phenotypes (small plants etc.) than transgenic cotton plants comprising recombinant constructs without miRNA target sites in their 3'UTR.

TABLE 2 genetic elements of recombinant DNA construct pEA2 comprising chitin synthase and + miR408 target site - nucleotide sequence reference is SEQ ID No. 15

| Name | Start | End | Description |
| --- | --- | --- | --- |
| Pscw-prp | 431 | 1869 | promoter from proline rich cell wall protein from *G. hirsutum*; |
| RPxylTAt | 1873 | 1977 | coding sequence for the Golgi retention peptide of the beta-1, 2- xylosyltransferase gene of *Arabidopsis thaliana* (Pagny et al., 2003) |
| chs2Nc-1Pc | 1978 | 4809 | coding sequence for chitin synthase from *Neurospora crassa* |
| tmiR408At-N1 | 4822 | 4848 | sequence including the binding site of microRNA408 of *Arabidopsis thaliana* |
| tmiR408At | 4825 | 4845 | Core target sequence of microRNA408 of *Arabidopsis thaliana* |
| 3'35S | 4869 | 5105 | 3'UTR fragment from the CaMV 35S gene. |

TABLE 3 genetic elements of T-DNA of vector pTEA1 comprising recombinant construct containing glutamine:fructose-6-phosphate amidotransferase and miR408 target site - reference is SEQ ID No. 14

| Name | Start | End | Description |
| --- | --- | --- | --- |
| RB | 10979 | 11003 | Right border repeat from the T-DNA of *Agrobacterium tumefaciens* (Zambryski, 1988) |
| Pscw-prp | 11067 | 12505 | sequence including the promoter region of a proline-rich cell wall protein gene of *Gossypium hirsutum* (cotton) |
| gfaEc-1Pb | 12509 | 14338 | coding region of the glutamine:fructose-6-phosphate amidotransferase gene of *Escherichia coli* (Frohberg and Essigmann, 2006), adapted to plant codon usage |
| tmiR408At-N1 | 14339 | 44 | sequence including the binding site of microRNA408 of *Arabidopsis thaliana* (Harvey et al., 2011) |
| tmiR408At | 3 | 41 | Core target sequence of microRNA408 of *Arabidopsis thaliana* |
| 3'histonAt | 60 | 720 | sequence including the 3' untranslated region of the histone H4 gene of *Arabidopsis thaliana* (Chabouté et al., 1987) |
| Ph4a748 ABC | 770 | 1686 | sequence including the promoter region of the histone H4 gene of *Arabidopsis thaliana* (Chabouté et al., 1987) |
| intron1 h3At | 1736 | 2198 | sequence including the first intron of gene II of the histone H3.III variant of *Arabidopsis thaliana* (Chaubet et al., 1992) |
| TPotp C | 2205 | 2576 | coding sequence of the optimized transit peptide, containing sequence of the RuBisCO small subunit genes of *Zea mays* (corn) and *Helianthus annuus* (sunflower) (Lebrun et al., 1996) |
| 2mepsps | 2577 | 3914 | coding sequence of the double-mutant 5-enol-pyruvylshikimate-3-phosphate synthase gene of *Zea mays* (corn) (Lebrun et al., 1997) |
| 3'histon At | 3938 | 4598 | sequence including the 3' untranslated region of the histone H4 gene of *Arabidopsis thaliana* (Chabouté et al., 1987) |
| LB | 4711 | 4735 | Left border repeat from the T-DNA of *Agrobacterium tumefaciens* (Zambryski, 1988) |

TABLE 4 genetic elements of T-DNA of vector pTBDI312 comprising recombinant construct containing glutamine:fructose-6-phosphate amidotransferase and chitin synthase both containing a miR403 target site in their 3' UTR - reference is SEQ ID No. 13

| Name | Start | End | Description |
| --- | --- | --- | --- |
| RB | 1 | 25 | Right border repeat from the T-DNA of *Agrobacterium tumefaciens* (Zambryski, 1988) |
| Pscw-prp | 61 | 1499 | sequence including the promoter region of a proline-rich cell wall protein gene of *Gossypium hirsutum* (cotton) |
| RPxylTAt | 1503 | 1607 | coding sequence for the Golgi retention peptide of the beta-1,2-xylosyltransferase gene of *Arabidopsis thaliana* (Pagny et al., 2003) |
| chs2Nc-1Pc | 1608 | 4439 | coding sequence of the chitin synthase 2 gene of *Neurospora crassa* (Din and Yarden, 1994) |
| tmiR403At-N1 | 4440 | 4465 | sequence including the binding site of microRNA403 of *Arabidopsis thaliana* (Harvey et al., 2011) |
| tmiR403At | 4443 | 4462 | Core binding site of microRNA403 of *Arabidopsis thaliana* |
| 3'35S | 4486 | 4722 | sequence including the 3' untranslated region of the 35S transcript of the Cauliflower Mosaic Virus (Sanfaçon et al., 1991) |
| Pscw-prp | 4760 | 6198 | sequence including the promoter region of a proline-rich cell wall protein gene of *Gossypium hirsutum* (cotton) |
| gfaEc-1Pb | 6202 | 8031 | coding sequence of the glutamine:fructose-6-phosphate amidotransferase gene of *Escherichia coli* (Frohberg and Essigmann, 2006) |
| tmiR403At-N1 | 8038 | 8063 | sequence including the binding site of microRNA403 of *Arabidopsis thaliana* (Harvey et al., 2011) |
| tmiR403At | 8041 | 8060 | Core binding site of microRNA403 of *Arabidopsis thaliana* |
| 3'histonAt | 8089 | 8749 | sequence including the 3' untranslated region of the histone H4 gene of *Arabidopsis thaliana* (Chabouté et al., 1987) |
| Ph4a748 | 8799 | 9715 | sequence including the promoter region of the histone H4 gene of *Arabidopsis thaliana* (Chabouté et al., 1987) |
| intron1 h3At | 9749 | 10229 | sequence including the first intron of gene II of the histone H3.III variant of *Arabidopsis thaliana* (Chaubet et al., 1992) |
| TPotp C | 10234 | 10605 | coding sequence of the optimized transit peptide, containing sequence of the RuBisCO small subunit genes of *Zea mays* (corn) and *Helianthus annuus* (sunflower) (Lebrun et al., 1996) |
| 2mepsps | 10606 | 11943 | coding sequence of the double-mutant 5-enol-pyruvylshikimate-3-phosphate synthase gene of *Zea mays* (corn) (Lebrun et al., 1997) |
| 3'histon At | 11967 | 12627 | sequence including the 3' untranslated region of the histone H4 gene of *Arabidopsis thaliana* (Chabouté et al., 1987) |
| LB | 12740 | 12764 | Left border repeat from the T-DNA of *Agrobacterium tumefaciens* (Zambryski, 1988) |

TABLE 5 genetic elements of T-DNA of vector pTEA3 comprising recombinant construct containing glutamine:fructose-6-phosphate amidotransferase and chitin synthase both containing a miR408 target site in their 3' UTR - reference is SEQ ID No. 16

| Name | Start | End | Description |
| --- | --- | --- | --- |
| RB | 1 | 25 | Right border repeat from the T-DNA of *Agrobacterium tumefaciens* (Zambryski, 1988) |
| Pscw-prp | 61 | 1499 | sequence including the promoter region of a proline-rich cell wall protein gene of *Gossypium hirsutum* (cotton) |
| RPxylTAt | 1503 | 1607 | coding sequence for the Golgi retention peptide of the beta-1,2-xylosyltransferase gene of *Arabidopsis thaliana* (Pagny et al., 2003) |
| chs2Nc-1Pc | 1608 | 4439 | coding sequence of the chitin synthase 2 gene of *Neurospora crassa* (Din and Yarden, 1994) |
| tmiR408At-N1 | 4452 | 4478 | sequence including the binding site of microRNA408 of *Arabidopsis thaliana* (Harvey et al., 2011) |
| tmiR408At | 4455 | 4475 | Core binding site of microRNA408 of *Arabidopsis thaliana* |
| 3'35S | 4499 | 4735 | sequence including the 3' untranslated region of the 35S transcript of the Cauliflower Mosaic Virus (Sanfaçon et al., 1991) |

TABLE 5-continued genetic elements of T-DNA of vector pTEA3 comprising recombinant construct containing glutamine:fructose-6-phosphate amidotransferase and chitin synthase both containing a miR408 target site in their 3' UTR - reference is SEQ ID No. 16

| Name | Start | End | Description |
|---|---|---|---|
| Pscw-prp | 4773 | 6211 | sequence including the promoter region of a proline-rich cell wall protein gene of *Gossypium hirsutum* (cotton) |
| gfaEc-1Pb | 6215 | 8044 | coding sequence of the glutamine:fructose-6-phosphate amidotransferase gene of *Escherichia coli* (Frohberg and Essigmann, 2006) |
| tmiR408At-N1 | 8057 | 8083 | sequence including the binding site of microRNA408 of *Arabidopsis thaliana* (Harvey et al., 2011) |
| tmiR408At | 8060 | 8080 | Core binding site of microRNA408 of *Arabidopsis thaliana* |
| 3'histonAt | 8105 | 8765 | sequence including the 3' untranslated region of the histone H4 gene of *Arabidopsis thaliana* (Chabouté et al., 1987) |
| Ph4a748 | 8815 | 9731 | sequence including the promoter region of the histone H4 gene of *Arabidopsis thaliana* (Chabouté et al., 1987) |
| intron1 h3At | 9765 | 10245 | sequence including the first intron of gene II of the histone H3.III variant of *Arabidopsis thaliana* (Chaubet et al., 1992) |
| TPotp C | 10250 | 10621 | coding sequence of the optimized transit peptide, containing sequence of the RuBisCO small subunit genes of *Zea mays* (corn) and *Helianthus annuus* (sunflower) (Lebrun et al., 1996) |
| 2mepsps | 10622 | 11959 | coding sequence of the double-mutant 5-enol-pyruvylshikimate-3-phosphate synthase gene of *Zea mays* (corn) (Lebrun et al., 1997) |
| 3'histon At | 11983 | 12643 | sequence including the 3' untranslated region of the histone H4 gene of *Arabidopsis thaliana* (Chabouté et al., 1987) |
| LB | 12756 | 12780 | Left border repeat from the T-DNA of *Agrobacterium tumefaciens* (Zambryski, 1988) |

TABLE 6 genetic elements of T-DNA of vector pTEA6 comprising recombinant construct containing glutamine:fructose-6-phosphate amidotransferase containing a miR403 target site in its 3' UTR and chitin synthase containing a miR408 target site in its 3' UTR - reference is SEQ ID No. 17

| Name | Start | End | Description |
|---|---|---|---|
| RB | 1 | 25 | Right border repeat from the T-DNA of *Agrobacterium tumefaciens* (Zambryski, 1988) |
| Pscw-prp | 61 | 1499 | sequence including the promoter region of a proline-rich cell wall protein gene of *Gossypium hirsutum* (cotton) |
| RPxylTAt | 1503 | 1607 | coding sequence for the Golgi retention peptide of the beta-1,2-xylosyltransferase gene of *Arabidopsis thaliana* (Pagny et al., 2003) |
| chs2Nc-1Pc | 1608 | 4439 | coding sequence of the chitin synthase 2 gene of *Neurospora crassa* (Din and Yarden, 1994) |
| tmiR408At-N1 | 4452 | 4478 | sequence including the binding site of microRNA408 of *Arabidopsis thaliana* (Harvey et al., 2011) |
| tmiR408At | 4455 | 4475 | Core binding site of microRNA408 of *Arabidopsis thaliana* |
| 3'35S | 4499 | 4735 | sequence including the 3' untranslated region of the 35S transcript of the Cauliflower Mosaic Virus (Sanfaçon et al., 1991) |
| Pscw-prp | 4773 | 6211 | sequence including the promoter region of a proline-rich cell wall protein gene of *Gossypium hirsutum* (cotton) |
| gfaEc-1Pb | 6215 | 8044 | coding sequence of the glutamine:fructose-6-phosphate amidotransferase gene of *Escherichia coli* (Frohberg and Essigmann, 2006) |
| tmiR403At-N1 | 8051 | 8076 | sequence including the binding site of microRNA403 of *Arabidopsis thaliana* (Harvey et al., 2011) |
| tmiR403At | 8054 | 8073 | Core binding site of microRNA403 of *Arabidopsis thaliana* |
| 3'histonAt | 8102 | 8762 | sequence including the 3' untranslated region of the histone H4 gene of *Arabidopsis thaliana* (Chabouté et al., 1987) |
| Ph4a748 | 8812 | 9728 | sequence including the promoter region of the histone H4 gene of *Arabidopsis thaliana* (Chabouté et al., 1987) |
| intron1 h3At | 9762 | 10242 | sequence including the first intron of gene II of the histone H3.III variant of *Arabidopsis thaliana* (Chaubet et al., 1992) |

TABLE 6-continued genetic elements of T-DNA of vector pTEA6 comprising recombinant construct containing glutamine:fructose-6-phosphate amidotransferase containing a miR403 target site in its 3' UTR and chitin synthase containing a miR408 target site in its 3' UTR - reference is SEQ ID No. 17

| Name | Start | End | Description |
| --- | --- | --- | --- |
| TPotp C | 10247 | 10618 | coding sequence of the optimized transit peptide, containing sequence of the RuBisCO small subunit genes of *Zea mays* (corn) and *Helianthus annuus* (sunflower) (Lebrun et al., 1996) |
| 2mepsps | 10619 | 11956 | coding sequence of the double-mutant 5-enol-pyruvylshikimate-3-phosphate synthase gene of *Zea mays* (corn) (Lebrun et al., 1997) |
| 3'histon At | 11980 | 12640 | sequence including the 3' untranslated region of the histone H4 gene of *Arabidopsis thaliana* (Chabouté et al., 1987) |
| LB | 12753 | 12777 | Left border repeat from the T-DNA of *Agrobacterium tumefaciens* (Zambryski, 1988) |

TABLE 7 genetic elements of T-DNA of vector pTEA9 comprising recombinant construct containing glutamine:fructose-6-phosphate amidotransferase containing a miR398 target site in its 3' UTR and chitin synthase containing a miR398 target site in its 3' UTR - reference is SEQ ID No. 24

| Name | Start | End | Description |
| --- | --- | --- | --- |
| RB | 1 | 25 | Right border repeat from the T-DNA of *Agrobacterium tumefaciens* (Zambryski, 1988) |
| Pscw-prp | 61 | 1499 | sequence including the promoter region of a proline-rich cell wall protein gene of *Gossypium hirsutum* (cotton) |
| RPxylTAt | 1503 | 1607 | coding sequence for the Golgi retention peptide of the beta-1,2-xylosyltransferase gene of *Arabidopsis thaliana* (Pagny et al., 2003) |
| chs2Nc-1Pc | 1608 | 4439 | coding sequence of the chitin synthase 2 gene of *Neurospora crassa* (Din and Yarden, 1994) |
| tmiR398Gh-N1 | 4446 | 4472 | sequence including the binding site of microRNA398 of *Gossypium hirsutum* |
| tmiR398At | 4449 | 4469 | Core binding site of microRNA398 of *Gossypium hirsutum* |
| 3'35S | 4484 | 4708 | sequence including the 3' untranslated region of the 35S transcript of the Cauliflower Mosaic Virus (Sanfaçon et al., 1991) |
| Pscw-prp | 4759 | 6197 | sequence including the promoter region of a proline-rich cell wall protein gene of *Gossypium hirsutum* (cotton) |
| gfaEc-1Pb | 6201 | 8030 | coding sequence of the glutamine:fructose-6-phosphate amidotransferase gene of *Escherichia coli* (Frohberg and Essigmann, 2006) |
| tmiR398Gh_N1 | 8043 | 8069 | sequence including the binding site microRNA398 of *Gossypium hirsutum* |
| tmiR398Gh | 8046 | 8066 | Core binding site of microRNA398 of *Gossypium hirsutum* |
| 3'histonAt | 8081 | 8741 | sequence including the 3' untranslated region of the histone H4 gene of *Arabidopsis thaliana* (Chabouté et al., 1987) |
| Ph4a748 | 8791 | 9707 | sequence including the promoter region of the histone H4 gene of *Arabidopsis thaliana* (Chabouté et al., 1987) |
| intron1 h3At | 9757 | 10219 | sequence including the first intron of gene II of the histone H3.III variant of *Arabidopsis thaliana* (Chaubet et al., 1992) |
| TPotp C | 10226 | 10597 | coding sequence of the optimized transit peptide, containing sequence of the RuBisCO small subunit genes of *Zea mays* (corn) and *Helianthus annuus* (sunflower) (Lebrun et al., 1996) |
| 2mepsps | 10598 | 11935 | coding sequence of the double-mutant 5-enol-pyruvylshikimate-3-phosphate synthase gene of *Zea mays* (corn) (Lebrun et al., 1997) |
| 3'histon At | 11959 | 12619 | sequence including the 3' untranslated region of the histone H4 gene of *Arabidopsis thaliana* (Chabouté et al., 1987) |
| LB | 12732 | 12756 | Left border repeat from the T-DNA of *Agrobacterium tumefaciens* (Zambryski, 1988) |

TABLE 8 genetic elements of T-DNA of vector pTEA10 comprising recombinant construct containing glutamine:fructose-6-phosphate amidotransferase containing a miRcan1230 target site in its 3' UTR and chitin synthase containing a miRcan1230 target site in its 3' UTR - reference is SEQ ID No. 25

| Name | Start | End | Description |
| --- | --- | --- | --- |
| RB | 1 | 25 | Right border repeat from the T-DNA of *Agrobacterium tumefaciens* (Zambryski, 1988) |
| Pscw-prp | 61 | 1499 | sequence including the promoter region of a proline-rich cell wall protein gene of *Gossypium hirsutum* (cotton) |
| RPxylTAt | 1503 | 1607 | coding sequence for the Golgi retention peptide of the beta-1,2-xylosyltransferase gene of *Arabidopsis thaliana* (Pagny et al., 2003) |
| chs2Nc-1Pc | 1608 | 4439 | coding sequence of the chitin synthase 2 gene of *Neurospora crassa* (Din and Yarden, 1994) |
| tmiRcan1230 Gh-N1 | 4446 | 4479 | sequence including the binding site of microRNAcan1230 of *Gossypium hirsutum* |
| tmiR408At | 4449 | 4476 | Core binding site of microRNAcan1230 of *Gossypium hirsutum* |
| 3'35S | 4491 | 4715 | sequence including the 3' untranslated region of the 35S transcript of the Cauliflower Mosaic Virus (Sanfaçon et al., 1991) |
| Pscw-prp | 4766 | 6204 | sequence including the promoter region of a proline-rich cell wall protein gene of *Gossypium hirsutum* (cotton) |
| gfaEc-1Pb | 6208 | 8037 | coding sequence of the glutamine:fructose-6-phosphate amidotransferase gene of *Escherichia coli* (Frohberg and Essigmann, 2006) |
| tmiRcan1230 Gh-N1 | 8050 | 8083 | sequence including the binding site of microRNAcan1230 of *Gossypium hirsutum* |
| tmiRcan1230 Gh | 8053 | 8080 | Core binding site of microRNAcan1230 of *Gossypium hirsutum* |
| 3'histonAt | 8095 | 8755 | sequence including the 3' untranslated region of the histone H4 gene of *Arabidopsis thaliana* (Chabouté et al., 1987) |
| Ph4a748 | 8805 | 9721 | sequence including the promoter region of the histone H4 gene of *Arabidopsis thaliana* (Chabouté et al., 1987) |
| intron1 h3At | 9771 | 10233 | sequence including the first intron of gene II of the histone H3.III variant of *Arabidopsis thaliana* (Chaubet et al., 1992) |
| TPotp C | 10240 | 10611 | coding sequence of the optimized transit peptide, containing sequence of the RuBisCO small subunit genes of *Zea mays* (corn) and *Helianthus annuus* (sunflower) (Lebrun et al., 1996) |
| 2mepsps | 10612 | 11949 | coding sequence of the double-mutant 5-enol-pyruvylshikimate-3-phosphate synthase gene of *Zea mays* (corn) (Lebrun et al., 1997) |
| 3'histon At | 11973 | 12633 | sequence including the 3' untranslated region of the histone H4 gene of *Arabidopsis thaliana* (Chabouté et al., 1987) |
| LB | 12746 | 12770 | Left border repeat from the T-DNA of *Agrobacterium tumefaciens* (Zambryski, 1988) |

The invention claimed is:

1. A recombinant gene for spatially selective expression in a cotton plant comprising the following operably linked elements:
   (a) a plant-expressible promoter;
   (b) a region encoding an RNA molecule translated into a polypeptide or protein; and
   (c) a heterologous target sequence recognized by an endogenous miRNA, said miRNA being expressed less abundantly in developing fiber cells in said cotton plant compared to non-fiber cells of said cotton plant and said miRNA having a nucleotide sequence selected from the nucleotide sequence of SEQ ID No. 1, SEQ ID No. 2, SEQ ID No. 3, SEQ ID No. 4, SEQ ID No. 20, SEQ ID No.21 or SEQ ID No. 22
   and wherein said target sequence has the nucleotide sequence of SEQ ID No. 5, SEQ ID No. 5 from nucleotide position 4 to nucleotide position 24, SEQ ID No. 6, SEQ ID No. 6 from nucleotide position 4 to nucleotide position 24, SEQ ID No. 7, SEQ ID No. 8, SEQ ID No. 8 from nucleotide position 4 to 24, SEQ ID No. 23, SEQ ID No. 23 from nucleotide position 4 to 24, SEQ ID No. 23 from nucleotide position 11 to 32, or SEQ ID No. 23 from nucleotide position 4 to 32 or a nucleotide sequence which is complementary to the nucleotide sequence of SEQ ID No. 1, SEQ ID No. 2, SEQ ID No. 3, SEQ ID No. 4, SEQ ID No. 20, SEQ ID No. 21 or SEQ ID No. 22 whereby one or more of the following mismatches may occur:
   (i) a mismatch between the nucleotide at the 5' end of said miRNA and the corresponding nucleotide sequence in the target RNA sequence;
   (ii) a mismatch between any one of the nucleotides in position 1 to position 9 of said miRNA and the corresponding nucleotide sequence in the target RNA sequence;
   (iii) three mismatches between any one of the nucleotides in position 12 to position 21 of said miRNA and the corresponding nucleotide sequence in the target RNA sequence provided that there are no more than two consecutive mismatches; and
   (iv) no mismatch is allowed at positions 10 and 11 of the miRNA.

2. The recombinant gene of claim 1, wherein said recombinant gene comprises a 3' untranslated region comprising said target sequence.

3. The recombinant gene of claim 1, wherein said plant expressible promoter is selected from a constitutive promoter, an inducible-promoter, a tissue-specific promoter, a developmentally regulated promoter.

4. The recombinant gene of claim 1, wherein said plant-expressible promoter is a fiber-preferential or fiber-selective promoter.

5. The recombinant gene of claim 1, wherein said miRNA is substantially not expressed in developing fiber cells of said cotton plant but expressed in non-fiber cells.

6. The recombinant gene of claim 1, wherein said RNA encodes
   (a) a polypeptide with N-acetylglucosamine transferase activity, or
   (b) a glutamine:fructose-6-phosphate amidotransferase.

7. The recombinant gene of claim 6 wherein said N-acetylglucosamine transferase is
   (a) a NODC-type N-acetylglucosamine transferase, or
   (b) a chitin synthase.

8. The recombinant gene of claim 6, wherein said N-acetylglucosamine transferase activity comprises a signal anchor sequence selected from the signal anchor sequence of a rat sialyl transferase, the signal anchor sequence of a human galactosyl transferase, the signal anchor sequence of the *Arabidopsis* homologue of the yeast HDEL receptor (AtERD2), the signal anchor sequence of the α-2,6-sialyltransferase, the signal anchor sequence of β1,2-xylosyltransferase from *Arabidopsis thaliana*, the signal anchor sequence of N-acetylglucosamine transferase I from tobacco or the amino acid sequence YYHDL (SEQ ID No. 26) or LKLEI (SEQ ID No. 27).

9. A cotton plant cell comprising the recombinant gene according to claim 1.

10. The cell of claim 9, wherein said cell is a cell capable of developing into a fiber cell.

11. A cotton plant, part, tissue or seed of a cotton plant comprising the cell according to claim 9, or consisting essentially of cells according to claim 9.

12. A method of producing a cotton plant with spatially selective expression of a recombinant gene, comprising the step of:
   (a) introducing the recombinant gene according to claim 1 into at least one cell of said cotton plant;
   (b) optionally, regenerating the cotton plant from said at least one cell comprising said recombinant gene.

13. A method for increasing tissue selective expression in a cotton plant comprising the step of introducing the recombinant gene according to claim 1 into at least one cell of the cotton plant and regenerating a plant from said at least one cell comprising the recombinant gene.

14. A method for producing fibers from a cotton plant comprising the steps of
   (a) growing the plant obtained by the process of claim 12;
   (b) harvesting fibers from said grown plants.

15. Plant fibers comprising the recombinant gene according to claim 1.

* * * * *

```
                          SEQUENCE LISTING

<160> NUMBER OF SEQ ID NOS: 27

<210> SEQ ID NO 1
<211> LENGTH: 23
<212> TYPE: DNA
<213> ORGANISM: Artificial Sequence
<220> FEATURE:
<223> OTHER INFORMATION: nucleotide sequence of microRNA Ghi_miR403

<400> SEQUENCE: 1
ttagattcac gcgcacaaac tcg                                            23

<210> SEQ ID NO 2
<211> LENGTH: 21
<212> TYPE: DNA
<213> ORGANISM: Artificial Sequence
<220> FEATURE:
<223> OTHER INFORMATION: nucleotide sequence of microRNA Ghi_miR408

<400> SEQUENCE: 2
atgcactgcc tcttccctgg c                                              21
```

-continued

```
<210> SEQ ID NO 3
<211> LENGTH: 21
<212> TYPE: DNA
<213> ORGANISM: Artificial Sequence
<220> FEATURE:
<223> OTHER INFORMATION: nucleotide sequence of microRNA Ghi_miRcan1230

<400> SEQUENCE: 3
ttgcatgaca ctactttaaa t                                                 21

<210> SEQ ID NO 4
<211> LENGTH: 21
<212> TYPE: DNA
<213> ORGANISM: Artificial Sequence
<220> FEATURE:
<223> OTHER INFORMATION: nucleotide sequence of microRNA Ghi_miR398

<400> SEQUENCE: 4
tgtgttctca ggtcgcccct g                                                 21

<210> SEQ ID NO 5
<211> LENGTH: 27
<212> TYPE: DNA
<213> ORGANISM: Artificial Sequence
<220> FEATURE:
<223> OTHER INFORMATION: nucleotide sequence of engineered target
      sequence recognized by microRNA Ghi_miR403
<220> FEATURE:
<221> NAME/KEY: misc_feature
<222> LOCATION: (4)..(24)
<223> OTHER INFORMATION: core target sequence for miR403

<400> SEQUENCE: 5
aagggagttt gtgcgtgaat ctaattg                                           27

<210> SEQ ID NO 6
<211> LENGTH: 27
<212> TYPE: DNA
<213> ORGANISM: Artificial Sequence
<220> FEATURE:
<223> OTHER INFORMATION: nucleotide sequence of engineered target
      sequence recognized by microRNA Ghi_miR408
<220> FEATURE:
<221> NAME/KEY: misc_feature
<222> LOCATION: (4)..(24)
<223> OTHER INFORMATION: core target sequence for miR408

<400> SEQUENCE: 6
gacgccggtg aagaggcagt gcaagac                                           27

<210> SEQ ID NO 7
<211> LENGTH: 27
<212> TYPE: DNA
<213> ORGANISM: Artificial Sequence
<220> FEATURE:
<223> OTHER INFORMATION: nucleotide sequence of target sequence
      recognized by microRNA Ghi_miR1230
<220> FEATURE:
<221> NAME/KEY: misc_feature
<222> LOCATION: (4)..(24)
<223> OTHER INFORMATION: core target sequence for miRcan1230

<400> SEQUENCE: 7
agttttaaag tagtgccatg cattttt                                           27

<210> SEQ ID NO 8
<211> LENGTH: 27
<212> TYPE: DNA
```

```
<213> ORGANISM: Artificial Sequence
<220> FEATURE:
<223> OTHER INFORMATION: nucleotide sequence of target sequence
      recognized by microRNA Ghi_miR398
<220> FEATURE:
<221> NAME/KEY: misc_feature
<222> LOCATION: (4)..(24)
<223> OTHER INFORMATION: core target sequence for miR398

<400> SEQUENCE: 8
gccattgggc gacctgggaa cactaga                                              27

<210> SEQ ID NO 9
<211> LENGTH: 164
<212> TYPE: DNA
<213> ORGANISM: Artificial Sequence
<220> FEATURE:
<223> OTHER INFORMATION: nucleotide sequence of pre-microRNA Ghi_miR403
<220> FEATURE:
<221> NAME/KEY: misc_feature
<222> LOCATION: (41)..(62)
<223> OTHER INFORMATION: microRNA* region
<220> FEATURE:
<221> NAME/KEY: misc_feature
<222> LOCATION: (104)..(124)
<223> OTHER INFORMATION: microRNA region

<400> SEQUENCE: 9
acaattttaa aaaaattgaa aaagaagag ccatatttcg agttttgtgc gtgaatctaa            60
taaaactgta atccacacac aaaaaatgtg gatttgtttc atgttagatt cacgcacaaa         120
ctcgtaatct gtctttccat taatttcccc gtcgtttctt catg                          164

<210> SEQ ID NO 10
<211> LENGTH: 160
<212> TYPE: DNA
<213> ORGANISM: Artificial Sequence
<220> FEATURE:
<223> OTHER INFORMATION: nucleotide sequence of pre-microRNA Ghi_miR408
<220> FEATURE:
<221> NAME/KEY: misc_feature
<222> LOCATION: (41)..(58)
<223> OTHER INFORMATION: microRNA* region
<220> FEATURE:
<221> NAME/KEY: misc_feature
<222> LOCATION: (99)..(120)
<223> OTHER INFORMATION: microRNA region

<400> SEQUENCE: 10
tattgagaga gagtgagaaa gatgggagag acagacaaag acagggaaca ggctgagcat           60
ggatggatct accaactgat tctgttgttt ctccgcccat gcactgcctc ttccctggct         120
ctgcctcctc catttttttc ctccctcttt ttttatttaa                               160

<210> SEQ ID NO 11
<211> LENGTH: 146
<212> TYPE: DNA
<213> ORGANISM: Artificial Sequence
<220> FEATURE:
<223> OTHER INFORMATION: nucleotide sequence of pre-microRNA Ghi_miR1230
<220> FEATURE:
<221> NAME/KEY: misc_feature
<222> LOCATION: (41)..(61)
<223> OTHER INFORMATION: microRNA region
<220> FEATURE:
<221> NAME/KEY: misc_feature
<222> LOCATION: (87)..(106)
<223> OTHER INFORMATION: microRNA* region

<400> SEQUENCE: 11
```

```
ttacttctaa acaagcgaac aaaattattt ggcatgtggc tttgcatgac actactttaa      60
attaacatta ttaaaaacaa tgacaattaa agtagtgtcc tgcaaactca caaaccaaat     120
aaaactctct ccaataactc tttata                                          146

<210> SEQ ID NO 12
<211> LENGTH: 152
<212> TYPE: DNA
<213> ORGANISM: Artificial Sequence
<220> FEATURE:
<223> OTHER INFORMATION: nucleotide sequence of pre- microRNA Ghi_miR398
<220> FEATURE:
<221> NAME/KEY: misc_feature
<222> LOCATION: (41)..(61)
<223> OTHER INFORMATION: microRNA* region
<220> FEATURE:
<221> NAME/KEY: misc_feature
<222> LOCATION: (94)..(114)
<223> OTHER INFORMATION: microRNA region

<400> SEQUENCE: 12
cccaatgatt tgagggaacc agaggtggag gaatccgacc gggtcgacct tagaatacat      60
gtgattgttt tcgatttcaa tatggttcgt tcatgtgttc tcaggtcgcc cctgtcggat     120
tttcattcat cattttatcg tatagttatt aa                                   152

<210> SEQ ID NO 13
<211> LENGTH: 19007
<212> TYPE: DNA
<213> ORGANISM: Artificial Sequence
<220> FEATURE:
<223> OTHER INFORMATION: nucleotide sequence of pTBI312

<400> SEQUENCE: 13
aattacaacg gtatatatcc tgccagtact gggcccccctc gagggcgatc gcgcggccgc      60
ttcacggaaa gttgttatat ataagttcag taaataataa tgaaatataa attttaatta     120
tatctagtac tcaataagaa gatggagaaa gttatgttaa ttatagttat aaattattta     180
taaatttaat atatatatat aaagaaaata gttgtataac taataattat ttttacaata     240
ctttatatag ttatatttaa aaaaatttta aaattaaaat actattattt tgttcaatat     300
attaatattt atattattta atttattatt gaatatgaat aaatttttttt tgaaaattat     360 attttttaatt tttagaaatt ttatataact ttccatatat atatttctga tttgtcaatt     420
tcttttgaga tttatctaaa ttgatttgaa ttttttttat ttttaaaaaa taaaataatt     480
ttaaaatttc ttggaatttt atataaattt ttggattttt caaaaaaaat tgagattttt     540 ttctttttttt tcgattttt aaatttattt caggaaaata taaactaact tttctttgct     600
ttgggtataa ttaatattag ataacccaca aattagatca ataggagctt catgtcctaa     660
tcccatttaa ttacttttgt tgtatcatta atttagtcga ccttacatag tagctctatg     720
gggcaaatag ttataaatgt taaattagta tttaaatctt gaagtttttta attttaaagtt     780 cagactatta gtattatatc aaatatttaa gggtaaatat atattctaat atctaagctt     840
gggtcaaggt ttaaattaag tacttaaact tggttttata gttcaaattg atttaaataa     900
ctaagtatta atttgaatta agaagcaaag ttcaagtacc taattagact ataaaaaaaa     960
cttttgctag taaattgaac cttaaagtcg agtttagtta tctaattgga caaaaaaatc    1020
ttaaatacca atttaaaccc taagtcaag tttaggtacc aaagtgtata tttatctaat    1080
atttaaattt gatccaccta atttaaattt ttttggtcca atgcaataag agaattaatt    1140
aatacttaca cacatgatag agatataccc acaacagata cacactacaa aaaacattaa    1200
```

```
aaaatagaaa gatatatttc ctacaaaatt taaaagcatt taatttttta actaacatta   1260
gacaaatgga aatggaaaga cttatttta agtttatgga tgaatctaat ttatctaaac    1320
attgggtttt ttttttttgt gacgaaatat gggtgagaga aggtagtaag ctaagtaggg   1380
gagtaatatc tcaaacaaat aattaaaaaa ctcctttaaa tgtggctata aatacctgaa   1440
accaatcctt ctttcctcaa ctcaaatctt caatctttag atcatctctc caaaaaaata   1500
ccatgagtaa acgaatccg aagattctga agatttttct gtatatgtta cttctcaact    1560
ctctctttct catcatctac ttcgtttttc actcatcgtc gttttcagag tccagaatca   1620
gcaaccggtt atcgagttcc gccacaagga cggtacgagc cttcagaaat cgatgtcatg   1680
ccaggccagg acaccgggga tcgagttacg gaaatgcgag gcgaccgctt ccctcggcac   1740
cagcgccttt acactacaat agcccaagtc gcgcagcgca tcattatcca cggtaccatg   1800
gaggttatgc ggacgacgtg acagttagca tgggaccgga cgacgatcgt acagatatct   1860
ttggccccga aaccgatctc agcgaaacgc gccacctcaa cgacgcatac gggtttcggt   1920
catcccagat caccctcagc gaagatcccc acggcaccca cgcgcgttcc cggtacgacg   1980
acgaagacga tgtgagcacc acttattcct ccaacacggg caccagcgct tcaggtgtcg   2040
acaagttcga gcattacggt cccattccgg aggaaggcaa gcacgagcgg cgcggcgtgc   2100
gaccaccaca gatgtcgagg aaggaagtcc agctcatcaa cggcgaactc gttctcgagt   2160
gcaagattcc gactatattg tattcgtttt tgcccaggag agacgaagtg gagtttacgc   2220
acatgcggta cacagccgtc acttgtgacc ctgatgactt tgttgccagg ggttacaagt   2280
tgcgccagaa tatcggtcgt accgccaggg agacggagct gttcatctgc gtgaccatgt   2340
acaacgagga cgagttcgga ttcacacgga ctatgcacgc agtgatgaag aacatttcgc   2400 attttttgttc ccgaaacaag agtaggacgt ggggagcgga tgggtggcag aagattgtgg   2460
tctgtgtggt ttcggatgga cgagagatca ttcaccccg gaccttggac gccctcgcag    2520
ccatgggcgt ttaccagcac ggtatcgcca agaactttgt caaccagaag gcggtgcagg   2580
cccacgttta cgagtacacg acacaagtgt ctctggacag cgacctcaag ttcaagggcg   2640
ccgagaaggg catcgtgccc tgccagatga ttttttgctt gaaggagaag aaccaaaaga   2700
aactcaactc gcatagatgg ttcttcaacg cctttggcaa agccttgaac ccgaatgtgt   2760
gtatcctcct agacgtcggc acccgccccg gcggcacaag tctctaccat ctctggaaag   2820
ccttcgacac ggattccaac gtggcggggg cctgcgggga aatcaaagcg atgaaggggc   2880
ggtttggcgg gaatttgctc aaccctctgg tggctagtca gaactttgag tacaagatga   2940
gcaatattct ggacaaaccg ttggagtcgg tgtttgggta catcacggtg ttgccgggcg   3000
ccttgtcggc gtatcggtac catgcgctgc agaacgatga gacgggccat gggccgttga   3060
gtcagtattt caagggcgag acgctccatg gcagcacgc ggatgtgttt acggcgaaca    3120
tgtacttggc cgaggaccga attctgtgtt gggagttggt ggccaagagg ggtgagaggt   3180
gggtgttgaa gtatgtgaag gggtgtacgg gtgagacgga tgtgcctgac accgtcccgg   3240
aattcgtctc gcaacgtcgt cgttggctca acggtgcctt cttcgccgcc gtctactccc   3300
tcgtccactt tcgacaaatc tggaaaaccg accacacctt tatgcgcaaa gcccttctcc   3360
acgtcgaatt cctctaccac ctcctgcaac tcctcttcac ctacttctcc ctggccaact   3420
tctacctcgc cttctacttt atcgccgcg gactcgccga tccccacgtc gaccctttta   3480
actcggacgg ccacgtcgcg cgcatcatct tcaacatcct ccgctacgtc tgcgtcctgc   3540
```

```
tgatctgcac acaattcatc ttgtccctcg gcaaccgtcc gcagggtgcc aaaagaatgt    3600
atctcgcatc catgatcatc tacgccgtca tcatggtgta caccaccttc gccaccatct    3660
tcatcgtcgt gcgacaaatc caaccctctc aaaaatccga cgacaagccc gacctcgaac    3720
tcggcaacaa cgtcttcacc aacctgatcg tctccgtggc tagtacccte gggctctact    3780 tcgtcatgtc ctttctctat ctcgacccct ggcacatgtt cacctcggcc atccagtact    3840
ttgtcctgct gccttcctac atctgcacgc tccagatcta cgccttttgc aacacccacg    3900
acgtcacatg gggcaccaaa ggcgacaacg tgatgcgcac cgatctcgga ggcgccattg    3960
gcaagggaag caccgtcgaa ctggaaatgc cttcggacca actcgacatc gactcgggat    4020
acgacgaatg tctacgaaat ctccgggatc gcgtcatggt ccctgccgtt cccgtgtccg    4080
aggaccagct gcagcaggat tactacaagt cggtgcgcac gtacatggtg gtgtcgtgga    4140
tggtggccaa cgcgacgctg gccatggcgg tgtcggaagc gtatggcgat tcggaaattg    4200
gggataattt ttacttgcgg tttatcctgt gggcggtggc ggccctggcg ctgtttagag    4260
cgttggggtc gacgacgttt gcggcgatta atctggtgag tgctctcgtg gagggcaggg    4320
tcaggctgag gttgaatatg aaagggttta ggtggattaa ggagaagtgg ggggatgcgg    4380
atgtgaaggg caagtttgag gggttggggg atcgggcgag ggggttggcg aggcggtgaa    4440
aggagtttgt gcgtgaatct aattggttta acgctagca agcttggaca cgctgaaatc    4500
accagtctct ctctacaaat ctatctctct ctattttctc cataataatg tgtgagtagt    4560
tcccagataa gggaattagg gttcctatag ggtttcgctc atgtgttgag catataagaa    4620
acccttagta tgtatttgta tttgtaaaat acttctatca ataaaatttc taattcctaa    4680
aaccaaaatc cagtactaaa atccagatca tgcatggtac agcacgcgtc ctgcaggccc    4740
gggttaatta agcggccgct tcacggaaag ttgttatata aagttcagt aaataataat    4800 gaaatataaa ttttaattat atctagtact caataagaag atggagaaag ttatgttaat    4860
tatagttata aattatttat aaatttaata tatatata aagaaaatag ttgtataact    4920
aataattatt tttacaatac tttatatagt tatatttaaa aaaattttaa aattaaaata    4980
ctattatttt gttcaatata ttaatattta tattatttaa tttattattg aatatgaata    5040
aatttttttt gaaaattata tttttaattt ttagaaattt tatataactt tccatatata    5100
tatttctgat tgtcaatttt cttttgagat ttatctaaat tgatttgaat tttttttatt    5160
tttaaaaaat aaaataattt taaaatttct tggaattta tataaaattttt tggatttttc    5220 aaaaaaaatt gagatttttt tcttttttt cgatttttta aatttatttc aggaaaatat    5280
aaactaactt ttctttgctt tgggtataat taatattaga taacccacaa attagatcaa    5340
taggagcttc atgtcctaat cccatttaat tacttttgtt gtatcattaa tttagtcgac    5400
cttacatagt agctctatgg ggcaaatagt tataaatgtt aaattagtat ttaaatcttg    5460 aagttttaa tttaaagttc agactattag tattatatca aatatttaag ggtaaatata    5520
tattctaata tctaagcttg ggtcaaggtt taaattaagt acttaaactt ggttttatag    5580
ttcaaattga tttaaataac taagtattaa tttgaattaa gaagcaaagt tcaagtacct    5640
aattagacta taaaaaaaac ttttgctagt aaattgaacc ttaaagtcga gtttagttat    5700
ctaattggac aaaaaaatct taaataccaa tttaaacct aaagtcaagt ttaggtacca    5760
aagtgtatat ttatctaata tttaaatttg atccacctaa tttaaatttt tttggtccaa    5820
tgcaataaga gaattaatta atacttacac acatgataga gatataccca caacagatac    5880
acactacaaa aaacattaaa aaatagaaag atatattcc tacaaaattt aaaagcattt    5940
```

```
aatttttaa ctaacattag acaaatggaa atggaaagac ttattttaa gtttatggat    6000 gaatctaatt tatctaaaca ttgggttttt ttttttgtg acgaaatatg ggtgagagaa    6060
ggtagtaagc taagtagggg agtaatatct caaacaaata attaaaaaac tcctttaaat    6120
gtggctataa atacctgaaa ccaatccttc tttcctcaac tcaaatcttc aatctttaga    6180
tcatctctcc aaaaaaatac catgtgcgga attgttggtg ctatcgccca agagacgtt     6240 gctgagattt tgttagaggg tctgcgaagg ctagagtata gaggatatga ctccgctggt    6300
ctggctgtcg ttgatgctga gggtcatatg acaaggctaa aaggttagg aaaggttcag     6360 atgcttgctc aggcagctga ggaacatcca ttgcatggag gtactggtat tgcacatacc    6420
aggtgggcta ctcatgggga gccatcagaa gttaatgctc atccacatgt gagtgagcat    6480
atcgttgtag ttcacaatgg gataattgaa aaccacgaac cattgaggga agagttaaag    6540
gcaagaggat atacttttgt gagtgagact gacactgagg ttattgcaca tttagtgaac    6600
tgggaactca aacaggggg cacattgcgt gaggctgtgt taagagctat tcctcaactt     6660
agaggtgcat acggtactgt tattatggat tcaagacacc cagatactct ccttgcagct    6720
agatcaggta gtcccttggt cataggactt ggaatgggtg aaaattttat cgctagcgac    6780
caattggcct tattgccagt tacaagacga tttattttcc ttgaagaggg cgatattgct    6840
gagattacta gaaggtctgt gaacatcttt gataagactg gcgctgaggt taaacgtcag    6900
gatatcgagt ctaaccttca atacgatgct ggtgataaag gaatttacag gcattatatg    6960
caaaaggaaa tttatgaaca accaaatgct atcaaaaaca cacttactgg ccgtatttct    7020
catggacagg tcgatttaag cgagcttggt cctaatgcag acgaactgct atcaaaagtt    7080
gagcacatac agatactggc atgcggaact agttataatt caggaatggt gtctagatac    7140
tggttcgaaa gcttggcagg tataccttgt gatgtagaga tcgcttctga gtttaggtat    7200
agaaagtctg ctgtgcgtag aaattcatta atgattacat tatctcaatc cggagaaaca    7260
gcagatacac tggctggatt gaggctttct aaggaactcg gatatctggg ttcacttgct    7320
atttgtaatg taccaggttc ctcattggtt cgtgaatcag atctagcact tatgacaaat    7380
gcaggaactg aaataggtgt ggcaagtacc aaggctttca caacccaact gaccgtactt    7440
ttaatgttgg tagcaaaact cagtcgatta aaggggctag atgcatctat cgaacatgat    7500
attgttcacg ggcttcaagc tctcccttca agaattgaac aaatgctttc acaagataag    7560
agaatagagg cattggctga agatttttcc gacaaacatc acgcattgtt tcttggacgt    7620
ggcgatcaat atccaattgc attggaagga gctttgaagt tgaaagaaat aagttacatt    7680
cacgcagaag catatgcagc tggagaactc aagcatggtc ctttggcact catcgacgct    7740
gacatgcccg tgatcgtagt ggctcctaat aacgaactgc tcgaaaagct taaatcaaat    7800
atcgaagagg ttcgagctag aggaggtcag ctttacgttt tcgctgaaca agatgctgga    7860
ttcgtgtcaa gcgataatat gcatataatt gaaatgcctc acgttgaaga agtgattgca    7920
cctatatttt atacagtccc attgcaactt ctagcttacc atgttgcact tattaaagga    7980
actgatgttg atcagcctag aaacctagca aatctgtaa cagtcgaata aacgcgtaag    8040
gagtttgtgc gtgaatctaa ttgaggcctg tttaaacggc gcgccccga tccgcgtttg     8100 tgttttctgg gtttctcact taagcgtctg cgttttactt ttgtattggg tttggcgttt    8160
agtagtttgc ggtagcgttc ttgttatgtg taattacgct ttttcttctt gcttcagcag    8220
tttcggttga aatataaatc gaatcaagtt tcactttatc agcgttgttt taaattttgg    8280
```

```
cattaaattg gtgaaaattg cttcaatttt gtatctaaat agaagagaca acatgaaatt    8340
cgacttttga cctcaaatct tcgaacattt atttcctgat ttcacgatgg atgaggataa    8400
cgaaagggcg gttcctatgt ccgggaaagt tcccgtagaa gacaatgagc aaagctactg    8460
aaacgcggac acgacgtcgc attggtacgg atatgagtta aaccgactca attcctttat    8520
taagacataa accgattttg gttaaagtgt aacagtgagc tgatataaaa ccgaaacaaa    8580
ccggtacaag tttgattgag caacttgatg acaaacttca gaattttggt tattgaatga    8640
aaatcatagt ctaatcgtaa aaaatgtaca gaagaaaagc tagagcagaa caaagattct    8700
atattctggt tccaatttat catcgcttta acgtccctca gatttgatcg gggaattcga    8760
tatcattacc ctgttatccc taaagcttat taatgtttgt cgaggagaaa tatgagtcga    8820
ggcatggata cactaagttc ccctgaagtg agcatgatct ttgatgctga gatgattccc    8880
agagcaagat agtttgtgct gcaagtgaca caattgtaat gaaaccacca ctcaacgaat    8940
ttacttgtgg ctttgacatg tcgtgtgctc tgtttgtatt tgtgagtgcc ggttggtaat    9000
tattttgtt aatgtgattt taaaacctct tatgtaaata gttactttat ctattgaagt    9060
gtgttcttgt ggtctatagt ttctcaaagg gaaattaaaa tgttgacatc ccatttacaa    9120
ttgataactt ggtatacaca aactttgtaa atttggtgat atttatggtc gaaagaaggc    9180
aatacccatt gtatgttcca atatcaatat caatacgata acttgataat actaacatat    9240
gattgtcatt gttttccag tatcaatata cattaagcta ctacaaaatt agtataaatc    9300
actatattat aaatcttttt cggttgtaac ttgtaattcg tgggttttta aaataaaagc    9360
atgtgaaaat tttcaaataa tgtgatggcg caattttatt ttccgagttc caaaatattg    9420
ccgcttcatt accctaattt gtggcgccac atgtaaaaca aaagacgatt cttagtggct    9480
atcactgcca tcacgcggat cactaatatg aaccgtcgat taaaacagat cgacggttta    9540
tacatcattt tattgtacac acggatcgat atctcagccg ttagatttaa tatgcgatct    9600
gattgctcaa aaaatagact ctccgtcttt gcctataaaa acaatttcac atctttctca    9660
cccaaatcta ctcttaaccg ttcttcttct tctacagaca tcaatttctc tcgactctag    9720
aggatccaag cttatcgatt tcgaacccct caggcgaaga acaggtatga tttgtttgta    9780
attagatcag gggtttaggt cttttccatta cttttttaatg ttttttctgt tactgtctcc    9840
gcgatctgat tttacgacaa tagagtttcg ggttttgtcc cattccagtt tgaaaataaa    9900
ggtccgtctt ttaagtttgc tggatcgata aacctgtgaa gattgagtct agtcgattta    9960
ttggatgatc cattcttcat cgttttttttc ttgcttcgaa gttctgtata accagatttg   10020
tctgtgtgcg attgtcatta cctagccgtg tatcgagaac tagggttttc gagtcaattt   10080
tgccccttt ggttatatct ggttcgataa cgattcatct ggattagggt tttaagtggt   10140
gacgtttagt attccaattt cttcaaaatt tagttatgga taatgaaaat ccccaattga   10200
ctgttcaatt tcttgttaaa tgcgcagatc acaatggctt cgatctcctc ctcagtcgcg   10260
accgttagcc ggaccgcccc tgctcaggcc aacatggtgg ctccgttcac cggccttaag   10320
tccaacgccg ccttccccac caccaagaag gctaacgact tctccaccct tcccagcaac   10380
ggtggaagag ttcaatgtat gcaggtgtgg ccggcctacg gcaacaagaa gttcgagacg   10440
ctgtcgtacc tgccgccgct gtctatggcg cccaccgtga tgatggcctc gtcggccacc   10500
gccgtcgctc cgttccaggg gctcaagtcc accgccagcc tccccgtcgc ccgccgctcc   10560
tccagaagcc tcggcaacgt cagcaacggc ggaaggatcc ggtgcatggc cggcgccgag   10620
gagatcgtgc tgcagcccat caaggagatc tccggcaccg tcaagctgcc ggggtccaag   10680
```

```
tcgctttcca accggatcct cctactcgcc gccctgtccg aggggacaac agtggttgat    10740
aacctgctga acagtgagga tgtccactac atgctcgggg ccttgaggac tcttggtctc    10800
tctgtcgaag cggacaaagc tgccaaaaga gctgtagttg ttggctgtgg tggaaagttc    10860
ccagttgagg atgctaaaga ggaagtgcag ctcttcttgg ggaatgctgg aatcgcaatg    10920
cggtccttga cagcagctgt tactgctgct ggtggaaatg caacttacgt gcttgatgga    10980
gtaccaagaa tgagggagag acccattggc gacttggttg tcggattgaa gcagcttggt    11040
gcagatgttg attgtttcct tggcactgac tgcccacctg ttcgtgtcaa tggaatcgga    11100
gggctacctg gtggcaaggt caagctgtct ggctccatca gcagtcagta cttgagtgcc    11160
ttgctgatgg ctgctccttt ggctcttggg gatgtggaga ttgaaatcat tgataaatta    11220
atctccattc cgtacgtcga aatgacattg agattgatgg agcgttttgg tgtgaaagca    11280
gagcattctg atagctggga cagattctac attaagggag gtcaaaaata caagtcccct    11340
aaaaatgcct atgttgaagg tgatgcctca agcgcaagct atttcttggc tggtgctgca    11400
attactggag ggactgtgac tgtggaaggt tgtggcacca ccagtttgca gggtgatgtg    11460
aagtttgctg aggtactgga gatgatggga gcgaaggtta catggaccga gactagcgta    11520
actgttactg gcccaccgcg ggagccattt gggaggaaac acctcaaggc gattgatgtc    11580
aacatgaaca agatgcctga tgtcgccatg actcttgctg tggttgccct ctttgccgat    11640
ggcccgacag ccatcagaga cgtggcttcc tggagagtaa aggagaccga gaggatggtt    11700
gcgatccgga cggagctaac caagctggga gcatctgttg aggaagggcc ggactactgc    11760
atcatcacgc cgccggagaa gctgaacgtg acggcgatcg acacgtacga cgaccacagg    11820
atggcgatgg ctttctccct tgccgcctgt gccgaggtcc ccgtcaccat ccgggacccgt   11880
gggtgcaccc ggaagacctt ccccgactac ttcgatgtgc tgagcacttt cgtcaagaat    11940
taagctctag aactagtgga tcccccgatc cgcgtttgtg ttttctgggt ttctcactta    12000
agcgtctgcg ttttactttt gtattgggtt tggcgtttag tagtttgcgg tagcgttctt    12060
gttatgtgta attacgcttt ttcttcttgc ttcagcagtt tcggttgaaa tataaatcga    12120
atcaagtttc actttatcag cgttgtttta aattttggca ttaaattggt gaaaattgct    12180
tcaattttgt atctaaatag aagagacaac atgaaattcg acttttgacc tcaaatcttc    12240
gaacatttat ttcctgattt cacgatggat gaggataacg aaagggcggt tcctatgtcc    12300
gggaaagttc ccgtagaaga caatgagcaa agctactgaa acgcggacac gacgtcgcat    12360
tggtacggat atgagttaaa ccgactcaat tcctttatta agcataaaac cgattttggt    12420
taaagtgtaa cagtgagctg atataaaacc gaaacaaacc ggtacaagtt tgattgagca    12480
acttgatgac aaacttcaga atttcggtta ttgaatgaaa atcatagtct aatcgtaaaa    12540
aatgtacaga agaaaagcta gagcagaaca aagattctat attctggttc caatttatca    12600
tcgctttaac gtccctcaga tttgatcggg aaaccaaaac gtcgtgagac agtttggtta    12660
actataacgg tcctaaggta gcgatcgagg cattacggca ttacggcact cgcgagggtc    12720
cgaattcgag catggagcca tttacaattg aatatatcct gccgccgctg ccgctttgca    12780
cccggtggag cttgcatgtt ggtttctacg cagaactgag ccggttaggc agataatttc    12840
cattgagaac tgagccatgt gcaccttccc cccaacacgg tgagcgacgg ggcaacggag    12900
tgatccacat gggactttta aacatcatcc gtcggatggc gttgcgagag aagcagtcga    12960
tccgtgagat cagccgacgc accgggcagg cgcgcaacac gatcgcaaag tatttgaacg    13020
```

```
caggtacaat cgagccgacg ttcacggtac cggaacgacc aagcaagcta gcttagtaaa    13080
gccctcgcta gattttaatg cggatgttgc gattacttcg ccaactattg cgataacaag    13140
aaaaagccag ccttctatga tatatctccc aatttgtgta gggcttatta tgcacgctta    13200
aaaataataa aagcagactt gacctgatag tttggctgtg agcaattatg tgcttagtgc    13260
atctaacgct tgagttaagc cgcgccgcga agcggcgtcg gcttgaacga attgttagac    13320
attatttgcc gactaccttg gtgatctcgc cttcacgta gtggacaaat tcttccaact    13380
gatctgcgcg cgaggccaag cgatcttctt cttgtccaag ataagcctgt ctagcttcaa    13440
gtatgacggg ctgatactgg gccggcaggc gctccattgc ccagtcggca gcgacatcct    13500
tcggcgcgat tttgccggtt actgcgctgt accaaatgcg ggacaacgta agcactacat    13560
ttcgctcatc gccagcccag tcgggcgcg agttccatag cgttaaggtt tcatttagcg    13620
cctcaaatag atcctgttca ggaaccggat caaagagttc ctccgccgct ggacctacca    13680
aggcaacgct atgttctctt gcttttgtca gcaagatagc cagatcaatg tcgatcgtgg    13740
ctggctcgaa gatacctgca agaatgtcat tgcgctgcca ttctccaaat tgcagttcgc    13800
gcttagctgg ataacgccac ggaatgatgt cgtcgtgcac aacaatggtg acttctacag    13860
cgcggagaat ctcgctctct ccaggggaag ccgaagtttc caaaaggtcg ttgatcaaag    13920
ctcgccgcgt tgtttcatca agccttacgg tcaccgtaac cagcaaatca atatcactgt    13980
gtggcttcag gccgccatcc actgcggagc cgtacaaatg tacggccagc aacgtcggtt    14040
cgagatggcg ctcgatgacg ccaactaccet ctgatagttg agtcgatact tcggcgatca    14100
ccgcttccct catgatgttt aactttgttt tagggcgact gccctgctgc gtaacatcgt    14160
tgctgctcca taacatcaaa catcgaccca cggcgtaacg cgcttgctgc ttggatgccc    14220
gaggcataga ctgtaccccca aaaaacagt cataacaagc catgaaaacc gccactgcgc    14280
cgttaccacc gctgcgttcg gtcaaggttc tggaccagtt gcgtgagcgc atacgctact    14340
tgcattacag cttacgaacc gaacaggctt atgtccactg ggttcgtgcc ttcatccgtt    14400
tccacggtgt gcgtcacccg gcaaccttgg gcagcagcga agtcgaggca tttctgtcct    14460
ggctggcgaa cgagcgcaag gtttcggtct ccacgcatcg tcaggcattg gcggccttgc    14520
tgttcttcta cggcaagtgc tgtgcacgga tctgccctgg cttcaggaga tcggaagacc    14580
tcggccgtcc gggcgcttgc cggtggtgct gaccccggat gaagtctcta gagctctaga    14640
gggttcgcat cctcggtttt ctggaaggcg agcatcgttt gttcgcccag cttctgtatg    14700
gaacgggcat gcggatcagt gagggtttgc aactgcgggt caaggatctg gatttcgatc    14760
acggcacgat catcgtgcgg gagggcaagg gctccaagga tcgggccttg atgttacccg    14820
agagcttggc acccagcctg cgcgagcagg gatcgatacc gtgcggctgc atgaaatcct    14880
ggccggtttg tctgatgcca agctggcggc ctggccggcc agcttggccg ctgaagaaac    14940
cgagcgccgc cgtctaaaaa ggtgatgtgt atttgagtaa aacagcttgc gtcatgcggt    15000
cgctgcgtat atgatgcgat gagtaaataa acaaatacgc aaggggaacg catgaaggtt    15060
atcgctgtac ttaaccagaa aggcgggtca ggcaagacga ccatcgcaac ccatctagcc    15120
cgcgccctgc aactcgccgg ggccgatgtt ctgttagtcg attccgatcc ccagggcagt    15180
gcccgcgatt gggcggccgt gcgggaagat caaccgctaa ccgttgtcgg catcgaccgc    15240
ccgacgattg accgcgacgt gaaggccatc ggccggcgcg acttcgtagt gatcgacgga    15300 gcgcccagg cggcggactt ggctgtgtcc gcgatcaagg cagccgactt cgtgctgatt    15360
ccggtgcagc caagcccta cgacatatgg gccaccgccg acctggtgga gctggttaag    15420
```

```
cagcgcattg aggtcacgga tggaaggcta caagcggcct ttgtcgtgtc gcgggcgatc    15480
aaaggcacgc gcatcggcgg tgaggttgcc gaggcgctgg ccgggtacga gctgcccatt    15540
cttgagtccc gtatcacgca gcgcgtgagc tacccaggca ctgccgccgc cggcacaacc    15600
gttcttgaat cagaacccga gggcgacgct gcccgcgagg tccaggcgct ggccgctgaa    15660
attaaatcaa aactcatttg agttaatgag gtaaagagaa aatgagcaaa agcacaaaca    15720
cgctaagtgc cggccgtccg agcgcacgca gcagcaaggc tgcaacgttg ccagcctgg     15780 cagacacgcc agccatgaag cgggtcaact ttcagttgcc ggcggaggat cacaccaagc    15840
tgaagatgta cgccggtacgc caaggcaaga ccattaccga gctgctatct gaatacatcg   15900
cgcagctacc agagtaaatg agcaaatgaa taatgagta gatgaatttt agcggctaaa     15960
ggaggcggca tggaaaatca agaacaacca ggcaccgacg ccgtggaatg ccccatgtgt    16020
ggaggaacgg gcggttggcc aggcgtaagc ggctgggttg tctgccggcc ctgcaatggc    16080
actggaaccc ccaagcccga ggaatcggcg tgacggtcgc aaaccatccg gcccggtaca    16140
aatcggcgcg cgctgggtg atgacctggt ggagaagttg aaggccgcgc aggccgccca     16200
gcggcaacgc atcgaggcag aagcacgccc cggtgaatcg tggcaagcgg ccgctgatcg    16260
aatccgcaaa gaatcccggc aaccgccggc agccggtgcg ccgtcgatta ggaagccgcc    16320
caagggcgac gagcaaccag atttttttcgt tccgatgctc tatgacgtgg gcacccgcga   16380
tagtcgcagc atcatggacg tggccgtttt ccgtctgtcg aagcgtgacc gacgagctgg    16440
cgaggtgatc cgctacgagc ttccagacgg gcacgtagag gtttccgcag ggccggccgg    16500
catggccagt gtgtgggatt acgacctggt actgatggcg gtttcccatc taaccgaatc    16560
catgaaccga tacgggaag ggaagggaga caagcccggc cgcgtgttcc gtccacacgt     16620
tgcggacgta ctcaagttct gccggcgagc cgatggcgga aagcagaaag acgacctggt    16680
agaaacctgc attcggttaa acaccacgca cgttgccatg cagcgtacga agaaggccaa    16740
gaacggccgc ctggtgacgg tatccgaggg tgaagccttg attagccgct acaagatcgt    16800
aaagagcgaa accgggcggc cggagtacat cgagatcgag ctagctgatt ggatgtaccg    16860
cgagatcaca gaaggcaaga acccggacgt gctgacggtt caccccgatt actttttgat    16920
cgatcccggc atcggccgtt ttctctaccg cctggcacgc cgcgccgcag gcaaggcaga    16980
agccagatgg ttgttcaaga cgatctacga acgcagtggc agcgccggag agttcaagaa    17040
gttctgtttc accgtgcgca agctgatcgg gtcaaatgac ctgccggagt acgatttgaa    17100
ggaggaggcg gggcaggctg gcccgatcct agtcatgcgc taccgcaacc tgatcgaggg    17160
cgaagcatcc gccggttcct aatgtacgga gcagatgcta gggcaaattg ccctagcagg    17220
ggaaaaaggt cgaaaggtc tctttcctgt ggatagcacg tacattggga acccaaagcc     17280
gtacattggg aaccggaacc cgtacattgg gaacccaaag ccgtacattg ggaaccggtc    17340
acacatgtaa gtgactgata taaagagaaa aaaggcgat ttttccgcct aaaactcttt     17400
aaaacttatt aaaactctta aaacccgcct ggcctgtgca taactgtctg gccagcgcac    17460
agccgaagag ctgcaaaaag cgcctaccct tcggtcgctg cgctccctac gccccgccgc    17520
ttcgcgtcgg cctatcgcgg ccgctggccg ctcaaaaatg gctggcctac ggccaggcaa    17580
tctaccaggg cgcggacaag ccgcgccgtc gccactcgac cgccggcgcc cacatcaagg    17640
caccctgcct cgcgcgtttc ggtgatgacg gtgaaaacct ctgacacatg cagctcccgg    17700
agacggtcac agcttgtctg taagcggatg ccggagcag acaagcccgt cagggcgcgt     17760
```

```
cagcgggtgt tggcgggtgt cggggcgcag ccatgaccca gtcacgtagc gatagcggag    17820
tgtatactgg cttaactatg cggcatcaga gcagattgta ctgagagtgc accatatgcg    17880
gtgtgaaata ccgcacagat gcgtaaggag aaaataccgc atcaggcgct cttccgcttc    17940
ctcgctcact gactcgctgc gctcggtcgt tcggctgcgg cgagcggtat cagctcactc    18000
aaaggcggta atacggttat ccacagaatc aggggataac gcaggaaaga acatgtgagc    18060
aaaaggccag caaaaggcca ggaaccgtaa aaaggccgcg ttgctggcgt ttttccatag    18120
gctccgcccc cctgacgagc atcacaaaaa tcgacgctca agtcagaggt ggcgaaaccc    18180
gacaggacta taaagatacc aggcgtttcc ccctggaagc tccctcgtgc gctctcctgt    18240
tccgaccctg ccgcttaccg gatacctgtc cgcctttctc ccttcgggaa gcgtggcgct    18300
ttctcatagc tcacgctgta ggtatctcag ttcggtgtag tcgttcgct ccaagctggg     18360 ctgtgtgcac gaaccccccg ttcagcccga ccgctgcgcc ttatccggta actatcgtct    18420
tgagtccaac ccggtaagac acgacttatc gccactggca gcagccactg gtaacaggat    18480
tagcagagcg aggtatgtag gcggtgctac agagttcttg aagtggtggc ctaactacgg    18540
ctacactaga aggacagtat ttggtatctg cgctctgctg aagccagtta ccttcggaaa    18600
aagagttggt agctcttgat ccggcaaaca accaccgct ggtagcggtg ttttttttgt      18660
ttgcaagcag cagattacgc gcagaaaaaa aggatctcaa gaagatccgg aaaacgcaag    18720
cgcaaagaga aagcaggtag cttgcagtgg gcttacatgg cgatagctag actgggcggt    18780
tttatggaca gcaagcgaac cggaattgcc agattcgaag ctcggtcccg tgggtgttct    18840
gtcgtctcgt tgtacaacga atccattcc cattccgcgc tcaagatggc ttcccctcgg     18900
cagttcatca gggctaaatc aatctagccg acttgtccgg tgaaatgggc tgcactccaa    18960
cagaaacaat caaacaaaca tacacagcga cttattcaca cgcgaca                  19007

<210> SEQ ID NO 14
<211> LENGTH: 14339
<212> TYPE: DNA
<213> ORGANISM: Artificial Sequence
<220> FEATURE:
<223> OTHER INFORMATION: nucleotide sequence of pTEA1_v2

<400> SEQUENCE: 14
cgcgtaggcc tgacgccggt gaagaggcag tgcaagacca cgtgaaacgg cgcgccccg       60 atccgcgttt gtgttttctg ggtttctcac ttaagcgtct gcgttttact tttgtattgg     120
gtttggcgtt tagtagtttg cggtagcgtt cttgttatgt gtaattacgc ttttttcttct   180 tgcttcagca gtttcggttg aaatataaat cgaatcaagt ttcactttat cagcgttgtt    240
ttaaattttg gcattaaatt ggtgaaaatt gcttcaattt tgtatctaaa tagaagagac    300
aacatgaaat tcgactttttg acctcaaatc ttcgaacatt tatttcctga tttcacgatg    360
gatgaggata cgaaagggc ggttcctatg tccgggaaag ttcccgtaga agacaatgag     420
caaagctact gaaacgcgga cacgacgtcg cattggtacg gatatgagtt aaaccgactc    480 aattcccttta ttaagacata aaccgatttt ggttaaagtg taacagtgag ctgatataaa   540
accgaaacaa accggtacaa gtttgattga gcaacttgat gacaaacttc agaattttgg    600
ttattgaatg aaaatcatag tctaatcgta aaaaatgtac agaagaaaag ctagagcaga    660
acaaagattc tatattctgg ttccaattta tcatcgcttt aacgtccctc agatttgatc    720
ggggaattcg atatcattac cctgttatcc ctaaagctta ttaatgtttg tcgaggagaa    780
atatgagtcg aggcatggat acactaagtt ccctgaagt gagcatgatc tttgatgctg    840
```

```
agatgattcc cagagcaaga tagtttgtgc tgcaagtgac acaattgtaa tgaaaccacc      900
actcaacgaa tttacttgtg gctttgacat gtcgtgtgct ctgtttgtat ttgtgagtgc      960
cggttggtaa ttattttgt taatgtgatt ttaaaacctc ttatgtaaat agttactta      1020
tctattgaag tgtgttcttg tggtctatag tttctcaaag ggaaattaaa atgttgacat     1080
cccatttaca attgataact tggtatacac aaactttgta aatttggtga tatttatggt     1140
cgaaagaagg caatacccat tgtatgttcc aatatcaata tcaatacgat aacttgataa     1200
tactaacata tgattgtcat tgtttttcca gtatcaatat acattaagct actacaaaat     1260
tagtataaat cactatatta taaatctttt tcggttgtaa cttgtaattc gtgggttttt     1320
aaaataaaag catgtgaaaa ttttcaaata atgtgatggc gcaatttat tttccgagtt      1380
ccaaaatatt gccgcttcat taccctaatt tgtggcgcca catgtaaaac aaaagacgat     1440
tcttagtggc tatcactgcc atcacgcgga tcactaatat gaaccgtcga ttaaaacaga     1500
tcgacggttt atacatcatt ttattgtaca cacggatcga tatctcagcc gttagattta     1560
atatgcgatc tgattgctca aaaaatagac tctccgtctt tgcctataaa aacaatttca     1620
catctttctc acccaaatct actcttaacc gttcttcttc ttctacagac atcaatttct     1680
ctcgactcta gaggatccaa gcttatcgat ttcgaacccc tcaggcgaag aacaggtatg     1740
atttgtttgt aattagatca ggggtttagg tcttttccatt acttttttaat gttttttctg    1800
ttactgtctc cgcgatctga ttttacgaca atagagtttc gggttttgtc ccattccagt     1860
ttgaaaataa aggtccgtct tttaagtttg ctggatcgat aaacctgtga agattgagtc     1920
tagtcgattt attggatgat ccattcttca tcgttttttt cttgcttcga agttctgtat     1980
aaccagatt gtctgtgtgc gattgtcatt acctagccgt gtatcgagaa ctagggtttt     2040
cgagtcaatt ttgccccttt tggttatatc tggttcgata acgattcatc tggattaggg     2100
ttttaagtgg tgacgtttag tattccaatt tcttcaaaat ttagttatgg ataatgaaaa     2160
tccccaattg actgttcaat ttcttgttaa atgcgcagat cacaatggct tcgatctcct     2220
cctcagtcgc gaccgttagc cggaccgccc ctgctcaggc caacatggtg gctccgttca     2280
ccggccttaa gtccaacgcc gccttcccca ccaccaagaa ggctaacgac ttctccaccc     2340
ttcccagcaa cggtggaaga gttcaatgta tgcaggtgtg gccggcctac ggcaacaaga     2400
agttcgagac gctgtcgtac ctgccgccgc tgtctatggc gccccaccgtg atgatggcct   2460
cgtcggccac cgccgtcgct ccgttccagg ggctcaagtc caccgccagc ctccccgtcg     2520
cccgccgctc ctccagaagc ctcggcaacg tcagcaacgg cggaaggatc cggtgcatgg     2580
ccggcgccga ggagatcgtg ctgcagccca tcaaggagat ctccggcacc gtcaagctgc     2640
cggggtccaa gtcgctttcc aaccggatcc tcctactcgc cgccctgtcc gagggaacaa     2700
cagtggttga taacctgctg aacagtgagg atgtccacta catgctcggg gccttgagga     2760
ctcttggtct ctctgtcgaa gcggacaaag ctgccaaaag agctgtagtt gttggctgtg     2820
gtggaaagtt cccagttgag gatgctaaag aggaagtgca gctcttcttg gggaatgctg     2880
gaatcgcaat gcggtccttg acagcagctg ttactgctgc tggtggaaat gcaacttacg     2940
tgcttgatgg agtaccaaga atgagggaga gacccattgg cgacttggtt gtcggattga     3000
agcagcttgg tgcagatgtt gattgttttcc ttggcactga ctgcccacct gttcgtgtca     3060
atggaatcgg agggctacct ggtggcaagg tcaagctgtc tggctccatc agcagtcagt    3120
acttgagtgc cttgctgatg gctgctccct tggctcttgg ggatgtggag attgaaatca     3180
```

-continued

```
ttgataaatt aatctccatt ccgtacgtcg aaatgacatt gagattgatg gagcgttttg    3240
gtgtgaaagc agagcattct gatagctggg acagattcta cattaaggga ggtcaaaaat    3300
acaagtcccc taaaaatgcc tatgttgaag gtgatgcctc aagcgcaagc tatttcttgg    3360
ctggtgctgc aattactgga gggactgtga ctgtggaagg ttgtggcacc accagtttgc    3420
agggtgatgt gaagtttgct gaggtactgg agatgatggg agcgaaggtt acatggaccg    3480
agactagcgt aactgttact ggcccaccgc gggagccatt tgggaggaaa cacctcaagg    3540
cgattgatgt caacatgaac aagatgcctg atgtcgccat gactcttgct gtggttgccc    3600
tctttgccga tggcccgaca gccatcagag acgtggcttc ctggagagta aaggagaccg    3660
agaggatggt tgcgatccgg acggagctaa ccaagctggg agcatctgtt gaggaagggc    3720
cggactactg catcatcacg ccgccggaga agctgaacgt gacggcgatc gacacgtacg    3780
acgaccacag gatggcgatg gctttctccc ttgccgcctg tgccgaggtc cccgtcacca    3840
tccgggaccc tgggtgcacc cggaagacct tccccgacta cttcgatgtg ctgagcactt    3900
tcgtcaagaa ttaagctcta gaactagtgg atcccccgat ccgcgtttgt gttttctggg    3960
tttctcactt aagcgtctgc gttttacttt tgtattgggt ttggcgttta gtagtttgcg    4020
gtagcgttct tgttatgtgt aattacgctt tttcttcttg cttcagcagt ttcggttgaa    4080
atataaatcg aatcaagttt cactttatca gcgttgtttt aaattttggc attaaattgg    4140
tgaaaattgc ttcaattttg tatctaaata gaagagacaa catgaaattc gacttttgac    4200
ctcaaatctt cgaacattta tttcctgatt tcacgatgga tgaggataac gaaagggcgg    4260
ttcctatgtc cgggaaagtt cccgtagaag acaatgagca agctactga aacgcggaca    4320
cgacgtcgca ttggtacgga tatgagttaa accgactcaa ttccttatt aagcataaa    4380
ccgattttgg ttaaagtgta acagtgagct gatataaaac cgaaacaaac cggtacaagt    4440
ttgattgagc aacttgatga caaacttcag aattttggtt attgaatgaa aatcatagtc    4500
taatcgtaaa aaatgtacag aagaaaagct agagcagaac aaagattcta tattctggtt    4560
ccaatttatc atcgctttaa cgtccctcag atttgatcgg gaaaccaaaa cgtcgtgaga    4620
cagtttggtt aactataacg gtcctaaggt agcgatcgag gcattacggc attacggcac    4680
tcgcgagggt ccgaattcga gcatggagcc atttacaatt gaatatatcc tgccgccgct    4740
gccgctttgc acccgtggga gcttgcatgt tggtttctac gcagaactga gccgttaggg    4800
cagataattt ccattgagaa ctgagccatg tgcaccttcc ccccaacacg gtgagcgacg    4860
gggcaacgga gtgatccaca tgggactttt aaacatcatc cgtcggatgg cgttgcgaga    4920
gaagcagtcg atccgtgaga tcagccgacg caccgggcag gcgcgcaaca cgatcgcaaa    4980
gtatttgaac gcaggtacaa tcgagccgac gttcacggta ccggaacgac caagcaagct    5040
agcttagtaa agccctcgct agattttaat gcggatgttg cgattacttc gccaactatt    5100
gcgataacaa gaaaaagcca gcctttcatg atatatctcc caatttgtgt agggcttatt    5160
atgcacgctt aaaaataata aaagcagact tgacctgata gtttggctgt gagcaattat    5220
gtgcttagtg catctaacgc ttgagttaag ccgcgccgcg aagcggcgtc ggcttgaacg    5280
aattgttaga cattatttgc cgactacctt ggtgatctcg cctttcacgt agtggacaaa    5340
ttcttccaac tgatctgcgc gcgaggccaa gcgatcttct tcttgtccaa gataagcctg    5400
tctagcttca agtatgacgg gctgatactg ggccggcagg cgctccattg cccagtcggc    5460
agcgacatcc ttcggcgcga ttttgccggt tactgcgctg taccaaatgc gggacaacgt    5520
aagcactaca tttcgctcat cgccagccca gtcgggcggc gagttccata gcgttaaggt    5580
```

```
ttcatttagc gcctcaaata gatcctgttc aggaaccgga tcaaagagtt cctccgccgc    5640
tggacctacc aaggcaacgc tatgttctct tgcttttgtc agcaagatag ccagatcaat    5700
gtcgatcgtg gctggctcga agatacctgc aagaatgtca ttgcgctgcc attctccaaa    5760
ttgcagttcg cgcttagctg gataacgcca cggaatgatg tcgtcgtgca caacaatggt    5820
gacttctaca gcgcggagaa tctcgctctc tccaggggaa gccgaagttt ccaaaaggtc    5880
gttgatcaaa gctcgccgcg ttgtttcatc aagccttacg gtcaccgtaa ccagcaaatc    5940
aatatcactg tgtggcttca ggccgccatc cactgcggag ccgtacaaat gtacggccag    6000
caacgtcggt tcgagatggc gctcgatgac gccaactacc tctgatagtt gagtcgatac    6060
ttcggcgatc accgcttccc tcatgatgtt aactttgtt ttagggcgac tgccctgctg    6120
cgtaacatcg ttgctgctcc ataacatcaa acatcgaccc acggcgtaac gcgcttgctg    6180
cttggatgcc cgaggcatag actgtacccc aaaaaaacag tcataacaag ccatgaaaac    6240
cgccactgcg ccgttaccac cgctgcgttc ggtcaaggtt ctggaccagt tgcgtgagcg    6300
catacgctac ttgcattaca gcttacgaac cgaacaggct tatgtccact gggttcgtgc    6360
cttcatccgt ttccacggtg tgcgtcaccc ggcaaccttg gcagcagcg aagtcgaggc    6420 atttctgtcc tggctggcga acgagcgcaa ggtttcggtc tccacgcatc gtcaggcatt    6480
ggcggccttg ctgttcttct acggcaagtg ctgtgcacgg atctgccctg gcttcaggag    6540
atcggaagac ctcggccgtc cgggcgcttg ccggtggtgc tgaccccgga tgaagtctct    6600
agagctctag agggttcgca tcctcggttt tctggaaggc gagcatcgtt tgttcgccca    6660
gcttctgtat ggaacgggca tgcggatcag tgagggtttg caactgcggg tcaaggatct    6720
ggatttcgat cacggcacga tcatcgtgcg ggagggcaag ggctccaagg atcgggcctt    6780
gatgttaccc gagagcttgg cacccagcct gcgcgagcag ggatcgatac cgtgcggctg    6840
catgaaatcc tggccggttt gtctgatgcc aagctggcgg cctggccggc cagcttggcc    6900
gctgaagaaa ccgagcgccg ccgtctaaaa aggtgatgtg tatttgagta aaacagcttg    6960
cgtcatgcgg tcgctgcgta tatgatgcga tgagtaaata aacaaatacg caaggggaac    7020
gcatgaaggt tatcgctgta cttaaccaga aaggcgggtc aggcaagacg accatcgcaa    7080
cccatctagc ccgcgccctg caactcgccg gggccgatgt tctgttagtc gattccgatc    7140
cccagggcag tgcccgcgat tgggcggccg tgcgggaaga tcaaccgcta accgttgtcg    7200
gcatcgaccg cccgacgatt gaccgcgacg tgaaggccat cggccggcgc gacttcgtag    7260
tgatcgacgg agcgccccag gcggcggact tggctgtgtc cgcgatcaag gcagccgact    7320
tcgtgctgat tccggtgcag ccaagcccct acgacatatg gccaccgcc gacctggtgg    7380 agctggttaa gcagcgcatt gaggtcacgg atggaaggct acaagcggcc tttgtcgtgt    7440
cgcgggcgat caaaggcacg cgcatcggcg gtgaggttgc cgaggcgctg gccgggtacg    7500
agctgcccat tcttgagtcc cgtatcacgc agcgcgtgag ctacccaggc actgccgccg    7560
ccggcacaac cgttcttgaa tcagaacccg agggcgacgc tgcccgcgag gtccaggcgc    7620
tggccgctga aattaaatca aaactcattt gagttaatga ggtaaagaga aaatgagcaa    7680
aagcacaaac acgctaagtg ccggccgtcc gagcgcacg agcagcaagg ctgcaacgtt    7740
ggccagcctg gcagacacgc cagccatgaa gcgggtcaac tttcagttgc cggcggagga    7800
tcacaccaag ctgaagatgt acgcggtacg ccaaggcaag accattaccg agctgctatc    7860
tgaatacatc gcgcagctac cagagtaaat gagcaaatga ataaatgagt agatgaattt    7920
```

```
tagcggctaa aggaggcggc atggaaaatc aagaacaacc aggcaccgac gccgtggaat   7980
gccccatgtg tggaggaacg ggcggttggc caggcgtaag cggctgggtt gtctgccggc   8040
cctgcaatgg cactggaacc cccaagcccg aggaatcggc gtgacggtcg caaaccatcc   8100
ggcccggtac aaatcggcgc ggcgctgggt gatgacctgg tggagaagtt gaaggccgcg   8160
caggccgccc agcggcaacg catcgaggca gaagcacgcc ccggtgaatc gtggcaagcg   8220
gccgctgatc gaatccgcaa agaatcccgg caaccgccgg cagccggtgc gccgtcgatt   8280
aggaagccgc ccaagggcga cgagcaacca gattttttcg ttccgatgct ctatgacgtg   8340
ggcacccgcg atagtcgcag catcatggac gtggccgttt ccgtctgtc gaagcgtgac    8400 cgacgagctg gcgaggtgat ccgctacgag cttccagacg ggcacgtaga ggtttccgca   8460
gggccggccg gcatggccag tgtgtgggat tacgacctgg tactgatggc ggtttcccat   8520
ctaaccgaat ccatgaaccg ataccgggaa gggaagggag acaagcccgg ccgcgtgttc   8580
cgtccacacg ttgcggacgt actcaagttc tgccggcgag ccgatggcgg aaagcagaaa   8640
gacgacctgg tagaaacctg cattcggtta aacaccacgc acgttgccat gcagcgtacg   8700
aagaaggcca gaacggccg cctggtgacg gtatccgagg gtgaagcctt gattagccgc    8760
tacaagatcg taaagagcga aaccgggcgg ccggagtaca tcgagatcga gctagctgat   8820
tggatgtacc gcgagatcac agaaggcaag aacccggacg tgctgacggt tcaccccgat   8880 tacttttga tcgatcccgg catcggccgt tttctctacc gcctggcacg ccgcgccgca    8940
ggcaaggcag aagccagatg gttgttcaag acgatctacg aacgcagtgg cagcgccgga   9000
gagttcaaga agttctgttt caccgtgcgc aagctgatcg ggtcaaatga cctgccggag   9060
tacgatttga aggaggaggc ggggcaggct ggcccgatcc tagtcatgcg ctaccgcaac   9120
ctgatcgagg gcgaagcatc cgccggttcc taatgtacgg agcagatgct agggcaaatt   9180
gccctagcag gggaaaaagg tcgaaaaggt ctctttcctg tggatagcac gtacattggg   9240
aacccaaagc cgtacattgg gaaccggaac ccgtacattg gaacccaaa gccgtacatt    9300 gggaaccggt cacacatgta agtgactgat ataaagaga aaaaggcga ttttccgcc     9360 taaaactctt taaaacttat taaaactctt aaaacccgcc tggcctgtgc ataactgtct   9420
ggccagcgca cagccgaaga gctgcaaaaa gcgcctaccc ttcggtcgct cgctcccta    9480 cgccccgccg cttcgcgtcg gcctatcgcg gccgctggcc gctcaaaaat ggctggccta   9540
cggccaggca atctaccagg gcgcggacaa gccgcgccgt cgccactcga ccgccggcgc   9600
ccacatcaag gcaccctgcc tcgcgcgttt cggtgatgac ggtgaaaacc tctgacacat   9660
gcagctcccg gagacggtca cagcttgtct gtaagcggat gccgggagca gacaagcccg   9720
tcagggcgcg tcagcgggtg ttggcggtg tcgggcgca gccatgaccc agtcacgtag     9780
cgatagcgga gtgtatactg gcttaactat gcggcatcag agcagattgt actgagagtg   9840
caccatatgc ggtgtgaaat accgcacaga tgcgtaagga aaaataccg catcaggcgc    9900 tcttccgctt cctcgctcac tgactcgctg cgctcggtcg ttcggctgcg gcgagcggta   9960
tcagctcact caaaggcggt aatacggtta tccacagaat cagggataa cgcaggaaag   10020 aacatgtgag caaaaggcca gcaaaaggcc aggaaccgta aaaaggccgc gttgctggcg   10080 ttttccata ggctccgccc ccctgacgag catcacaaaa atcgacgctc aagtcagagg    10140
tggcgaaacc cgacaggact ataaagatac caggcgtttc ccctggaag ctccctcgtg    10200 cgctctcctg ttccgaccct gccgcttacc ggatacctgt ccgcctttct cccttcggga   10260
agcgtggcgc tttctcatag ctcacgctgt aggtatctca gttcggtgta ggtcgttcgc   10320
```

```
tccaagctgg gctgtgtgca cgaacccccc gttcagcccg accgctgcgc cttatccggt    10380
aactatcgtc ttgagtccaa cccggtaaga cacgacttat cgccactggc agcagccact    10440
ggtaacagga ttagcagagc gaggtatgta ggcggtgcta cagagttctt gaagtggtgg    10500
cctaactacg gctacactag aaggacagta tttggtatct gcgctctgct gaagccagtt    10560
accttcggaa aaagagttgg tagctcttga tccggcaaac aaaccaccgc tggtagcggt    10620
ggtttttttg tttgcaagca gcagattacg cgcagaaaaa aaggatctca agaagatccg    10680
gaaaacgcaa gcgcaaagag aaagcaggta gcttgcagtg gcttacatg gcgatagcta     10740
gactgggcgt tttatggac agcaagcgaa ccggaattgc cagattcgaa gctcggtccc     10800
gtgggtgttc tgtcgtctcg ttgtacaacg aaatccattc ccattccgcg ctcaagatgg    10860
cttcccctcg gcagttcatc agggctaaat caatctagcc gacttgtccg gtgaaatggg    10920
ctgcactcca acagaaacaa tcaaacaaac atacacagcg acttattcac acgcgacaaa    10980
ttacaacggt atatatcctg ccagtactgg gcccccctcga gggcgatcgc tacgtacctg   11040
caggcccggg ttaattaagc ggccgcttca cggaaagttg ttatatataa gttcagtaaa    11100
taataatgaa atataaattt taattatatc tagtactcaa taagaagatg gagaaagtta    11160
tgttaattat agttataaat tatttataaa tttaatatat atatataaag aaaatagttg    11220
tataactaat aattattttt acaatacttt atatagttat atttaaaaaa attttaaaat    11280
taaaatacta ttattttgtt caatatatta atatttatat tatttaatt attattgaat     11340
atgaataaat ttttttttgaa aattatattt ttaattttta gaaatttat ataactttcc    11400
atatatatat ttctgatttg tcaatttctt ttgagattta tctaaattga tttgaatttt    11460
ttttattttt aaaaaataaa ataattttaa aatttcttgg aatttatat aaattttgg      11520
atttttcaaa aaaaattgag atttttttct tttttttcga tttttttaaat ttatttcagg   11580
aaaatataaa ctaacttttc tttgctttgg gtataattaa tattagataa cccacaaatt    11640
agatcaatag gagcttcatg tcctaatccc atttaattac ttttgttgta tcattaattt    11700
agtcgacctt acatagtagc tctatggggc aaatagttat aaatgttaaa ttagtatttta   11760
aatcttgaag tttttaattt aaagttcaga ctattagtat tatatcaaat atttaagggt    11820
aaatatatat tctaatatct aagcttgggt caaggtttaa attaagtact taaacttggt    11880
tttatagttc aaattgattt aaataactaa gtattaattt gaattaagaa gcaaagttca    11940
agtacctaat tagactataa aaaaaacttt tgctagtaaa ttgaaccta aagtcgagtt     12000
tagttatcta attggacaaa aaaatcttaa ataccaattt aaaccctaaa gtcaagttta    12060
ggtaccaaag tgtatattta tctaatattt aaatttgatc cacctaattt aaatttttt    12120
ggtccaatgc aataagagaa ttaattaata cttacacaca tgatagagat atacccacaa    12180
cagatacaca ctacaaaaaa cattaaaaaa tagaaagata tatttcctac aaaatttaaa    12240
agcatttaat tttttaacta acattagaca aatggaaatg gaaagactta ttttttaagtt  12300
tatggatgaa tctaatttat ctaaacattg gttttttttt ttttgtgacg aaatatgggt    12360
gagagaaggt agtaagctaa gtaggggagt aatatctcaa acaaataatt aaaaaactcc    12420
tttaaatgtg gctataaata cctgaaacca atccttcttt cctcaactca atcttcaat     12480
ctttagatca tctctccaaa aaaataccat gtgcggaatt gttggtgcta tcgcccaaag    12540
agacgttgct gagattttgt tagagggtct gcgaaggcta gagtatagag gatatgactc    12600
cgctggtctg gctgtcgttg atgctgaggg tcatatgaca aggctaagaa ggttaggaaa    12660
```

```
ggttcagatg cttgctcagg cagctgagga acatccattg catggaggta ctggtattgc    12720
acataccagg tgggctactc atggggagcc atcagaagtt aatgctcatc acatgtgag     12780 tgagcatatc gttgtagttc acaatgggat aattgaaaac cacgaaccat tgagggaaga    12840
gttaaaggca agaggatata cttttgtgag tgagactgac actgaggtta ttgcacattt    12900
agtgaactgg gaactcaaac aggggggcac attgcgtgag gctgtgttaa gagctattcc    12960
tcaacttaga ggtgcatacg gtactgttat tatggattca agacacccag atactctcct    13020
tgcagctaga tcaggtagtc ccttggtcat aggacttgga atgggtgaaa attttatcgc    13080
tagcgaccaa ttggccttat tgccagttac aagacgattt attttccttg aagagggcga    13140
tattgctgag attactagaa ggtctgtgaa catctttgat aagactggcg ctgaggttaa    13200
acgtcaggat atcgagtcta accttcaata cgatgctggt gataaaggaa tttacaggca    13260
ttatatgcaa aaggaaattt atgaacaacc aaatgctatc aaaaacacac ttactggccg    13320
tatttctcat ggacaggtcg atttaagcga gcttggtcct aatgcagacg aactgctatc    13380
aaaagttgag cacatacaga tactggcatg cggaactagt tataattcag gatggtgtc    13440 tagatactgg ttcgaaagct tggcaggtat accttgtgat gtagagatcg cttctgagtt    13500
taggtataga aagtctgctg tgcgtagaaa ttcattaatg attacattat ctcaatccgg    13560
agaaacagca gatacactgg ctggattgag gctttctaag gaactcggat atctgggttc    13620
acttgctatt tgtaatgtac caggttcctc attggttcgt gaatcagatc tagcacttat    13680
gacaaatgca ggaactgaaa taggtgtggc aagtaccaag gctttcacaa cccaactgac    13740 cgtacttta atgttggtag caaaactcag tcgattaaag gggctagatg catctatcga    13800
acatgatatt gttcacgggc ttcaagctct cccttcaaga attgaacaaa tgctttcaca    13860
agataagaga atagaggcat tggctgaaga tttttccgac aaacatcacg cattgtttct    13920
tggacgtggc gatcaatatc caattgcatt ggaaggagct ttgaagttga agaaataag    13980 ttacattcac gcagaagcat atgcagctgg agaactcaag catggtccctt tggcactcat    14040 cgacgctgac atgcccgtga tcgtagtggc tcctaataac gaactgctcg aaaagcttaa    14100
atcaaatatc gaagaggttc gagctagagg aggtcagctt tacgttttcg ctgaacaaga    14160
tgctggattc gtgtcaagcg ataatatgca tataattgaa atgcctcacg ttgaagaagt    14220
gattgcacct atattttata cagtcccatt gcaacttcta gcttaccatg ttgcacttat    14280
taaaggaact gatgttgatc agcctagaaa cctagcaaaa tctgtaacag tcgaataaa    14339
```

<210> SEQ ID NO 15
<211> LENGTH: 7389
<212> TYPE: DNA
<213> ORGANISM: Artificial Sequence
<220> FEATURE:
<223> OTHER INFORMATION: nucleotide sequence of pEA2

<400> SEQUENCE: 15

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcgggctgg cttaactatg cggcatcaga gcagattgta ctgagagtgc       180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt     360
tttcccagtc acgacgttgt aaaacgacgg ccagtgaatt gggcccggcc ggccgcgatc      420
```

```
gcgcggccgc ttcacggaaa gttgttatat ataagttcag taaataataa tgaaatataa      480
attttaatta tatctagtac tcaataagaa gatggagaaa gttatgttaa ttatagttat      540
aaattattta taaatttaat atatatatat aaagaaaata gttgtataac taataattat      600
ttttacaata ctttatatag ttatatttaa aaaaatttta aaattaaaat actattattt      660
tgttcaatat attaatattt atattattta atttattatt gaatatgaat aaatttttttt     720 tgaaaattat attttaatt tttagaaatt ttatataact ttccatatat atatttctga      780
tttgtcaatt tcttttgaga tttatctaaa ttgatttgaa ttttttttat ttttaaaaaa      840
taaaataatt ttaaaatttc ttggaatttt atataaattt ttggattttt caaaaaaaat      900
tgagattttt ttctttttttt tcgatttttt aaatttattt caggaaaata taaactaact      960
tttctttgct ttgggtataa ttaatattag ataacccaca aattagatca ataggagctt     1020
catgtcctaa tcccatttaa ttacttttgt tgtatcatta atttagtcga ccttacatag     1080
tagctctatg gggcaaatag ttataaatgt taaattagta tttaaatctt gaagtttta      1140 atttaaagtt cagactatta gtattatatc aaatatttaa gggtaaatat atattctaat     1200
atctaagctt gggtcaaggt ttaaattaag tacttaaact tggttttata gttcaaattg     1260
atttaaataa ctaagtatta atttgaatta agaagcaaag ttcaagtacc taattagact     1320
ataaaaaaaa cttttgctag taaattgaac cttaaagtcg agtttagtta tctaattgga     1380
caaaaaaatc ttaaatacca atttaaaccc taaagtcaag tttaggtacc aaagtgtata     1440
tttatctaat atttaaattt gatccaccta atttaaattt ttttggtcca atgcaataag     1500
agaattaatt aatacttaca cacatgatag agatataccc acaacagata cacactacaa     1560
aaaacattaa aaaatagaaa gatatatttc ctacaaaatt taaaagcatt taatttttta     1620
actaacatta gacaaatgga aatggaaaga cttattttta agtttatgga tgaatctaat     1680
ttatctaaac attgggtttt ttttttttgt gacgaaatat gggtgagaga aggtagtaag     1740
ctaagtaggg gagtaatatc tcaaacaaat aattaaaaaa ctcctttaaa tgtggctata     1800
aatacctgaa accaatcctt ctttcctcaa ctcaaatctt caatctttag atcatctctc     1860
caaaaaaata ccatgagtaa acggaatccg aagattctga agattttttct gtatatgtta     1920 cttctcaact ctctctttct catcatctac ttcgtttttc actcatcgtc gttttcagag     1980
tccagaatca gcaaccggtt atcgagttcc gccacaagga cggtacgagc cttcagaaat     2040
cgatgtcatg ccaggccagg gacaccggga tcgagttacg gaaatgcgag gcgaccgctt     2100
ccctcggcac cagcgccttt acactacaat agcccaagtc gcgcagcgag tcattatcca     2160
cggtaccatg gaggttatgc ggacgacgtg acagttagca tgggaccgga cgacgatcgt     2220
acagatatct ttggccccga aaccgatctc agcgaaacgc gccacctcaa cgacgcatac     2280
gggtttcggt catcccagat caccctcagc gaagatcccc acggcaccca cgcgcgttcc     2340
cggtacgacg acgaagacga tgtgagcacc acttattcct ccaacacggg caccagcgct     2400
tcaggtgtcg acaagttcga gcattacggt cccattccgg aggaaggcaa gcacgagcgg     2460
cgcggcgtgc gaccaccaca gatgtcgagg aaggaagtcc agctcatcaa cggcgaactc     2520
gttctcgagt gcaagattcc gactatattg tattcgtttt tgcccaggag agacgaagtg     2580
gagtttacgc acatgcggta cacagccgtc acttgtgacc ctgatgactt tgttgccagg     2640
ggttacaagt tgcgccagaa tatcggtcgt accgccaggg agacggagct gttcatctgc     2700
gtgaccatgt acaacgagga cgagttcgga ttcacacgga ctatgcacgc agtgatgaag     2760
```

```
aacatttcgc attttgttc ccgaaacaag agtaggacgt ggggagcgga tgggtggcag    2820
aagattgtgg tctgtgtggt ttcggatgga cgagagatca ttcaccccg gaccttggac    2880 gccctcgcag ccatgggcgt ttaccagcac ggtatcgcca agaactttgt caaccagaag    2940
gcggtgcagg cccacgttta cgagtacacg acacaagtgt ctctggacag cgacctcaag    3000
ttcaagggcg ccgagaaggg catcgtgccc tgccagatga ttttttgctt gaaggagaag    3060
aaccaaaaga aactcaactc gcatagatgg ttcttcaacg cctttggcaa agccttgaac    3120
ccgaatgtgt gtatcctcct agacgtcggc acccgccccg gcggcacaag tctctaccat    3180
ctctggaaag ccttcgacac ggattccaac gtggcggggg cctgcgggga aatcaaagcg    3240
atgaaggggc ggtttggcgg gaatttgctc aaccctctgg tggctagtca gaactttgag    3300
tacaagatga gcaatattct ggacaaaccg ttggagtcgg tgtttgggta catcacggtg    3360
ttgccgggcg ccttgtcggc gtatcggtac catgcgctgc agaacgatga gacgggccat    3420
gggccgttga gtcagtattt caagggcgag acgctccatg gcagcacgc ggatgtgttt    3480 acggcgaaca tgtacttggc cgaggaccga attctgtgtt gggagttggt ggccaagagg    3540
ggtgagaggt gggtgttgaa gtatgtgaag gggtgtacgg gtgagacgga tgtgcctgac    3600
accgtcccgg aattcgtctc gcaacgtcgt cgttggctca acggtgcctt cttcgccgcc    3660
gtctactccc tcgtccactt tcgacaaatc tggaaaaccg accacacctt tatgcgcaaa    3720
gcccttctcc acgtcgaatt cctctaccac ctcctgcaac tcctcttcac ctacttctcc    3780
ctggccaact tctacctcgc cttctacttt atcgccggcg gactcgccga tccccacgtc    3840 gacccttta actcggacgg ccacgtcgcg cgcatcatct tcaacatcct ccgctacgtc    3900
tgcgtcctgc tgatctgcac acaattcatc ttgtccctcg gcaaccgtcc gcagggtgcc    3960
aaaagaatgt atctcgcatc catgatcatc tacgccgtca tcatggtgta caccaccttc    4020
gccaccatct tcatcgtcgt gcgacaaatc caaccctctc aaaaatccga cgacaagccc    4080
gacctcgaac tcgcaacaa cgtcttcacc aacctgatcg tctccgtggc tagtaccctc    4140
gggctctact tcgtcatgtc cttttctctat ctcgacccct ggcacatgtt cacctcggcc    4200
atccagtact ttgtcctgct gccttcctac atctgcacgc tccagatcta cgccttttgc    4260
aacacccacg acgtcacatg gggcaccaaa ggcgacaacg tgatgcgcac cgatctcgga    4320
ggcgccattg gcaagggaag caccgtcgaa ctggaaatgc cttcggacca actcgacatc    4380
gactcgggat acgacgaatg tctacgaaat ctccgggatc gcgtcatggt ccctgccgtt    4440
cccgtgtccg aggaccagct gcagcaggat tactacaagt cggtgcgcac gtacatggtg    4500
gtgtcgtgga tggtggccaa cgcgacgctg gccatggcgg tgtcggaagc gtatggcgat    4560
tcggaaattg gggataattt ttacttgcgg tttatcctgt gggcggtggc ggccctggcg    4620
ctgtttagag cgttggggtc gacgacgttt gcggcgatta atctggtgag tgctctcgtg    4680
gagggcaggg tcaggctgag gttgaatatg aaagggttta ggtggattaa ggagaagtgg    4740
ggggatgcgg atgtgaaggg caagtttgag ggggttgggg atcgggcgag ggggttggcg    4800
aggcggtgag agctccctag ggacgccggt gaagaggcag tgcaagacgt ttaaacgcta    4860
gcaagcttgg acacgctgaa atcaccagtc tctctctaca aatctatctc tctctatttt    4920
ctccataata atgtgtgagt agttcccaga taagggaatt agggttccta tagggtttcg    4980
ctcatgtgtt gagcatataa gaaacccttg tatgtatttt gtatttgtaa aatacttcta    5040
tcaataaaat ttctaattcc taaaaccaaa atccagtact aaaatccaga tcatgcatgg    5100
tacagcacgc gtcctgcagg cccgggttaa ttaaatttaa atggcgcgcc agcttggcgt    5160
```

```
aatcatggtc atagctgttt cctgtgtgaa attgttatcc gctcacaatt ccacacaaca    5220
tacgagccgg aagcataaag tgtaaagcct ggggtgccta atgagtgagc taactcacat    5280
taattgcgtt gcgctcactg cccgctttcc agtcgggaaa cctgtcgtgc cagctgcatt    5340
aatgaatcgg ccaacgcgcg gggagaggcg gtttgcgtat tgggcgctct tccgcttcct    5400
cgctcactga ctcgctgcgc tcggtcgttc ggctgcggcg agcggtatca gctcactcaa    5460
aggcggtaat acggttatcc acagaatcag gggataacgc aggaaagaac atgtgagcaa    5520
aaggccagca aaaggccagg aaccgtaaaa aggccgcgtt gctggcgttt ttccataggc    5580
tccgcccccc tgacgagcat cacaaaaatc gacgctcaag tcagaggtgg cgaaacccga    5640
caggactata aagataccag gcgtttcccc ctggaagctc cctcgtgcgc tctcctgttc    5700
cgaccctgcc gcttaccgga tacctgtccg cctttctccc ttcgggaagc gtggcgcttt    5760
ctcatagctc acgctgtagg tatctcagtt cggtgtaggt cgttcgctcc aagctgggct    5820
gtgtgcacga accccccgtt cagcccgacc gctgcgcctt atccggtaac tatcgtcttg    5880
agtccaaccc ggtaagacac gacttatcgc cactggcagc agccactggt aacaggatta    5940
gcagagcgag gtatgtaggc ggtgctacag agttcttgaa gtggtggcct aactacggct    6000
acactagaag gacagtattt ggtatctgcg ctctgctgaa gccagttacc ttcggaaaaa    6060
gagttggtag ctcttgatcc ggcaaacaaa ccaccgctgg tagcggtggt ttttttgttt    6120
gcaagcagca gattacgcgc agaaaaaaag gatctcaaga agatcctttg atcttttcta    6180
cggggtctga cgctcagtgg aacgaaaact cacgttaagg gattttggtc atgagattat    6240 caaaaggat cttcacctag atccttttaa attaaaaatg aagttttaaa tcaatctaaa    6300
gtatatatga gtaaacttgg tctgacagtt accaatgctt aatcagtgag gcacctatct    6360
cagcgatctg tctatttcgt tcatccatag ttgcctgact ccccgtcgtg tagataacta    6420
cgatacggga gggcttacca tctggcccca gtgctgcaat gataccgcga gacccacgct    6480
caccggctcc agatttatca gcaataaacc agccagccgg aagggccgag cgcagaagtg    6540
gtcctgcaac tttatccgcc tccatccagt ctattaattg ttgccgggaa gctagagtaa    6600
gtagttcgcc agttaatagt ttgcgcaacg ttgttgccat tgctacaggc atcgtggtgt    6660
cacgctcgtc gtttggtatg gcttcattca gctccggttc ccaacgatca aggcgagtta    6720
catgatcccc catgttgtgc aaaaaagcgg ttagctcctt cggtcctccg atcgttgtca    6780
gaagtaagtt ggccgcagtg ttatcactca tggttatggc agcactgcat aattctctta    6840
ctgtcatgcc atccgtaaga tgcttttctg tgactggtga gtactcaacc aagtcattct    6900
gagaatagtg tatgcggcga ccgagttgct cttgcccggc gtcaatacgg ataataccg    6960 cgccacatag cagaacttta aaagtgctca tcattggaaa acgttcttcg ggcgaaaac    7020 tctcaaggat cttaccgctg ttgagatcca gttcgatgta acccactcgt gcacccaact    7080
gatcttcagc atcttttact ttcaccagcg tttctgggtg agcaaaaaca ggaaggcaaa    7140
atgccgcaaa aaagggaata agggcgacac ggaaatgttg aatactcata ctcttccttt    7200
ttcaatatta ttgaagcatt tatcagggtt attgtctcat gagcggatac atatttgaat    7260
gtatttagaa aaataaacaa ataggggttc cgcgcacatt tccccgaaaa gtgccacctg    7320
acgtctaaga aaccattatt atcatgacat taacctataa aaataggcgt atcacgaggc    7380
cctttcgtc                                                           7389
```

<210> SEQ ID NO 16

<211> LENGTH: 19023
<212> TYPE: DNA
<213> ORGANISM: Artificial Sequence
<220> FEATURE:
<223> OTHER INFORMATION: nucleotide sequence of pTEA3

<400> SEQUENCE: 16

| | | | | | |
|---|---|---|---|---|---|
| aattcaacg | gtatatatcc | tgccagtact | gggcccctc | gagggcgatc | gcgcggccgc | 60 |
| ttcacggaaa | gttgttatat | ataagttcag | taaataataa | tgaaatataa | attttaatta | 120 |
| tatctagtac | tcaataagaa | gatggagaaa | gttatgttaa | ttatagttat | aaattattta | 180 |
| taaatttaat | atatatatat | aaagaaaata | gttgtataac | taataattat | ttttacaata | 240 |
| ctttatatag | ttatatttaa | aaaaatttta | aaattaaaat | actattattt | tgttcaatat | 300 |
| attaatattt | atattattta | atttattatt | gaatatgaat | aaattttttt | tgaaaattat | 360 |
| attttaatt | tttagaaatt | ttatataact | ttccatatat | atatttctga | tttgtcaatt | 420 |
| tcttttgaga | tttatctaaa | ttgatttgaa | tttttttat | ttttaaaaaa | taaataatt | 480 |
| ttaaaatttc | ttggaatttt | ataaaattt | ttggatttt | caaaaaaat | tgagattttt | 540 |
| ttcttttttt | tcgattttt | aaatttattt | caggaaaata | taaactaact | tttctttgct | 600 |
| ttgggtataa | ttaatattag | ataacccaca | aattagatca | ataggagctt | catgtcctaa | 660 |
| tcccatttaa | ttacttttgt | tgtatcatta | atttagtcga | ccttacatag | tagctctatg | 720 |
| gggcaaatag | ttataaatgt | taaattagta | tttaaatctt | gaagttttta | atttaaagtt | 780 |
| cagactatta | gtattatatc | aaatatttaa | gggtaaatat | atattctaat | atctaagctt | 840 |
| gggtcaaggt | ttaattaag | tacttaaact | tggttttata | gttcaaattg | atttaaataa | 900 |
| ctaagtatta | atttgaatta | agaagcaaag | ttcaagtacc | taattagact | ataaaaaaaa | 960 |
| cttttgctag | taaattgaac | cttaaagtcg | agtttagtta | tctaattgga | caaaaaaatc | 1020 |
| ttaaatacca | atttaaaccc | taaagtcaag | tttaggtacc | aaagtgtata | tttatctaat | 1080 |
| atttaaattt | gatccaccta | atttaaattt | ttttggtcca | atgcaataag | agaattaatt | 1140 |
| aatacttaca | cacatgatag | agatataccc | acaacagata | cacactacaa | aaaacattaa | 1200 |
| aaaatagaaa | gatatatttc | ctacaaaatt | taaaagcatt | taattttta | actaacatta | 1260 |
| gacaaatgga | aatggaaaga | cttattttta | agtttatgga | tgaatctaat | ttatctaaac | 1320 |
| attgggtttt | tttttttgt | gacgaaatat | gggtgagaga | aggtagtaag | ctaagtaggg | 1380 |
| gagtaatatc | tcaaacaaat | aattaaaaaa | ctcctttaaa | tgtggctata | aatacctgaa | 1440 |
| accaatcctt | ctttcctcaa | ctcaaatctt | caatctttag | atcatctctc | caaaaaata | 1500 |
| ccatgagtaa | acggaatccg | aagattctga | agattttct | gtatatgtta | cttctcaact | 1560 |
| ctctctttct | catcatctac | ttcgtttttc | actcatcgtc | gttttcagag | tccagaatca | 1620 |
| gcaaccggtt | atcgagttcc | gccacaagga | cggtacgagc | cttcagaaat | cgatgtcatg | 1680 |
| ccaggccagg | gacaccggga | tcgagttacg | gaaatgcgag | gcgaccgctt | ccctcggcac | 1740 |
| cagcgccttt | acactacaat | agcccaagtc | gcgcagcgag | tcattatcca | cggtaccatg | 1800 |
| gaggttatgc | ggacgacgtg | acagttagca | tgggaccgga | cgacgatcgt | acagatatct | 1860 |
| ttggccccga | aaccgatctc | agcgaaacgc | gccacctcaa | cgacgcatac | gggtttcggt | 1920 |
| catcccagat | caccctcagc | gaagatcccc | acggcaccca | cgcgcgttcc | cggtacgacg | 1980 |
| acgaagacga | tgtgagcacc | acttattcct | ccaacacggg | caccagcgct | tcaggtgtcg | 2040 |
| acaagttcga | gcattacggt | cccattccgg | aggaaggcaa | gcacgagcgg | cgcggcgtgc | 2100 |
| gaccaccaca | gatgtcgagg | aaggaagtcc | agctcatcaa | cggcgaactc | gttctcgagt | 2160 |

```
gcaagattcc gactatattg tattcgtttt tgcccaggag agacgaagtg gagtttacgc    2220
acatgcggta cacagccgtc acttgtgacc ctgatgactt tgttgccagg ggttacaagt    2280
tgcgccagaa tatcggtcgt accgccaggg agacggagct gttcatctgc gtgaccatgt    2340
acaacgagga cgagttcgga ttcacacgga ctatgcacgc agtgatgaag aacatttcgc    2400 attttgttc ccgaaacaag agtaggacgt ggggagcgga tgggtggcag aagattgtgg     2460
tctgtgtggt ttcggatgga cgagagatca ttcaccccg gaccttggac gccctcgcag     2520
ccatgggcgt ttaccagcac ggtatcgcca agaactttgt caaccagaag gcggtgcagg    2580
cccacgttta cgagtacacg acacaagtgt ctctggacag cgacctcaag ttcaagggcg    2640
ccgagaaggg catcgtgccc tgccagatga ttttttgctt gaaggagaag aaccaaaaga    2700
aactcaactc gcatagatgg ttcttcaacg cctttggcaa agccttgaac ccgaatgtgt    2760
gtatcctcct agacgtcggc acccgccccg gcggcacaag tctctaccat ctctggaaag    2820
ccttcgacac ggattccaac gtggcggggg cctgcgggga aatcaaagcg atgaaggggc    2880
ggtttggcgg gaatttgctc aaccctctgg tggctagtca gaactttgag tacaagatga    2940
gcaatattct ggacaaaccg ttggagtcgg tgtttgggta catcacggtg ttgccgggcg    3000
ccttgtcggc gtatcggtac catgcgctgc agaacgatga gacgggccat gggccgttga    3060
gtcagtattt caagggcgag acgctccatg gcagcacgc ggatgtgttt acggcgaaca     3120
tgtacttggc cgaggaccga attctgtgtt gggagttggt ggccaagagg ggtgagaggt    3180
gggtgttgaa gtatgtgaag gggtgtacgg gtgagacgga tgtgcctgac accgtcccgg    3240
aattcgtctc gcaacgtcgt cgttggctca acggtgcctt cttcgccgcc gtctactccc    3300
tcgtccactt tcgacaaatc tggaaaaccg accaccctt tatgcgcaaa gcccttctcc     3360
acgtcgaatt cctctaccac ctcctgcaac tcctcttcac ctacttctcc ctggccaact    3420
tctacctcgc cttctacttt atcgccggcg gactcgccga tccccacgtc gacccttta    3480 actcggacgg ccacgtcgcg cgcatcatct tcaacatcct ccgctacgtc tgcgtcctgc    3540
tgatctgcac acaattcatc ttgtccctcg gcaaccgtcc gcagggtgcc aaaagaatgt    3600
atctcgcatc catgatcatc tacgccgtca tcatggtgta caccaccttc gccaccatct    3660
tcatcgtcgt gcgacaaatc caaccctctc aaaaatccga cgacaagccc gacctcgaac    3720
tcggcaacaa cgtcttcacc aacctgatcg tctccgtggc tagtaccctc gggctctact    3780
tcgtcatgtc ctttctctat ctcgacccct ggcacatgtt cacctcggcc atccagtact    3840
ttgtcctgct gccttcctac atctgcacgc tccagatcta cgccttttgc aacacccacg    3900
acgtcacatg gggcaccaaa ggcgacaacg tgatgcgcac cgatctcgga ggcgccattg    3960
gcaagggaag caccgtcgaa ctggaaatgc cttcggacca actcgacatc gactcggat     4020 acgacgaatg tctacgaaat ctcccgggatc gcgtcatggt ccctgccgtt cccgtgtccg    4080
aggaccagct gcagcaggat tactacaagt cggtgcgcac gtacatggtg gtgtcgtgga    4140
tggtggccaa cgcgacgctg gccatggcgg tgtcggaagc gtatggcgat cggaaattg     4200 gggataattt ttacttgcgg tttatcctgt gggcggtggc ggccctggcg ctgtttagag    4260
cgttggggtc gacgacgttt gcggcgatta atctggtgag tgctctcgtg gagggcaggg    4320
tcaggctgag gttgaatatg aaagggttta ggtggattaa ggagaagtgg ggggatgcgg    4380
atgtgaaggg caagtttgag gggttggggg atcgggcgag ggggttggcg aggcggtgag    4440
agctccctag ggacgccggt gaagaggcag tgcaagacgt ttaaacgcta gcaagcttgg    4500
```

```
acacgctgaa atcaccagtc tctctctaca aatctatctc tctctatttt ctccataata    4560
atgtgtgagt agttcccaga taagggaatt agggttccta tagggtttcg ctcatgtgtt    4620
gagcatataa gaaacccta gtatgtattt gtatttgtaa aatacttcta tcaataaaat    4680
ttctaattcc taaaaccaaa atccagtact aaaatccaga tcatgcatgg tacagcacgc    4740
gtcctgcagg cccgggttaa ttaagcggcc gcttcacgga aagttgttat atataagttc    4800
agtaaataat aatgaaatat aaattttaat tatatctagt actcaataag aagatggaga    4860
aagttatgtt aattatagtt ataaattatt tataaattta atatatatat ataaagaaaa    4920
tagttgtata actaataatt attttacaa tactttatat agttatattt aaaaaaattt    4980
taaaattaaa atactattat tttgttcaat atattaatat ttatattatt taatttatta    5040
ttgaatatga ataaattttt tttgaaaatt atattttaa tttttagaaa ttttatataa    5100
ctttccatat atatattct gatttgtcaa tttcttttga gatttatcta aattgatttg    5160 aattttttt attttaaaa aataaaataa ttttaaaatt tcttggaatt ttatataaat    5220
ttttggattt tcaaaaaaa attgagattt ttttcttttt tttcgatttt ttaaatttat    5280
ttcaggaaaa tataaactaa cttttctttg ctttgggtat aattaatatt agataaccca    5340
caaattagat caataggagc ttcatgtcct aatcccattt aattacttt gttgtatcat    5400 taatttagtc gaccttacat agtagctcta tggggcaaat agttataaat gttaaattag    5460
tatttaaatc ttgaagtttt taatttaaag ttcagactat tagtattata tcaaatattt    5520
aagggtaaat atatattcta atatctaagc ttgggtcaag gtttaaatta agtacttaaa    5580
cttggtttta tagttcaaat tgatttaaat aactaagtat taatttgaat taagaagcaa    5640
agttcaagta cctaattaga ctataaaaaa aacttttgct agtaaattga accttaaagt    5700
cgagtttagt tatctaattg gacaaaaaaa tcttaaatac caatttaaac cctaaagtca    5760
agtttaggta ccaaagtgta tatttatcta atatttaaat ttgatccacc taatttaaat    5820
ttttttggtc caatgcaata agagaattaa ttaatactta cacacatgat agagatatac    5880
ccacaacaga tacacactac aaaaaacatt aaaaaataga aagatatatt tcctacaaaa    5940
tttaaaagca tttaattttt taactaacat tagacaaatg gaaatggaaa gacttatttt    6000
taagtttatg gatgaatcta atttatctaa acattgggtt ttttttttt gtgacgaaat    6060 atgggtgaga gaaggtagta agctaagtag gggagtaata tctcaaacaa ataattaaaa    6120 aactcccttta aatgtggcta taaatacctg aaaccaatcc ttctttcctc aactcaaatc    6180
ttcaatcttt agatcatctc tccaaaaaaa taccatgtgc ggaattgttg gtgctatcgc    6240
ccaaagagac gttgctgaga ttttgttaga gggtctgcga aggctagagt atagaggata    6300
tgactccgct ggtctggctg tcgttgatgc tgagggtcat atgacaaggc taagaaggtt    6360
aggaaaggtt cagatgcttg ctcaggcagc tgaggaacat ccattgcatg gaggtactgg    6420
tattgcacat accaggtggg ctactcatgg ggagccatca gaagttaatg ctcatccaca    6480
tgtgagtgag catatcgttg tagttcacaa tgggataatt gaaaaccacg aaccattgag    6540
ggaagagtta aaggcaagag gatatacttt tgtgagtgag actgacactg aggttattgc    6600
acatttagtg aactgggaac tcaaacaggg gggcacattg cgtgaggctg tgttaagagc    6660
tattcctcaa cttagaggtg catacggtac tgttattatg gattcaagac acccagatac    6720
tctccttgca gctagatcag gtagtcccett ggtcatagga cttggaatgg gtgaaaattt    6780
tatcgctagc gaccaattgg ccttattgcc agttacaaga cgatttatttt tccttgaaga    6840 gggcgatatt gctgagatta ctagaaggtc tgtgaacatc tttgataaga ctggcgctga    6900
```

```
ggttaaacgt caggatatcg agtctaacct tcaatacgat gctggtgata aaggaattta    6960
caggcattat atgcaaaagg aaatttatga acaaccaaat gctatcaaaa acacacttac    7020
tggccgtatt tctcatggac aggtcgattt aagcgagctt ggtcctaatg cagacgaact    7080
gctatcaaaa gttgagcaca tacagatact ggcatgcgga actagttata attcaggaat    7140
ggtgtctaga tactggttcg aaagcttggc aggtatacct tgtgatgtag agatcgcttc    7200
tgagtttagg tatagaaagt ctgctgtgcg tagaaattca ttaatgatta cattatctca    7260
atccggagaa acagcagata cactggctgg attgaggctt tctaaggaac tcggatatct    7320
gggttcactt gctatttgta atgtaccagg ttcctcattg gttcgtgaat cagatctagc    7380
acttatgaca aatgcaggaa ctgaaatagg tgtggcaagt accaaggctt tcacaaccca    7440
actgaccgta cttttaatgt tggtagcaaa actcagtcga ttaaaggggc tagatgcatc    7500
tatcgaacat gatattgttc acgggcttca agctctccct tcaagaattg aacaaatgct    7560
ttcacaagat aagagaatag aggcattggc tgaagatttt tccgacaaac atcacgcatt    7620
gtttcttgga cgtggcgatc aatatccaat tgcattggaa ggagctttga agttgaaaga    7680
aataagttac attcacgcag aagcatatgc agctggagaa ctcaagcatg gtcctttggc    7740
actcatcgac gctgacatgc ccgtgatcgt agtggctcct aataacgaac tgctcgaaaa    7800
gcttaaatca aatatcgaag aggttcgagc tagaggaggt cagctttacg ttttcgctga    7860
acaagatgct ggattcgtgt caagcgataa tatgcatata attgaaatgc tcacgttga    7920
agaagtgatt gcacctatat tttatacagt cccattgcaa cttctagctt accatgttgc    7980
acttattaaa ggaactgatg ttgatcagcc tagaaaccta gcaaaatctg taacagtcga    8040
ataaacgcgt aggcctgacg ccggtgaaga ggcagtgcaa gaccacgtga acggcgcgc    8100
ccccgatccg cgtttgtgtt ttctgggttt ctcacttaag cgtctgcgtt ttacttttgt    8160
attgggtttg gcgtttagta gtttgcggta gcgttcttgt tatgtgtaat tacgcttttt    8220
cttcttgctt cagcagtttc ggttgaaata taaatcgaat caagtttcac tttatcagcg    8280
ttgttttaaa ttttggcatt aaattggtga aaattgcttc aattttgtat ctaaatagaa    8340
gagacaacat gaaattcgac ttttgacctc aaatcttcga acatttattt cctgatttca    8400
cgatggatga ggataacgaa agggcggttc ctatgtccgg gaaagttccc gtagaagaca    8460
atgagcaaag ctactgaaac gcggacacga cgtcgcattg gtacggatat gagttaaacc    8520
gactcaattc ctttattaag acataaaccg attttggtta agtgtaaca gtgagctgat    8580
ataaaaccga aacaaaccgg tacaagtttg attgagcaac ttgatgacaa acttcagaat    8640
tttggttatt gaatgaaaat catagtctaa tcgtaaaaaa tgtacagaag aaaagctaga    8700
gcagaacaaa gattctatat tctggttcca atttatcatc gctttaacgt ccctcagatt    8760
tgatcgggga attcgatatc attaccctgt tatccctaaa gcttattaat gtttgtcgag    8820
gagaaatatg agtcgaggca tggatacact aagttcccct gaagtgagca tgatctttga    8880
tgctgagatg attcccagag caagatagtt tgtgctgcaa gtgacacaat tgtaatgaaa    8940
ccaccactca acgaatttac ttgtggcttt gacatgtcgt gtgctctgtt tgtatttgtg    9000
agtgccggtt ggtaattatt tttgttaatg tgattttaaa acctcttatg taaatagtta    9060
ctttatctat tgaagtgtgt tcttgtggtc tatagtttct caaagggaaa ttaaaatgtt    9120
gacatcccat ttcaattga taacttggta tacacaaact ttgtaaattt ggtgatattt    9180
atggtcgaaa gaaggcaata cccattgtat gttccaatat caatatcaat acgataactt    9240
```

```
gataatacta acatatgatt gtcattgttt ttccagtatc aatatacatt aagctactac   9300
aaaattagta taaatcacta tattataaat cttttcggt tgtaacttgt aattcgtggg    9360
tttttaaaat aaaagcatgt gaaaattttc aaataatgtg atggcgcaat tttatttcc    9420
gagttccaaa atattgccgc ttcattaccc taatttgtgg cgccacatgt aaaacaaaag   9480
acgattctta gtggctatca ctgccatcac gcggatcact aatatgaacc gtcgattaaa   9540
acagatcgac ggtttataca tcattttatt gtacacacgg atcgatatct cagccgttag   9600
atttaatatg cgatctgatt gctcaaaaaa tagactctcc gtctttgcct ataaaaacaa   9660
tttcacatct ttctcaccca aatctactct taaccgttct tcttcttcta cagacatcaa   9720
tttctctcga ctctagagga tccaagctta tcgatttcga acccctcagg cgaagaacag   9780
gtatgatttg tttgtaatta gatcaggggt ttaggtcttt ccattactt ttaatgtttt    9840
ttctgttact gtctccgcga tctgatttta cgacaataga gtttcgggtt ttgtcccatt   9900
ccagtttgaa aataaaggtc cgtcttttaa gtttgctgga tcgataaacc tgtgaagatt   9960
gagtctagtc gatttattgg atgatccatt cttcatcgtt tttttcttgc ttcgaagttc  10020
tgtataacca gatttgtctg tgtgcgattg tcattaccta gccgtgtatc gagaactagg  10080
gttttcgagt caattttgcc ccttttggtt atatctggtt cgataacgat tcatctggat  10140
tagggtttta agtggtgacg tttagtattc caatttcttc aaaatttagt tatggataat  10200
gaaaatcccc aattgactgt tcaatttctt gttaaatgcg cagatcacaa tggcttcgat  10260
ctcctcctca gtcgcgaccg ttagccggac cgcccctgct caggccaaca tggtggctcc  10320
gttcaccggc cttaagtcca acgccgcctt ccccaccacc aagaaggcta acgacttctc  10380
cacccttccc agcaacggtg aagagttca atgtatgcag gtgtggccgg cctacggcaa   10440
caagaagttc gagacgctgt cgtacctgcc gccgctgtct atggcgccca ccgtgatgat  10500
ggcctcgtcg gccaccgccg tcgctccgtt ccaggggctc aagtccaccg ccagcctccc  10560
cgtcgcccgc cgctcctcca gaagcctcgg caacgtcagc aacggcggaa ggatccggtg  10620
catggccggc gccgaggaga tcgtgctgca gcccatcaag gagatctccg gcaccgtcaa  10680
gctgccgggg tccaagtcgc tttccaaccg gatcctccta ctcgccgccc tgtccgaggg  10740
gacaacagtg gttgataacc tgctgaacag tgaggatgtc cactacatgc tcgggccttt  10800
gaggactctt ggtctctctg tcgaagcgga caaagctgcc aaaagagctg tagttgttgg  10860
ctgtggtgga aagttcccag ttgaggatgc taaagaggaa gtgcagctct tcttggggaa  10920
tgctggaatc gcaatgcggt ccttgacagc agctgttact gctgctggtg aaatgcaac   10980
ttacgtgctt gatggagtac caagaatgag ggagagaccc attggcgact tggttgtcgg  11040
attgaagcag cttggtgcag atgttgattg tttccttggc actgactgcc cacctgttcg  11100
tgtcaatgga atcggagggc tacctggtgg caaggtcaag ctgtctggct ccatcagcag  11160
tcagtacttg agtgccttgc tgatggctgc tcctttggct cttggggatg tggagattga  11220
aatcattgat aaattaatct ccattccgta cgtcgaaatg acattgagat tgatggagcg  11280
ttttggtgtg aaagcagagc attctgatag ctgggacaga ttctacatta agggaggtca  11340
aaaatacaag tcccctaaaa atgcctatgt tgaaggtgat gcctcaagcg caagctattt  11400
cttggctggt gctgcaatta ctggagggac tgtgactgtg aaggttgtg gcaccaccag   11460
tttgcagggt gatgtgaagt tgctgaggt actggagatg atgggagcga aggttacatg   11520
gaccgagact agcgtaactg ttactggccc accgcgggag ccatttggga ggaaacacct  11580
caaggcgatt gatgtcaaca tgaacaagat gcctgatgtc gccatgactc ttgctgtggt  11640
```

```
tgccctcttt gccgatggcc cgacagccat cagagacgtg gcttcctgga gagtaaagga    11700
gaccgagagg atggttgcga tccggacgga gctaaccaag ctgggagcat ctgttgagga    11760
agggccggac tactgcatca tcacgccgcc ggagaagctg aacgtgacgg cgatcgacac    11820
gtacgacgac cacaggatgg cgatggcttt ctcccttgcc gcctgtgccg aggtccccgt    11880
caccatccgg gaccctgggt gcacccggaa gaccttcccc gactacttcg atgtgctgag    11940
cactttcgtc aagaattaag ctctagaact agtggatccc ccgatccgcg tttgtgtttt    12000 ctgggttct cacttaagcg tctgcgtttt acttttgtat tgggtttggc gtttagtagt      12060
ttgcggtagc gttcttgtta tgtgtaatta cgcttttct tcttgcttca gcagtttcgg      12120
ttgaaatata aatcgaatca agtttcactt tatcagcgtt gttttaaatt ttggcattaa    12180
attggtgaaa attgcttcaa ttttgtatct aaatagaaga acaacatga aattcgactt      12240 ttgacctcaa atcttcgaac atttatttcc tgatttcacg atggatgagg ataacgaaag    12300
ggcggttcct atgtccggga aagttcccgt agaagacaat gagcaaagct actgaaacgc    12360
ggacacgacg tcgcattggt acggatatga gttaaaccga ctcaattcct ttattaagac    12420
ataaaccgat tttggttaaa gtgtaacagt gagctgatat aaaaccgaaa caaaccggta    12480
caagtttgat tgagcaactt gatgacaaac ttcagaattt tggttattga atgaaaatca    12540
tagtctaatc gtaaaaaatg tacagaagaa aagctagagc agaacaaaga ttctatattc    12600
tggttccaat ttatcatcgc tttaacgtcc ctcagatttg atcgggaaac caaaacgtcg    12660
tgagacagtt tggttaacta taacggtcct aaggtagcga tcgaggcatt acggcattac    12720
ggcactcgcg agggtccgaa ttcgagcatg gagccattta caattgaata tatcctgccg    12780
ccgctgccgc tttgcacccg gtggagcttg catgttggtt tctacgcaga actgagccgg    12840
ttaggcagat aatttccatt gagaactgag ccatgtgcac cttcccccca acacggtgag    12900
cgacggggca acgagtgat ccacatggga ctttttaaaca tcatccgtcg gatggcgttg    12960
cgagagaagc agtcgatccg tgagatcagc cgacgcaccg ggcaggcgcg caacacgatc    13020
gcaaagtatt tgaacgcagg tacaatcgag ccgacgttca cggtaccgga acgaccaagc    13080
aagctagctt agtaaagccc tcgctagatt ttaatgcgga tgttgcgatt acttcgccaa    13140
ctattgcgat aacaagaaaa agccagcctt tcatgatata tctcccaatt tgtgtagggc    13200
ttattatgca cgcttaaaaa taataaaagc agacttgacc tgatagtttg gctgtgagca    13260
attatgtgct tagtgcatct aacgcttgag ttaagccgcg ccgcgaagcg gcgtcggctt    13320
gaacgaattg ttagacatta tttgccgact accttggtga tctcgccttt cacgtagtgg    13380
acaaattctt ccaactgatc tgcgcgcgag gccaagcgat cttcttcttg tccaagataa    13440
gcctgtctag cttcaagtat gacgggctga tactgggccg gcaggcgctc cattgcccag    13500
tcggcagcga catccttcgg cgcgattttg ccggttactg cgctgtacca aatgcgggac    13560
aacgtaagca ctacatttcg ctcatcgcca gccagtcgg gcggcgagtt ccatagcgtt    13620
aaggtttcat ttagcgcctc aaatagatcc tgttcaggaa ccggatcaaa gagttcctcc    13680
gccgctggac ctaccaaggc aacgctatgt tctcttgctt ttgtcagcaa gatagccaga    13740
tcaatgtcga tcgtggctgg ctcgaagata cctgcaagaa tgtcattgcg ctgccattct    13800
ccaaattgca gttcgcgctt agctggataa cgccacggaa tgatgtcgtc gtgcacaaca    13860
atggtgactt ctacagcgcg gagaatctcg ctctctccag gggaagccga agtttccaaa    13920
aggtcgttga tcaaagctcg ccgcgttgtt tcatcaagcc ttacggtcac cgtaaccagc    13980
```

-continued

| | | | | |
|---|---|---|---|---|
| aaatcaatat | cactgtgtgg | cttcaggccg | ccatccactg | cggagccgta caaatgtacg | 14040 |
| gccagcaacg | tcggttcgag | atggcgctcg | atgacgccaa | ctacctctga tagttgagtc | 14100 |
| gatacttcgg | cgatcaccgc | ttccctcatg | atgtttaact | ttgttttagg gcgactgccc | 14160 |
| tgctgcgtaa | catcgttgct | gctccataac | atcaaacatc | gacccacggc gtaacgcgct | 14220 |
| tgctgcttgg | atgcccgagg | catagactgt | accccaaaaa | aacagtcata acaagccatg | 14280 |
| aaaaccgcca | ctgcgccgtt | accaccgctg | cgttcggtca | aggttctgga ccagttgcgt | 14340 |
| gagcgcatac | gctacttgca | ttacagctta | cgaaccgaac | aggcttatgt ccactgggtt | 14400 |
| cgtgccttca | tccgtttcca | cggtgtgcgt | caccccggcaa | ccttgggcag cagcgaagtc | 14460 |
| gaggcatttc | tgtcctggct | ggcgaacgag | cgcaaggttt | cggtctccac gcatcgtcag | 14520 |
| gcattggcgg | ccttgctgtt | cttctacggc | aagtgctgtg | cacgatctg ccctggcttc | 14580 |
| aggagatcgg | aagacctcgg | ccgtccgggc | gcttgccggt | ggtgctgacc ccggatgaag | 14640 |
| tctctagagc | tctagagggt | tcgcatcctc | ggttttctgg | aaggcgagca tcgtttgttc | 14700 |
| gcccagcttc | tgtatggaac | gggcatgcgg | atcagtgagg | gtttgcaact gcgggtcaag | 14760 |
| gatctggatt | tcgatcacgg | cacgatcatc | gtgcgggagg | gcaagggctc caaggatcgg | 14820 |
| gccttgatgt | tacccgagag | cttggcaccc | agcctgcgcg | agcagggatc gataccgtgc | 14880 |
| ggctgcatga | aatcctggcc | ggtttgtctg | atgccaagct | ggcggcctgg ccggccagct | 14940 |
| tggccgctga | agaaaccgag | cgccgccgtc | taaaaaggtg | atgtgtattt gagtaaaaca | 15000 |
| gcttgcgtca | tgcggtcgct | gcgtatatga | tgcgatgagt | aaataaacaa atacgcaagg | 15060 |
| ggaacgcatg | aaggttatcg | ctgtacttaa | ccagaaaggc | gggtcaggca agacgaccat | 15120 |
| cgcaacccat | ctagcccgcg | ccctgcaact | cgccggggcc | gatgttctgt tagtcgattc | 15180 |
| cgatccccag | ggcagtgccc | gcgattgggc | ggccgtgcgg | gaagatcaac cgctaaccgt | 15240 |
| tgtcggcatc | gaccgcccga | cgattgaccg | cgacgtgaag | gccatcggcc ggcgcgactt | 15300 |
| cgtagtgatc | gacggagcgc | cccaggcggc | ggacttggct | gtgtccgcga tcaaggcagc | 15360 |
| cgacttcgtg | ctgattccgg | tgcagccaag | cccttacgac | atatgggcca ccgccgacct | 15420 |
| ggtggagctg | gttaagcagc | gcattgaggt | cacggatgga | aggctacaag cggcctttgt | 15480 |
| cgtgtcgcgg | gcgatcaaag | gcacgcgcat | cggcggtgag | gttgccgagg cgctggccgg | 15540 |
| gtacgagctg | cccattcttg | agtcccgtat | cacgcagcgc | gtgagctacc caggcactgc | 15600 |
| cgccgccggc | acaaccgttc | ttgaatcaga | acccgagggc | gacgctgccc gcgaggtcca | 15660 |
| ggcgctggcc | gctgaaatta | aatcaaaact | catttgagtt | aatgaggtaa agagaaaatg | 15720 |
| agcaaaagca | caaacacgct | aagtgccggc | cgtccgagcg | cacgcagcag caaggctgca | 15780 |
| acgttggcca | gcctggcaga | cacgccagcc | atgaagcggg | tcaactttca gttgccggcg | 15840 |
| gaggatcaca | ccaagctgaa | gatgtacgcg | gtacgccaag | gcaagaccat taccgagctg | 15900 |
| ctatctgaat | acatcgcgca | gctaccagag | taaatgagca | aatgaataaa tgagtagatg | 15960 |
| aattttagcg | gctaaaggag | gcggcatgga | aaatcaagaa | caaccaggca ccgacgccgt | 16020 |
| ggaatgcccc | atgtgtggag | gaacgggcgg | ttggccaggc | gtaagcggct gggttgtctg | 16080 |
| ccggccctgc | aatggcactg | gaaccccaa | gcccgaggaa | tcggcgtgac ggtcgcaaac | 16140 |
| catccggccc | ggtacaaatc | ggcgcggcgc | tgggtgatga | cctggtggag aagttgaagg | 16200 |
| ccgcgcaggc | cgcccagcgg | caacgcatcg | aggcagaagc | acgccccggt gaatcgtggc | 16260 |
| aagcggccgc | tgatcgaatc | cgcaaagaat | cccggcaacc | gccggcagcc ggtgcgccgt | 16320 |
| cgattaggaa | gccgcccaag | ggcgacgagc | aaccagattt | tttcgttccg atgctctatg | 16380 |

```
acgtgggcac cgcgatagt cgcagcatca tggacgtggc cgttttccgt ctgtcgaagc    16440
gtgaccgacg agctggcgag gtgatccgct acgagcttcc agacgggcac gtagaggttt    16500
ccgcagggcc ggccggcatg gccagtgtgt gggattacga cctggtactg atggcggttt    16560
cccatctaac cgaatccatg aaccgatacc gggaagggaa gggagacaag cccggccgcg    16620
tgttccgtcc acacgttgcg gacgtactca agttctgccg gcgagccgat ggcggaaagc    16680
agaaagacga cctggtagaa acctgcattc ggttaaacac cacgcacgtt gccatgcagc    16740
gtacgaagaa ggccaagaac ggccgcctgg tgacggtatc cgagggtgaa gccttgatta    16800
gccgctacaa gatcgtaaag agcgaaaccg ggcggccgga gtacatcgag atcgagctag    16860
ctgattggat gtaccgcgag atcacagaag gcaagaaccc ggacgtgctg acggttcacc    16920
ccgattactt tttgatcgat cccggcatcg gccgttttct ctaccgcctg gcacgccgcg    16980
ccgcaggcaa ggcagaagcc agatggttgt tcaagacgat ctacgaacgc agtggcagcg    17040
ccggagagtt caagaagttc tgtttcaccg tgcgcaagct gatcgggtca aatgacctgc    17100
cggagtacga tttgaaggag gaggcggggc aggctggccc gatcctagtc atgcgctacc    17160
gcaacctgat cgagggcgaa gcatccgccg gttcctaatg tacggagcag atgctagggc    17220
aaattgccct agcaggggaa aaaggtcgaa aaggtctctt tcctgtggat agcacgtaca    17280 ttggaaccc aaagccgtac attgggaacc ggaacccgta cattgggaac ccaaagccgt    17340
acattgggaa ccggtcacac atgtaagtga ctgatataaa agagaaaaaa ggcgattttt    17400
ccgcctaaaa ctctttaaaa cttattaaaa ctcttaaaac ccgcctggcc tgtgcataac    17460
tgtctggcca gcgcacagcc gaagagctgc aaaaagcgcc tacccttcgg tcgctgcgct    17520
ccctacgccc cgccgcttcg cgtcggccta tcgcggccgc tggccgctca aaaatggctg    17580
gcctacggcc aggcaatcta ccagggcgcg gacaagccgc ccgtcgcca ctcgaccgcc    17640 ggcgcccaca tcaaggcacc ctgcctcgcg cgtttcggtg atgacggtga aaacctctga    17700
cacatgcagc tcccggagac ggtcacagct tgtctgtaag cggatgccgg gagcagacaa    17760
gcccgtcagg gcgcgtcagc gggtgttggc gggtgtcggg gcgcagccat gacccagtca    17820
cgtagcgata gcggagtgta tactggctta actatgcggc atcagagcag attgtactga    17880
gagtgcacca tatgcggtgt gaaataccgc acagatgcgt aaggagaaaa taccgcatca    17940
ggcgctcttc cgcttcctcg ctcactgact cgctgcgctc ggtcgttcgg ctgcggcgag    18000
cggtatcagc tcactcaaag gcggtaatac ggttatccac agaatcaggg gataacgcag    18060
gaaagaacat gtgagcaaaa ggccagcaaa aggccaggaa ccgtaaaaag gccgcgttgc    18120
tggcgttttt ccataggctc cgcccccctg acgagcatca caaaaatcga cgctcaagtc    18180
agaggtggcg aaacccgaca ggactataaa gataccaggc gtttccccct ggaagctccc    18240
tcgtgcgctc tcctgttccg accctgccgc ttaccggata cctgtccgcc tttctccctt    18300
cgggaagcgt ggcgctttct catagctcac gctgtaggta tctcagttcg gtgtaggtcg    18360
ttcgctccaa gctgggctgt gtgcacgaac cccccgttca gcccgaccgc tgcgccttat    18420
ccggtaacta tcgtcttgag tccaacccgg taagacacga cttatcgcca ctggcagcag    18480
ccactggtaa caggattagc agagcgaggt atgtaggcgg tgctacagag ttcttgaagt    18540
ggtggcctaa ctacggctac actagaagga cagtatttgg tatctgcgct ctgctgaagc    18600
cagttacctt cggaaaaaga gttggtagct cttgatccgg caaacaaacc accgctggta    18660
gcggtggttt ttttgtttgc aagcagcaga ttacgcgcag aaaaaaagga tctcaagaag    18720
```

-continued

| | |
|---|---|
| atccggaaaa cgcaagcgca aagagaaagc aggtagcttg cagtgggctt acatggcgat | 18780 |
| agctagactg ggcggtttta tggacagcaa gcgaaccgga attgccagat tcgaagctcg | 18840 |
| gtcccgtggg tgttctgtcg tctcgttgta caacgaaatc cattcccatt ccgcgctcaa | 18900 |
| gatggcttcc cctcggcagt tcatcagggc taaatcaatc tagccgactt gtccggtgaa | 18960 |
| atgggctgca ctccaacaga acaatcaaa caaacataca cagcgactta ttcacacgcg | 19020 |
| aca | 19023 |

<210> SEQ ID NO 17
<211> LENGTH: 19020
<212> TYPE: DNA
<213> ORGANISM: Artificial Sequence
<220> FEATURE:
<223> OTHER INFORMATION: nucleotide sequence of pTEA6

<400> SEQUENCE: 17

| | |
|---|---|
| aattacaacg gtatatatcc tgccagtact gggcccctc gagggcgatc gcgcggccgc | 60 |
| ttcacggaaa gttgttatat ataagttcag taaataataa tgaaatataa attttaatta | 120 |
| tatctagtac tcaataagaa gatggagaaa gttatgttaa ttatagttat aaattattta | 180 |
| taaatttaat atatatatat aaagaaaata gttgtataac taataattat ttttacaata | 240 |
| ctttatatag ttatatttaa aaaaatttta aaattaaaat actattttt tgttcaatat | 300 |
| attaatattt atattattta atttattatt gaatatgaat aaatttttt tgaaaattat | 360 |
| attttaatt tttagaaatt ttatataact ttccatatat atatttctga tttgtcaatt | 420 |
| tcttttgaga tttatctaaa ttgatttgaa tttttttat ttttaaaaaa taaaataatt | 480 |
| ttaaaatttc ttggaatttt atataaattt ttggattttt caaaaaaaat tgagatttt | 540 |
| ttcttttttt tcgatttttt aaatttattt caggaaaata taaactaact tttctttgct | 600 |
| ttgggtataa ttaatattag ataacccaca aattagatca ataggagctt catgtcctaa | 660 |
| tcccatttaa ttacttttgt tgtatcatta atttagtcga ccttacatag tagctctatg | 720 |
| gggcaaatag ttataaatgt taaattagta tttaaatctt gaagttttta atttaaagtt | 780 |
| cagactatta gtattatatc aaatatttaa gggtaaatat atattctaat atctaagctt | 840 |
| gggtcaaggt ttaaattaag tacttaaact tggttttata gttcaaattg atttaaataa | 900 |
| ctaagtatta atttgaatta agaagcaaag ttcaagtacc taattagact ataaaaaaaa | 960 |
| cttttgctag taaattgaac cttaaagtcg agtttagtta tctaattgga caaaaaaatc | 1020 |
| ttaaatacca atttaaaccc taaagtcaag tttaggtacc aaagtgtata tttatctaat | 1080 |
| atttaaattt gatccaccta atttaaattt ttttggtcca atgcaataag agaattaatt | 1140 |
| aatacttaca cacatgatag agatataccc acaacagata cacactacaa aaaacattaa | 1200 |
| aaaatagaaa gatatatttc ctacaaaatt taaaagcatt taattttta actaacatta | 1260 |
| gacaaatgga aatggaaaga cttatttta agtttatgga tgaatctaat ttatctaaac | 1320 |
| attgggtttt ttttttttgt gacgaaatat gggtgagaga aggtagtaag ctaagtaggg | 1380 |
| gagtaatatc tcaaacaaat aattaaaaaa ctcctttaaa tgtggctata aatacctgaa | 1440 |
| accaatcctt ctttcctcaa ctcaaatctt caatctttag atcatctctc caaaaaaata | 1500 |
| ccatgagtaa acggaatccg aagattctga agatttttct gtatatgtta cttctcaact | 1560 |
| ctctcttttct catcatctac ttcgttttc actcatcgtc gttttcagag tccagaatca | 1620 |
| gcaaccggtt atcgagttcc gccacaagga cggtacgagc cttcagaaat cgatgtcatg | 1680 |
| ccaggccagg gacaccggga tcgagttacg gaaatgcgag gcgaccgctt ccctcggcac | 1740 |

```
cagcgccttt acactacaat agcccaagtc gcgcagcgag tcattatcca cggtaccatg    1800
gaggttatgc ggacgacgtg acagttagca tgggaccgga cgacgatcgt acagatatct    1860
ttggccccga aaccgatctc agcgaaacgc gccacctcaa cgacgcatac gggtttcggt    1920
catcccagat caccctcagc gaagatcccc acggcaccca cgcgcgttcc cggtacgacg    1980
acgaagacga tgtgagcacc acttattcct ccaacacggg caccagcgct tcaggtgtcg    2040
acaagttcga gcattacggt cccattccgg aggaaggcaa gcacgagcgg cgcggcgtgc    2100
gaccaccaca gatgtcgagg aaggaagtcc agctcatcaa cggcgaactc gttctcgagt    2160
gcaagattcc gactatattg tattcgtttt tgcccaggag agacgaagtg gagtttacgc    2220
acatgcggta cacagccgtc acttgtgacc ctgatgactt tgttgccagg ggttacaagt    2280
tgcgccagaa tatcggtcgt accgccaggg agacggagtc gttcatctgc gtgaccatgt    2340
acaacgagga cgagttcgga ttcacacgga ctatgcacgc agtgatgaag aacatttcgc    2400
atttttgttc ccgaaacaag agtaggacgt ggggagcgga tgggtggcag aagattgtgg    2460
tctgtgtggt ttcggatgga cgagagatca ttcaccccg gaccttggac gccctcgcag    2520
ccatgggcgt ttaccagcac ggtatcgcca agaactttgt caaccagaag gcggtgcagg    2580
cccacgttta cgagtacacg acacaagtgt ctctggacag cgacctcaag ttcaagggcg    2640
ccgagaaggg catcgtgccc tgccagatga tttttttgctt gaaggagaag aaccaaaaga    2700
aactcaactc gcatagatgg ttcttcaacg cctttggcaa agccttgaac ccgaatgtgt    2760
gtatcctcct agacgtcggc acccgccccg gcggcacaag tctctaccat ctctggaaag    2820
ccttcgacac ggattccaac gtggcggggg cctgcgggga atcaaagcg atgaaggggc    2880 ggtttggcgg gaatttgctc aaccctctgg tggctagtca gaactttgag tacaagatga    2940
gcaatattct ggacaaaccg ttggagtcgg tgtttgggta catcacggtg ttgccgggcg    3000
ccttgtcggc gtatcggtac catgcgctgc agaacgatga gacgggccat gggccgttga    3060
gtcagtattt caagggcgag acgctccatg ggcagcacgc ggatgtgttt acggcgaaca    3120
tgtacttggc cgaggaccga attcgtgtgtt gggagttggt ggccaagagg ggtgagaggt    3180
gggtgttgaa gtatgtgaag gggtgtacgg gtgagacgga tgtgcctgac accgtcccgg    3240
aattcgtctc gcaacgtcgt cgttggctca acggtgcctt cttcgccgcc gtctactccc    3300
tcgtccactt tcgacaaatc tggaaaaccg accacacctt tatgcgcaaa gcccttctcc    3360
acgtcgaatt cctctaccac ctcctgcaac tcctcttcac ctacttctcc ctggccaact    3420
tctacctcgc cttctacttt atcgccggcg gactcgccga tccccacgtc gaccttttta    3480
actcggacgg ccacgtcgcg cgcatcatct tcaacatcct ccgctacgtc tgcgtcctgc    3540
tgatctgcac acaattcatc ttgtccctcg gcaaccgtcc gcagggtgcc aaaagaatgt    3600
atctcgcatc catgatcatc tacgccgtca tcatggtgta caccaccttc gccaccatct    3660
tcatcgtcgt gcgacaaatc caaccctctc aaaaatccga cgacaagccc gacctcgaac    3720
tcggcaacaa cgtcttcacc aacctgatcg tctccgtggc tagtaccctc gggctctact    3780
tcgtcatgtc cttttctctat ctcgacccct ggcacatgtt cacctcggcc atccagtact    3840
ttgtcctgct gccttcctac atctgcacgc tccagatcta cgccttttgc aacacccacg    3900
acgtcacatg gggcaccaaa ggcgacaacg tgatgcgcac cgatctcgga ggcgccattg    3960
gcaagggaag caccgtcgaa ctggaaatgc cttcggacca actcgacatc gactcggat    4020 acgacgaatg tctacgaaat ctccgggatc gcgtcatggt ccctgccgtt cccgtgtccg    4080
```

```
aggaccagct gcagcaggat tactacaagt cggtgcgcac gtacatggtg gtgtcgtgga      4140
tggtggccaa cgcgacgctg gccatggcgg tgtcggaagc gtatggcgat tcggaaattg      4200
gggataattt ttacttgcgg tttatcctgt gggcggtggc ggccctggcg ctgtttagag      4260
cgttggggtc gacgacgttt gcggcgatta atctggtgag tgctctcgtg gagggcaggg      4320
tcaggctgag gttgaatatg aaagggttta ggtggattaa ggagaagtgg ggggatgcgg      4380
atgtgaaggg caagtttgag gggttggggg atcgggcgag ggggttggcg aggcggtgag      4440
agctccctag ggacgccggt gaagaggcag tgcaagacgt ttaaacgcta gcaagcttgg      4500
acacgctgaa atcaccagtc tctctctaca aatctatctc tctctatttt ctccataata      4560
atgtgtgagt agttcccaga taagggaatt agggttccta tagggtttcg ctcatgtgtt      4620
gagcatataa gaaccctta gtatgtattt gtatttgtaa atacttcta tcaataaaat        4680 ttctaattcc taaaaccaaa atccagtact aaaatccaga tcatgcatgg tacagcacgc      4740
gtcctgcagg cccgggttaa ttaagcggcc gcttcacgga agttgttat atataagttc       4800 agtaaataat aatgaaatat aaatttaat tatatctagt actcaataag aagatggaga       4860
aagttatgtt aattatagtt ataaattatt tataaattta atatatatat ataagaaaa       4920 tagttgtata actaataatt attttacaa tactttatat agttatattt aaaaaaattt       4980
taaaattaaa atactattat tttgttcaat atattaatat ttatattatt taatttatta     5040
ttgaatatga ataaattttt tttgaaaatt atatttttaa tttttagaaa ttttatataa      5100
ctttccatat atatatttct gatttgtcaa tttcttttga gatttatcta aattgatttg      5160 aattttttt atttttaaaa aataaaataa ttttaaaatt tcttggaatt ttatataaat       5220
ttttggattt ttcaaaaaaa attgagattt ttttctttt tttcgatttt ttaaatttat       5280
ttcaggaaaa tataaactaa cttttctttg ctttgggtat aattaatatt agataaccca      5340
caaattagat caataggagc ttcatgtcct aatcccattt aattactttt gttgtatcat      5400
taatttagtc gaccttacat agtagctcta tgggcaaat agttataaat gttaaattag       5460
tatttaaatc ttgaagtttt taatttaaag ttcagactat tagtattata tcaaatattt      5520
aagggtaaat atatattcta atatctaagc ttgggtcaag gttaaatta agtacttaaa       5580 cttggtttta tagttcaaat tgatttaaat aactaagtat taatttgaat taagaagcaa      5640
agttcaagta cctaattaga ctataaaaaa aacttttgct agtaaattga acctaaagt       5700 cgagtttagt tatctaattg gacaaaaaaa tcttaaatac caatttaaac cctaaagtca      5760
agtttaggta ccaaagtgta tatttatcta atatttaaat ttgatccacc taatttaaat     5820
ttttttggtc caatgcaata agagaattaa ttaatactta cacacatgat agagatatac      5880
ccacaacaga tacacactac aaaaaacatt aaaaaaataga aagatatatt tcctacaaaa    5940
tttaaaagca tttaattttt taactaacat tagacaaatg gaaatggaaa gacttatttt      6000
taagtttatg gatgaatcta atttatctaa acattgggtt ttttttttt gtgacgaaat      6060 atgggtgaga gaaggtagta agctaagtag gggagtaata tctcaaacaa ataattaaaa      6120 aactcctta aatgtggcta taaatacctg aaaccaatcc ttctttcctc aactcaaatc      6180 ttcaatctt agatcatctc tccaaaaaaa taccatgtgc ggaattgttg gtgctatcgc       6240
ccaaagagac gttgctgaga ttttgttaga gggtctgcga aggctagagt atagaggata      6300
tgactccgct ggtctggctg tcgttgatgc tgagggtcat atgacaaggc taagaaggtt      6360
aggaaaggtt cagatgcttg ctcaggcagc tgaggaacac ccattgcatg gaggtactgg      6420
tattgcacat accaggtggg ctactcatgg ggagccatca gaagttaatg ctcatccaca      6480
```

```
tgtgagtgag catatcgttg tagttcacaa tgggataatt gaaaaccacg aaccattgag    6540
ggaagagtta aaggcaagag gatatacttt tgtgagtgag actgacactg aggttattgc    6600
acatttagtg aactgggaac tcaaacaggg gggcacattg cgtgaggctg tgttaagagc    6660
tattcctcaa cttagaggtg catacggtac tgttattatg gattcaagac acccagatac    6720
tctccttgca gctagatcag gtagtccctt ggtcatagga cttggaatgg gtgaaaattt    6780
tatcgctagc gaccaattgg ccttattgcc agttacaaga cgatttattt tccttgaaga    6840
gggcgatatt gctgagatta ctagaaggtc tgtgaacatc tttgataaga ctggcgctga    6900
ggttaaacgt caggatatcg agtctaacct tcaatacgat gctggtgata aaggaattta    6960
caggcattat atgcaaaagg aaatttatga acaaccaaat gctatcaaaa acacacttac    7020
tggccgtatt tctcatggac aggtcgattt aagcgagctt ggtcctaatg cagacgaact    7080
gctatcaaaa gttgagcaca tacagatact ggcatgcgga actagttata attcaggaat    7140
ggtgtctaga tactggttcg aaagcttggc aggtatacct tgtgatgtag agatcgcttc    7200
tgagtttagg tatagaaagt ctgctgtgcg tagaaattca ttaatgatta cattatctca    7260
atccggagaa acagcagata cactggctgg attgaggctt tctaaggaac tcggatatct    7320
gggttcactt gctatttgta atgtaccagg ttcctcattg gttcgtgaat cagatctagc    7380
acttatgaca aatgcaggaa ctgaaatagg tgtggcaagt accaaggctt cacaaccca     7440
actgaccgta cttttaatgt tggtagcaaa actcagtcga ttaaaggggc tagatgcatc    7500
tatcgaacat gatattgttc acgggcttca agctctccct tcaagaattg aacaaatgct    7560
ttcacaagat aagagaatag aggcattggc tgaagatttt tccgacaaac atcacgcatt    7620
gtttcttgga cgtggcgatc aatatccaat tgcattggaa ggagctttga agttgaaaga    7680
aataagttac attcacgcag aagcatatgc agctggagaa ctcaagcatg gtcctttggc    7740
actcatcgac gctgacatgc ccgtgatcgt agtggctcct aataacgaac tgctcgaaaa    7800
gcttaaatca aatatcgaag aggttcgagc tagaggaggt cagctttacg ttttcgctga    7860
acaagatgct ggattcgtgt caagcgataa tatgcatata attgaaatgc ctcacgttga    7920
agaagtgatt gcacctatat tttatacagt cccattgcaa cttctagctt accatgttgc    7980
acttattaaa ggaactgatg ttgatcagcc tagaaaccta gcaaaatctg taacagtcga    8040
ataaacgcgt aaggagtttg tgcgtgaatc taattgaggc ctgtttaaac ggcgcgcccc    8100
cgatccgcgt ttgtgttttc tgggtttctc acttaagcgt ctgcgtttta cttttgtatt    8160
gggtttggcg tttagtagtt tgcggtagcg ttcttgttat gtgtaattac gcttttttctt    8220
cttgcttcag cagtttcggt tgaaatataa atcgaatcaa gtttcacttt atcagcgttg    8280
ttttaaattt tggcattaaa ttggtgaaaa ttgcttcaat tttgtatcta aatagaagag    8340
acaacatgaa attcgacttt tgacctcaaa tcttcgaaca tttatttcct gatttcacga    8400
tggatgagga taacgaaagg gcggttccta tgtccgggaa agttcccgta gaagacaatg    8460
agcaaagcta ctgaaacgcg gacacgacgt cgcattggta cggatatgag ttaaaccgac    8520
tcaattcctt tattaagaca taaaccgatt ttggttaaag tgtaacagtg agctgatata    8580
aaaccgaaac aaaccggtac aagtttgatt gagcaacttg atgacaaact tcagaatttt    8640
ggttattgaa tgaaaatcat agtctaatcg taaaaaatgt acagaagaaa agctagagca    8700
gaacaaagat tctatattct ggttccaatt tatcatcgct ttaacgtccc tcagatttga    8760
tcggggaatt cgatatcatt accctgttat ccctaaagct tattaatgtt tgtcgaggag    8820
```

```
aaatatgagt cgaggcatgg atacactaag ttcccctgaa gtgagcatga tctttgatgc    8880
tgagatgatt cccagagcaa gatagtttgt gctgcaagtg acacaattgt aatgaaacca    8940
ccactcaacg aatttacttg tggctttgac atgtcgtgtg ctctgtttgt atttgtgagt    9000
gccggttggt aattattttt gttaatgtga ttttaaaacc tcttatgtaa atagttactt    9060
tatctattga agtgtgttct tgtggtctat agtttctcaa agggaaatta aaatgttgac    9120
atcccattta caattgataa cttggtatac acaaactttg taaatttggt gatatttatg    9180
gtcgaaagaa ggcaataccc attgtatgtt ccaatatcaa tatcaatacg ataacttgat    9240
aatactaaca tatgattgtc attgtttttc cagtatcaat atacattaag ctactacaaa    9300
attagtataa atcactatat tataaatctt tttcggttgt aacttgtaat tcgtgggttt    9360
ttaaaataaa agcatgtgaa aattttcaaa taatgtgatg gcgcaatttt attttccgag    9420
ttccaaaata ttgccgcttc attaccctaa tttgtggcgc cacatgtaaa acaaaagacg    9480
attcttagtg gctatcactg ccatcacgcg gatcactaat atgaaccgtc gattaaaaca    9540
gatcgacggt ttatacatca ttttattgta cacacggatc gatatctcag ccgttagatt    9600
taatatgcga tctgattgct caaaaaatag actctccgtc tttgcctata aaaacaattt    9660
cacatctttc tcacccaaat ctactcttaa ccgttcttct tcttctacag acatcaattt    9720
ctctcgactc tagaggatcc aagcttatcg atttcgaacc cctcaggcga agaacaggta    9780
tgatttgttt gtaattagat caggggttta ggtcttccca ttactttta atgtttttc     9840
tgttactgtc tccgcgatct gattttacga caatagagtt tcgggttttg tcccattcca    9900
gtttgaaaat aaaggtccgt cttttaagtt tgctggatcg ataaacctgt gaagattgag    9960
tctagtcgat ttattggatg atccattctt catcgttttt tcttgcttc gaagttctgt     10020
ataaccagat ttgtctgtgt gcgattgtca ttacctagcc gtgtatcgag aactaggggtt    10080
ttcgagtcaa ttttgcccct tttggttata tctggttcga taacgattca tctggattag    10140
ggtttaagt ggtgacgttt agtattccaa tttcttcaaa atttagttat ggataatgaa      10200
aatccccaat tgactgttca atttcttgtt aaatgcgcag atcacaatgg cttcgatctc    10260
ctcctcagtc gcgaccgtta gccggaccgc ccctgctcag gccaacatgg tggctccgtt    10320
caccggcctt aagtccaacg ccgccttccc caccaccaag aaggctaacg acttctccac    10380
ccttcccagc aacggtggaa gagttcaatg tatgcaggtg tggccggcct acggcaacaa    10440
gaagttcgag acgctgtcgt acctgccgcc gctgtctatg gcgcccaccg tgatgatggc    10500
ctcgtcggcc accgccgtcg ctccgttcca ggggctcaag tccaccgcca gcctccccgt    10560
cgcccgccgc tcctccagaa gcctcggcaa cgtcagcaac ggcggaagga tccggtgcat    10620
ggccggcgcc gaggagatcg tgctgcagcc catcaaggag atctccggca ccgtcaagct    10680
gccggggtcc aagtcgcttt ccaaccggat cctcctactc gccgccctgt ccgaggggac    10740
aacagtggtt gataacctgc tgaacagtga ggatgtccac tacatgctcg ggcccttgag    10800
gactcttggt ctctctgtcg aagcggacaa agctgccaaa agagctgtag ttgttggctg    10860
tggtggaaag ttcccagttg aggatgctaa agaggaagtg cagctcttct tggggaatgc    10920
tggaatcgca atgcggtcct tgacagcagc tgttactgct gctggtggaa atgcaactta    10980
cgtgcttgat ggagtaccaa gaatgaggga gagacccatt ggcgacttgg ttgtcggatt    11040
gaagcagctt ggtgcagatg ttgattgttt ccttggcact gactgccac ctgttcgtgt      11100
caatggaatc ggagggctac ctggtggcaa ggtcaagctg tctggctcca tcagcagtca    11160
gtacttgagt gccttgctga tggctgctcc tttggctctt ggggatgtgg agattgaaat    11220
```

```
cattgataaa ttaatctcca ttccgtacgt cgaaatgaca ttgagattga tggagcgttt    11280
tggtgtgaaa gcagagcatt ctgatagctg ggacagattc tacattaagg gaggtcaaaa    11340
atacaagtcc cctaaaaatg cctatgttga aggtgatgcc tcaagcgcaa gctatttctt    11400
ggctggtgct gcaattactg gagggactgt gactgtggaa ggttgtggca ccaccagttt    11460
gcagggtgat gtgaagtttg ctgaggtact ggagatgatg ggagcgaagg ttacatggac    11520
cgagactagc gtaactgtta ctggcccacc gcgggagcca tttgggagga aacacctcaa    11580
ggcgattgat gtcaacatga acaagatgcc tgatgtcgcc atgactcttg ctgtggttgc    11640
cctctttgcc gatggcccga cagccatcag agacgtggct tcctggagag taaaggagac    11700
cgagaggatg gttgcgatcc ggacggagct aaccaagctg ggagcatctg ttgaggaagg    11760
gccggactac tgcatcatca cgccgccgga gaagctgaac gtgacggcga tcgacacgta    11820
cgacgaccac aggatggcga tggctttctc ccttgccgcc tgtgccgagg tccccgtcac    11880
catccgggac cctgggtgca cccggaagac cttccccgac tacttcgatg tgctgagcac    11940
tttcgtcaag aattaagctc tagaactagt ggatccccccg atccgcgttt gtgttttctg    12000
ggtttctcac ttaagcgtct gcgttttact tttgtattgg gtttggcgtt tagtagtttg    12060
cggtagcgtt cttgttatgt gtaattacgc ttttttcttct tgcttcagca gtttcggttg    12120
aaatataaat cgaatcaagt ttcactttat cagcgttgtt ttaaattttg gcattaaatt    12180
ggtgaaaatt gcttcaattt tgtatctaaa tagaagagac aacatgaaat tcgacttttg    12240
acctcaaatc ttcgaacatt tatttcctga tttcacgatg gatgaggata acgaaagggc    12300
ggttcctatg tccgggaaag ttcccgtaga agacaatgag caaagctact gaaacgcgga    12360
cacgacgtcg cattggtacg gatatgagtt aaaccgactc aattcctttta ttaagacata    12420 aaccgatttt ggttaaagtg taacagtgag ctgatataaa accgaaacaa accggtacaa    12480
gtttgattga gcaacttgat gacaaacttc agaattttgg ttattgaatg aaaatcatag    12540
tctaatcgta aaaaatgtac agaagaaaag ctagagcaga acaaagattc tatattctgg    12600
ttccaattta tcatcgcttt aacgtccctc agatttgatc gggaaaccaa aacgtcgtga    12660
gacagtttgg ttaactataa cggtcctaag gtagcgatcg aggcattacg gcattacggc    12720
actcgcgagg gtccgaattc gagcatggag ccatttacaa ttgaatatat cctgccgccg    12780
ctgccgcttt gcacccggtg gagcttgcat gttggtttct acgcagaact gagccggtta    12840
ggcagataat ttccattgag aactgagcca tgtgcacctt cccccccaaca cggtgagcga    12900 cggggcaacg gagtgatcca catgggactt ttaaacatca tccgtcggat ggcgttgcga    12960
gagaagcagt cgatccgtga gatcagccga cgcaccgggc aggcgcgcaa cacgatcgca    13020
aagtatttga acgcaggtac aatcgagccg acgttcacgg taccggaacg accaagcaag    13080
ctagcttagt aaagcccctcg ctagatttta atgcggatgt tgcgattact tcgccaacta    13140
ttgcgataac aagaaaaagc cagccttttca tgatatatct cccaatttgt gtagggctta    13200
ttatgcacgc ttaaaaataa taaaagcaga cttgacctga tagtttggct gtgagcaatt    13260
atgtgcttag tgcatctaac gcttgagtta agccgcgccg cgaagcggcg tcggcttgaa    13320
cgaattgtta gacattattt gccgactacc ttggtgatct cgccttttcac gtagtggaca    13380 aattcttcca actgatctgc gcgcgaggcc aagcgatctt cttcttgtcc aagataagcc    13440
tgtctagctt caagtatgac gggctgatac tgggccggca ggcgctccat tgcccagtcg    13500
gcagcgacat ccttcggcgc gattttgccg gttactgcgc tgtaccaaat gcgggacaac    13560
```

```
gtaagcacta catttcgctc atcgccagcc cagtcgggcg gcgagttcca tagcgttaag    13620
gtttcattta gcgcctcaaa tagatcctgt tcaggaaccg gatcaaagag ttcctccgcc    13680
gctggaccta ccaaggcaac gctatgttct cttgcttttg tcagcaagat agccagatca    13740
atgtcgatcg tggctggctc gaagatacct gcaagaatgt cattgcgctg ccattctcca    13800
aattgcagtt cgcgcttagc tggataacgc cacggaatga tgtcgtcgtg cacaacaatg    13860
gtgacttcta cagcgcggag aatctcgctc tctccagggg aagccgaagt ttccaaaagg    13920
tcgttgatca aagctcgccg cgttgtttca tcaagcctta cggtcaccgt aaccagcaaa    13980
tcaatatcac tgtgtggctt caggccgcca tccactgcgg agccgtacaa atgtacggcc    14040
agcaacgtcg gttcgagatg cgctcgatg acgccaacta cctctgatag ttgagtcgat     14100
acttcggcga tcaccgcttc cctcatgatg tttaactttg ttttagggcg actgccctgc    14160
tgcgtaacat cgttgctgct ccataacatc aaacatcgac ccacggcgta acgcgcttgc    14220
tgcttggatg cccgaggcat agactgtacc ccaaaaaaac agtcataaca agccatgaaa    14280
accgccactg cgccgttacc accgctgcgt tcggtcaagg ttctggacca gttgcgtgag    14340
cgcatacgct acttgcatta cagcttacga accgaacagg cttatgtcca ctgggttcgt    14400
gccttcatcc gtttccacgg tgtgcgtcac ccggcaacct tgggcagcag cgaagtcgag    14460
gcatttctgt cctggctggc gaacgagcgc aaggtttcgg tctccacgca tcgtcaggca    14520
ttggcggcct tgctgttctt ctacggcaag tgctgtgcac ggatctgccc tggcttcagg    14580
agatcggaag acctcggccg tccgggcgct tgccggtggt gctgaccccg gatgaagtct    14640
ctagagctct agagggttcg catcctcggt tttctggaag gcgagcatcg tttgttcgcc    14700
cagcttctgt atggaacggg catgcggatc agtgagggtt tgcaactgcg ggtcaaggat    14760
ctggatttcg atcacggcac gatcatcgtg cgggagggca agggctccaa ggatcgggcc    14820
ttgatgttac ccgagagctt ggcacccagc ctgcgcgagc agggatcgat accgtgcggc    14880
tgcatgaaat cctggccggt ttgtctgatg ccaagctggc ggcctggccg gccagcttgg    14940
ccgctgaaga aaccgagcgc cgccgtctaa aaaggtgatg tgtatttgag taaaacagct    15000
tgcgtcatgc ggtcgctgcg tatatgatgc gatgagtaaa taaacaaata cgcaagggga    15060
acgcatgaag gttatcgctg tacttaacca gaaaggcggg tcaggcaaga cgaccatcgc    15120
aacccatcta gcccgcgccc tgcaactcgc cggggccgat gttctgttag tcgattccga    15180
tccccagggc agtgcccgcg attgggcggc cgtgcgggaa gatcaaccgc taaccgttgt    15240
cggcatcgac cgcccgacga ttgaccgcga cgtgaaggcc atcggccggc gcgacttcgt    15300
agtgatcgac ggagcgcccc aggcggcgga cttggctgtg tccgcgatca aggcagccga    15360
cttcgtgctg attccggtgc agccaagccc ttacgacata tggccaccg ccgacctggt     15420
ggagctggtt aagcagcgca ttgaggtcac ggatggaagg ctacaagcgg cctttgtcgt    15480
gtcgcgggcg atcaaaggca cgcgcatcgg cggtgaggtt gccgaggcgc tggccgggta    15540
cgagctgccc attcttgagt cccgtatcac gcagcgcgtg agctacccag gcactgccgc    15600
cgccggcaca accgttcttg aatcagaacc cgagggcgac gctgcccgcg aggtccaggc    15660
gctggccgct gaaattaaat caaaactcat ttgagttaat gaggtaaaga gaaaatgagc    15720
aaaagcacaa acacgctaag tgccggccgt ccgagcgcac gcagcagcaa ggctgcaacg    15780
ttggccagcc tggcagacac gccagccatg aagcgggtca ctttcagtt gccggcggag     15840
gatcacacca gctgaagat gtacgcgta cgccaaggca agaccattac cgagctgcta     15900
tctgaataca tcgcgcagct accagagtaa atgagcaaat gaataaatga gtagatgaat    15960
```

```
tttagcggct aaaggaggcg gcatggaaaa tcaagaacaa ccaggcaccg acgccgtgga   16020
atgccccatg tgtggaggaa cgggcggttg gccaggcgta agcggctggg ttgtctgccg   16080
gccctgcaat ggcactggaa cccccaagcc cgaggaatcg gcgtgacggt cgcaaaccat   16140
ccggcccggt acaaatcggc gcggcgctgg gtgatgacct ggtggagaag ttgaaggccg   16200
cgcaggccgc ccagcggcaa cgcatcgagg cagaagcacg ccccggtgaa tcgtggcaag   16260
cggccgctga tcgaatccgc aaagaatccc ggcaaccgcc ggcagccggt gcgccgtcga   16320
ttaggaagcc gcccaagggc gacgagcaac cagatttttt cgttccgatg ctctatgacg   16380
tgggcacccg cgatagtcgc agcatcatgg acgtggccgt tttccgtctg tcgaagcgtg   16440
accgacgagc tggcgaggtg atccgctacg agcttccaga cgggcacgta gaggtttccg   16500
cagggccggc cggcatggcc agtgtgtggg attacgacct ggtactgatg gcggtttccc   16560
atctaaccga atccatgaac cgataccggg aagggaaggg agacaagccc ggccgcgtgt   16620
tccgtccaca cgttgcggac gtactcaagt tctgccggcg agccgatggc ggaaagcaga   16680
aagacgacct ggtagaaacc tgcattcggt taaacaccac gcacgttgcc atgcagcgta   16740
cgaagaaggc caagaacggc cgcctggtga cggtatccga gggtgaagcc ttgattagcc   16800
gctacaagat cgtaaagagc gaaaccgggc ggccggagta catcgagatc gagctagctg   16860
attggatgta ccgcgagatc acagaaggca agaacccgga cgtgctgacg gttcaccccg   16920
attactttt gatcgatccc ggcatcggcc gttttctcta ccgcctggca cgccgcgccg   16980
caggcaaggc agaagccaga tggttgttca agacgatcta cgaacgcagt ggcagcgccg   17040
gagagttcaa gaagttctgt ttcaccgtgc gcaagctgat cgggtcaaat gacctgccgg   17100
agtacgattt gaaggaggag gcggggcagg ctggcccgat cctagtcatg cgctaccgca   17160
acctgatcga gggcgaagca tccgccggtt cctaatgtac ggagcagatg ctagggcaaa   17220
ttgccctagc aggggaaaaa ggtcgaaaag gtctctttcc tgtggatagc acgtacattg   17280
ggaacccaaa gccgtacatt gggaaccgga accgtacat tgggaaccca agccgtaca   17340
ttgggaaccg gtcacacatg taagtgactg atataaaaga gaaaaaaggc gatttttccg   17400
cctaaaactc tttaaaactt attaaaactc ttaaaacccg cctggcctgt gcataactgt   17460
ctggccagcg cacagccgaa gagctgcaaa aagcgcctac ccttcggtcg ctgcgctccc   17520
tacgccccgc cgcttcgcgt cggcctatcg cggccgctgg ccgctcaaaa atggctggcc   17580
tacggccagg caatctacca gggcgcggac aagccgcgcc gtcgccactc gaccgccggc   17640
gcccacatca aggcaccctg cctcgcgcgt ttcggtgatg acggtgaaaa cctctgacac   17700
atgcagctcc cggagacggt cacagcttgt ctgtaagcgg atgccgggag cagacaagcc   17760
cgtcagggcg cgtcagcggg tgttggcggg tgtcggggcg cagccatgac ccagtcacgt   17820
agcgatagcg gagtgtatac tggcttaact atgcggcatc agagcagatt gtactgagag   17880
tgcaccatat gcggtgtgaa ataccgcaca gatgcgtaag gagaaaatac cgcatcaggc   17940
gctcttccgc ttcctcgctc actgactcgc tgcgctcggt cgttcggctg cggcgagcgg   18000
tatcagctca ctcaaaggcg gtaatacggt tatccacaga atcaggggat aacgcaggaa   18060
agaacatgtg agcaaaaggc cagcaaaagg ccaggaaccg taaaaaggcc gcgttgctgg   18120
cgttttccca taggctccgc cccctgacg agcatcacaa aaatcgacgc tcaagtcaga   18180
ggtggcgaaa cccgacagga ctataaagat accaggcgtt tccccctgga agctccctcg   18240
tgcgctctcc tgttccgacc ctgccgctta ccggatacct gtccgccttt ctcccttcgg   18300
```

-continued

```
gaagcgtggc gctttctcat agctcacgct gtaggtatct cagttcggtg taggtcgttc    18360
gctccaagct gggctgtgtg cacgaacccc ccgttcagcc cgaccgctgc gccttatccg    18420
gtaactatcg tcttgagtcc aacccggtaa gacacgactt atcgccactg gcagcagcca    18480
ctggtaacag gattagcaga gcgaggtatg taggcggtgc tacagagttc ttgaagtggt    18540
ggcctaacta cggctacact agaaggacag tatttggtat ctgcgctctg ctgaagccag    18600
ttaccttcgg aaaaagagtt ggtagctctt gatccggcaa acaaaccacc gctggtagcg    18660
gtggtttttt tgtttgcaag cagcagatta cgcgcagaaa aaaggatctc aagaagatc    18720 cggaaaacgc aagcgcaaag agaaagcagg tagcttgcag tgggcttaca tggcgatagc    18780
tagactgggc ggttttatgg acagcaagcg aaccggaatt gccagattcg aagctcggtc    18840
ccgtgggtgt tctgtcgtct cgttgtacaa cgaaatccat tcccattccg cgctcaagat    18900
ggcttcccct cggcagttca tcagggctaa atcaatctag ccgacttgtc cggtgaaatg    18960
ggctgcactc caacagaaac aatcaaacaa acatacacag cgacttattc acacgcgaca    19020
```

<210> SEQ ID NO 18
<211> LENGTH: 30
<212> TYPE: DNA
<213> ORGANISM: Artificial Sequence
<220> FEATURE:
<223> OTHER INFORMATION: target sequence of the miR403-interacting site
      in Arabidopsis AGO2 mRNA

<400> SEQUENCE: 18
aaggagtttg tgcgtgaatc taattgggtt                                      30

<210> SEQ ID NO 19
<211> LENGTH: 22
<212> TYPE: DNA
<213> ORGANISM: Artificial Sequence
<220> FEATURE:
<223> OTHER INFORMATION: miR403 from A. thaliana

<400> SEQUENCE: 19
gctcaaacac gcacttagat ta                                              22

<210> SEQ ID NO 20
<211> LENGTH: 21
<212> TYPE: DNA
<213> ORGANISM: Artificial Sequence
<220> FEATURE:
<223> OTHER INFORMATION: minor form of Ghi_miR408

<400> SEQUENCE: 20
tgcactgcct cttccctggc t                                               21

<210> SEQ ID NO 21
<211> LENGTH: 21
<212> TYPE: DNA
<213> ORGANISM: Artificial Sequence
<220> FEATURE:
<223> OTHER INFORMATION: alternative form of Ghi_miRcan1230(2)

<400> SEQUENCE: 21
tttgcatgac actactttaa a                                               21

<210> SEQ ID NO 22
<211> LENGTH: 21
<212> TYPE: DNA
<213> ORGANISM: Artificial Sequence
<220> FEATURE:

<223> OTHER INFORMATION: alternative form miRcan1230(3)

<400> SEQUENCE: 22
tgtggctttg catgacacta c                                              21

<210> SEQ ID NO 23
<211> LENGTH: 34
<212> TYPE: DNA
<213> ORGANISM: Artificial Sequence
<220> FEATURE:
<223> OTHER INFORMATION: nucleotide sequence of engineered target
      sequence recognized by microRNA Ghi_miRcan1230(2) and (3)

<400> SEQUENCE: 23
agttttaaag tagtgtcatg caaagccagc aatg                                34

<210> SEQ ID NO 24
<211> LENGTH: 12756
<212> TYPE: DNA
<213> ORGANISM: Artificial
<220> FEATURE:
<223> OTHER INFORMATION: T-DNA of pTEA9

<400> SEQUENCE: 24

```
aattacaacg gtatatatcc tgccagtact gggcccccte gagggcgatc gcgcggccgc      60
ttcacggaaa gttgttatat ataagttcag taaataataa tgaaatataa atttaatta     120 tatctagtac tcaataagaa gatggagaaa gttatgttaa ttatagttat aaattattta    180
taaatttaat atatatatat aaagaaaata gttgtataac taataattat ttttacaata    240
ctttatatag ttatatttaa aaaaatttta aaattaaaat actattattt tgttcaatat    300
attaatattt atattattta atttattatt gaatatgaat aaattttttt tgaaaattat    360 attttaatt tttagaaatt ttatataact ttccatatat atatttctga tttgtcaatt     420
tcttttgaga tttatctaaa ttgatttgaa ttttttttat ttttaaaaaa taaaataatt    480
ttaaaatttc ttggaatttt atataaattt ttggatttt caaaaaaat tgagatttt       540 ttcttttttt tcgattttt aaatttattt caggaaaata taaactaact tttctttgct     600
ttgggtataa ttaatattag ataacccaca aattagatca ataggagctt catgtcctaa    660
tcccatttaa ttacttttgt tgtatcatta atttagtcga ccttacatag tagctctatg    720
gggcaaatag ttataaatgt taaattagta tttaaatctt gaagttttta atttaaagtt    780
cagactatta gtattatatc aaatatttaa gggtaaatat atattctaat atctaagctt    840
gggtcaaggt ttaaattaag tacttaaact tggttttata gttcaaattg atttaaataa    900
ctaagtatta atttgaatta agaagcaaag ttcaagtacc taattagact ataaaaaaaa    960
cttttgctag taaattgaac cttaaagtcg agtttagtta tctaattgga caaaaaatc    1020 ttaaatacca atttaaaccc taaagtcaag tttaggtacc aaagtgtata tttatctaat   1080
atttaaattt gatccaccta atttaaattt ttttggtcca atgcaataag gaattaatt   1140 aatacttaca cacatgatag agatataccc acaacagata cacactacaa aaaacattaa  1200
aaaatagaaa gatatatttc ctacaaaatt taaaagcatt taattttta actaacatta   1260 gacaaatgga aatggaaaga cttatttta agttatgga tgaatctaat ttatctaaac    1320
attgggtttt ttttttttgt gacgaaatat gggtgagaga aggtagtaag ctaagtaggg  1380
gagtaatatc tcaaacaaat aattaaaaaa ctccttaaa tgtggctata aatacctgaa    1440
accaatcctt ctttcctcaa ctcaaatctt caatctttag atcatctctc caaaaaata   1500
```

```
ccatgagtaa acggaatccg aagattctga agattttctct gtatatgtta cttctcaact   1560
ctctctttct catcatctac ttcgttttttc actcatcgtc gttttcagag tccagaatca   1620
gcaaccggtt atcgagttcc gccacaagga cggtacgagc cttcagaaat cgatgtcatg   1680
ccaggccagg gacaccggga tcgagttacg gaaatgcgag gcgaccgctt ccctcggcac   1740
cagcgccttt acactacaat agcccaagtc gcgcagcgag tcattatcca cggtaccatg   1800
gaggttatgc ggacgacgtg acagttagca tgggaccgga cgacgatcgt acagatatct   1860
ttggccccga aaccgatctc agcgaaacgc gccacctcaa cgacgcatac gggtttcggt   1920
catcccagat caccctcagc gaagatcccc acggcaccca cgcgcgttcc cggtacgacg   1980
acgaagacga tgtgagcacc acttattcct ccaacacggg caccagcgct tcaggtgtcg   2040
acaagttcga gcattacggt cccattccgg aggaaggcaa gcacgagcgg cgcggcgtgc   2100
gaccaccaca gatgtcgagg aaggaagtcc agctcatcaa cggcgaactc gttctcgagt   2160
gcaagattcc gactatattg tattcgtttt tgcccaggag agacgaagtg gagtttacgc   2220
acatgcggta cacagccgtc acttgtgacc ctgatgactt tgttgccagg ggttacaagt   2280
tgcgccagaa tatcggtcgt accgccaggg agacggagct gttcatctgc gtgaccatgt   2340
acaacgagga cgagttcgga ttcacacgga ctatgcacgc agtgatgaag aacatttcgc   2400
attttttgttc ccgaaacaag agtaggacgt ggggagcgga tgggtggcag aagattgtgg   2460
tctgtgtggt ttcggatgga cgagagatca ttcaccccg gaccttggac gccctcgcag   2520
ccatgggcgt ttaccagcac ggtatcgcca agaactttgt caaccagaag gcggtgcagg   2580
cccacgttta cgagtacacg acacaagtgt ctctggacag cgacctcaag ttcaagggcg   2640
ccgagaaggg catcgtgccc tgccagatga ttttttgctt gaaggagaag aaccaaaaga   2700
aactcaactc gcatagatgg ttcttcaacg ccttttggcaa agccttgaac ccgaatgtgt   2760
gtatcctcct agacgtcggc acccgccccg gcggcacaag tctctaccat ctctggaaag   2820
ccttcgacac ggattccaac gtggcggggg cctgcgggga aatcaaagcg atgaaggggc   2880
ggtttggcgg gaatttgctc aaccctctgg tggctagtca gaactttgag tacaagatga   2940
gcaatattct ggacaaaccg ttggagtcgg tgtttgggta catcacggtg ttgccgggcg   3000
ccttgtcggc gtatcggtac catgcgctgc agaacgatga cacgggccat gggccgttga   3060
gtcagtattt caagggcgag acgctccatg gcagcacgc ggatgtgttt acggcgaaca   3120
tgtacttggc cgaggaccga attctgtgtt gggagttggt ggccaagagg ggtgagaggt   3180
gggtgttgaa gtatgtgaag gggtgtacgg gtgagacgga tgtgcctgac accgtcccgg   3240
aattcgtctc gcaacgtcgt cgttggctca acggtgcctt cttcgccgcc gtctactccc   3300
tcgtccactt tcgacaaatc tggaaaaccg accacacctt tatgcgcaaa gcccttctcc   3360
acgtcgaatt cctctaccac ctcctgcaac tcctcttcac ctacttctcc ctggccaact   3420
tctacctcgc cttctacttt atcgccggcg gactcgccga tccccacgtc gaccctttta   3480
actcggacgg ccacgtcgcg cgcatcatct tcaacatcct ccgctacgtc tgcgtcctgc   3540
tgatctgcac acaattcatc ttgtccctcg gcaaccgtcc gcagggtgcc aaaagaatgt   3600
atctcgcatc catgatcatc tacgccgtca tcatggtgta caccaccttc gccaccatct   3660
tcatcgtcgt gcgacaaatc caaccctctc aaaaatccga cgacaagccc gacctcgaac   3720
tcggcaacaa cgtcttcacc aacctgatcg tctccgtggc tagtaccctc gggctctact   3780
tcgtcatgtc ctttctctat ctcgaccct ggcacatgtt cacctcggcc atccagtact   3840
ttgtcctgct gccttcctac atctgcacgc tccagatcta cgccttttgc aacacccacg   3900
```

```
acgtcacatg gggcaccaaa ggcgacaacg tgatgcgcac cgatctcgga ggcgccattg   3960
gcaagggaag caccgtcgaa ctggaaatgc cttcggacca actcgacatc gactcgggat   4020
acgacgaatg tctacgaaat ctccgggatc gcgtcatggt ccctgccgtt cccgtgtccg   4080
aggaccagct gcagcaggat tactacaagt cggtgcgcac gtacatggtg gtgtcgtgga   4140
tggtggccaa cgcgacgctg gccatggcgg tgtcggaagc gtatggcgat tcggaaattg   4200
gggataattt ttacttgcgg tttatcctgt gggcggtggc ggccctggcg ctgtttagag   4260
cgttggggtc gacgacgttt gcggcgatta atctggtgag tgctctcgtg gagggcaggg   4320
tcaggctgag gttgaatatg aaagggttta ggtggattaa ggagaagtgg ggggatgcgg   4380
atgtgaaggg caagtttgag gggttggggg atcgggcgag ggggttggcg aggcggtgag   4440
agctcgccat tgggcgacct gggaacacta gagctagcaa gcttggacac gctgaaatca   4500
ccagtctctc tctacaaatc tatctctctc tattttctcc ataataatgt gtgagtagtt   4560
cccagataag ggaattaggg ttcctatagg gtttcgctca tgtgttgagc atataagaaa   4620
cccttagtat gtatttgtat ttgtaaaata cttctatcaa taaaatttct aattcctaaa   4680
accaaaatcc agtactaaaa tccagatcat gcatggtaca gcacgcgtcc tgcaggcccg   4740
ggttaattaa gcggccgctt cacggaaagt tgttatatat aagttcagta aataataatg   4800
aaatataaat tttaattata tctagtactc aataagaaga tggagaaagt tatgttaatt   4860
atagttataa attatttata aatttaatat atatatataa agaaaatagt tgtataacta   4920
ataattattc ttacaatact ttatatagtt atatttaaaa aaattttaaa attaaaatac   4980
tattattttg ttcaatatat taatatttat attatttaat ttattattga atatgaataa   5040
atttttttg aaaattatat ttttaatttt tagaaatttt atataacttt ccatatatat   5100
atttctgatt tgtcaatttc ttttgagatt tatctaaatt gatttgaatt ttttttattt   5160
ttaaaaaata aaataatttt aaaatttctt ggaatttat ataaattttt ggatttttca   5220
aaaaaaattg agatttttt cttttttttc gattttttaa atttatttca ggaaaatata   5280
aactaacttt tctttgcttt gggtataatt aatattagat aacccacaaa ttagatcaat   5340
aggagcttca tgtcctaatc ccatttaatt acttttgttg tatcattaat ttagtcgacc   5400
ttacatagta gctctatggg gcaaatagtt ataaatgtta aattagtatt taaatcttga   5460
agttttaat ttaaagttca gactattagt attatatcaa atatttaagg gtaaatatat   5520
attctaatat ctaagcttgg gtcaaggttt aaattaagta cttaaacttg gttttatagt   5580
tcaaattgat ttaaataact aagtattaat ttgaattaag aagcaaagtt caagtaccta   5640
attagactat aaaaaaaact tttgctagta aattgaacct taaagtcgag tttagttatc   5700
taattggaca aaaaaatctt aaataccaat ttaaaccta agtcaagtt taggtaccaa   5760
agtgtatatt tatctaatat ttaaatttga tccacctaat ttaaattttt ttggtccaat   5820
gcaataagag aattaattaa tacttacaca catgatagag atatacccac aacagataca   5880
cactacaaaa aacattaaaa aatagaaaga tatatttcct acaaaattta aaagcattta   5940
attttttaac taacattaga caaatggaaa tggaaagact tatttttaag tttatggatg   6000
aatctaattt atctaaacat tgggtttttt tttttgtga cgaaatatgg gtgagagaag   6060
gtagtaagct aagtagggga gtaatatctc aaacaaataa ttaaaaaact cctttaaatg   6120
tggctataaa tacctgaaac caatccttct ttcctcaact caaatcttca atctttagat   6180
catctctcca aaaaaatacc atgtgcggaa ttgttggtgc tatcgcccaa agagacgttg   6240
```

```
ctgagattttt gttagagggt ctgcgaaggc tagagtatag aggatatgac tccgctggtc    6300
tggctgtcgt tgatgctgag ggtcatatga caaggctaag aaggttagga aaggttcaga    6360
tgcttgctca ggcagctgag gaacatccat tgcatggagg tactggtatt gcacatacca    6420
ggtgggctac tcatggggag ccatcagaag ttaatgctca tccacatgtg agtgagcata    6480
tcgttgtagt tcacaatggg ataattgaaa accacgaacc attgagggaa gagttaaagg    6540
caagaggata tacttttgtg agtgagactg acactgaggt tattgcacat ttagtgaact    6600
gggaactcaa acagggggc acattgcgtg aggctgtgtt aagagctatt cctcaactta    6660
gaggtgcata cggtactgtt attatggatt caagacaccc agatactctc cttgcagcta    6720
gatcaggtag tcccttggtc ataggacttg gaatgggtga aaattttatc gctagcgacc    6780
aattggcctt attgccagtt acaagacgat ttattttcct tgaagagggc gatattgctg    6840
agattactag aaggtctgtg aacatctttg ataagactgg cgctgaggtt aaacgtcagg    6900
atatcgagtc taaccttcaa tacgatgctg gtgataaagg aatttacagg cattatatgc    6960
aaaaggaaat ttatgaacaa ccaaatgcta tcaaaaacac acttactggc cgtatttctc    7020
atggacaggt cgatttaagc gagcttggtc ctaatgcaga cgaactgcta tcaaaagttg    7080
agcacataca gatactggca tgcggaacta gttataattc aggaatggtg tctagatact    7140
ggttcgaaag cttggcaggt ataccttgtg atgtagagat cgcttctgag tttaggtata    7200
gaaagtctgc tgtgcgtaga aattcattaa tgattacatt atctcaatcc ggagaaacag    7260
cagatacact ggctggattg aggctttcta aggaactcgg atatctgggt tcacttgcta    7320
tttgtaatgt accaggttcc tcattggttc gtgaatcaga tctagcactt atgacaaatg    7380
caggaactga ataggtgtg gcaagtacca aggctttcac aacccaactg accgtacttt    7440
taatgttggt agcaaaactc agtcgattaa aggggctaga tgcatctatc gaacatgata    7500
ttgttcacgg gcttcaagct ctcccttcaa gaattgaaca aatgctttca caagataaga    7560
gaatagaggc attggctgaa gattttccg acaaacatca cgcattgttt cttggacgtg    7620
gcgatcaata tccaattgca ttggaaggag ctttgaagtt gaaagaaata agttacattc    7680
acgcagaagc atatgcagct ggagaactca agcatggtcc tttggcactc atcgacgctg    7740
acatgcccgt gatcgtagtg gctcctaata cgaactgct cgaaaagctt aaatcaaata    7800
tcgaagaggt tcgagctaga ggaggtcagc tttacgtttt cgctgaacaa gatgctggat    7860
tcgtgtcaag cgataatatg catataattg aaatgcctca cgttgaagaa gtgattgcac    7920 ctatattta tacagtccca ttgcaacttc tagcttacca tgttcactt attaaaggaa    7980 ctgatgttga tcagcctaga aacctagcaa aatctgtaac agtcgaataa acgcgtaggc    8040
ctgccattgg gcgacctggg aacactagag gcgcgccccc gatccgcgtt tgtgtttct    8100 gggtttctca cttaagcgtc tgcgttttac ttttgtattg ggtttggcgt ttagtagttt    8160
gcggtagcgt tcttgttatg tgtaattacg cttttcttc ttgcttcagc agtttcggtt    8220
gaaatataaa tcgaatcaag tttcactta tcagcgttgt tttaaatttt ggcattaaat    8280
tggtgaaaat tgcttcaatt ttgtatctaa atagaagaga caacatgaaa ttcgactttt    8340
gacctcaaat cttcgaacat ttatttcctg atttcacgat ggatgaggat aacgaaaggg    8400
cggttcctat gtccgggaaa gttcccgtag aagacaatga gcaaagctac tgaaacgcgg    8460
acacgacgtc gcattggtac ggatatgagt taaaccgact caattccttt attaagacat    8520
aaaccgattt tggttaaagt gtaacagtga gctgatataa aaccgaaaca aaccggtaca    8580
agtttgattg agcaacttga tgacaaactt cagaattttg gttattgaat gaaaatcata    8640
```

```
gtctaatcgt aaaaaatgta cagaagaaaa gctagagcag aacaaagatt ctatattctg    8700
gttccaattt atcatcgctt taacgtccct cagatttgat cggggaattc gatatcatta    8760
ccctgttatc cctaaagctt attaatgttt gtcgaggaga aatatgagtc gaggcatgga    8820
tacactaagt tccectgaag tgagcatgat ctttgatgct gagatgattc ccagagcaag    8880
atagtttgtg ctgcaagtga cacaattgta atgaaaccac cactcaacga atttacttgt    8940
ggctttgaca tgtcgtgtgc tctgtttgta tttgtgagtg ccggttggta attatttttg    9000
ttaatgtgat tttaaaacct cttatgtaaa tagttacttt atctattgaa gtgtgttctt    9060
gtggtctata gtttctcaaa gggaaattaa aatgttgaca tcccatttac aattgataac    9120
ttggtataca caaactttgt aaatttggtg atatttatgg tcgaaagaag gcaatacccca   9180
ttgtatgttc caatatcaat atcaatacga taacttgata atactaacat atgattgtca    9240
ttgttttttcc agtatcaata tacattaagc tactacaaaa ttagtataaa tcactatatt   9300
ataaatcttt ttcggttgta acttgtaatt cgtgggtttt taaaataaaa gcatgtgaaa    9360
attttcaaat aatgtgatgg cgcaattttta ttttccgagt tccaaaatat tgccgcttca   9420
ttaccctaat ttgtggcgcc acatgtaaaa caaaagacga ttcttagtgg ctatcactgc    9480
catcacgcgg atcactaata tgaaccgtcg attaaaacag atcgacggtt tatacatcat    9540
tttattgtac acacggatcg atatctcagc cgttagattt aatatgcgat ctgattgctc    9600
aaaaaataga ctctccgtct ttgcctataa aaacaatttc acatctttct cacccaaatc    9660
tactcttaac cgttcttctt cttctacaga catcaatttc tctcgactct agaggatcca    9720
agcttatcga tttcgaaccc ctcaggcgaa gaacaggtat gatttgtttg taattagatc    9780
aggggtttag gtcttttccat tacttttttaa tgtttttttct gttactgtct ccgcgatctg    9840
atttttacgac aatagagttt cgggttttgt cccattccag tttgaaaata aggtccgtc    9900
ttttaagttt gctggatcga taaacctgtg aagattgagt ctagtcgatt tattggatga    9960
tccattcttc atcgtttttt tcttgcttcg aagttctgta taaccagatt tgtctgtgtg   10020
cgattgtcat tacctagccg tgtatcgaga actagggttt tcgagtcaat tttgccccctt   10080
ttggttatat ctggttcgat aacgattcat ctggattagg gttttaagtg gtgacgttta   10140
gtattccaat ttcttcaaaa tttagttatg gataatgaaa atccccaatt gactgttcaa   10200
tttcttgtta aatgcgcaga tcacaatggc ttcgatctcc tcctcagtcg cgaccgttag    10260
ccggaccgcc cctgctcagg ccaacatggt ggctccgttc accggcctta agtccaacgc   10320
cgccttcccc accaccaaga aggctaacga cttctccacc cttcccagca acggtggaag   10380
agttcaatgt atgcaggtgt ggccggccta cggcaacaag aagttcgaga cgctgtcgta   10440
cctgccgccg ctgtctatgg cgccaccgt gatgatggcc tcgtcggcca ccgccgtcgc   10500
tccgttccag gggctcaagt ccaccgccag cctccccgtc gcccgccgct cctccagaag   10560
cctcggcaac gtcagcaacg gcggaaggat ccggtgcatg gccggcgccg aggagatcgt   10620
gctgcagccc atcaaggaga tctccggcac cgtcaagctg ccggggtcca agtcgctttc   10680
caaccggatc ctcctactcg ccgccctgtc cgaggggaca acagtggttg ataacctgct   10740
gaacagtgag gatgtccact acatgctcgg ggccttgagg actcttggtc tctctgtcga   10800
agcggacaaa gctgccaaaa gagctgtagt tgttggctgt ggtggaaagt tcccagttga   10860
ggatgctaaa gaggaagtgc agctcttctt ggggaatgct ggaatcgcaa tgcggtcctt   10920
gacagcagct gttactgctg ctggtggaaa tgcaacttac gtgcttgatg gagtaccaag   10980
```

```
aatgagggag agacccattg gcgacttggt tgtcggattg aagcagcttg gtgcagatgt   11040
tgattgtttc cttggcactg actgcccacc tgttcgtgtc aatggaatcg gagggctacc   11100
tggtggcaag gtcaagctgt ctggctccat cagcagtcag tacttgagtg ccttgctgat   11160
ggctgctcct ttggctcttg gggatgtgga gattgaaatc attgataaat taatctccat   11220
tccgtacgtc gaaatgacat tgagattgat ggagcgtttt ggtgtgaaag cagagcattc   11280
tgatagctgg gacagattct acattaaggg aggtcaaaaa tacaagtccc ctaaaaatgc   11340
ctatgttgaa ggtgatgcct caagcgcaag ctatttcttg gctggtgctg caattactgg   11400
agggactgtg actgtggaag gttgtggcac caccagtttg cagggtgatg tgaagtttgc   11460
tgaggtactg gagatgatgg gagcgaaggt tacatggacc gagactagcg taactgttac   11520
tggcccaccg cgggagccat ttgggaggaa cacctcaag gcgattgatg tcaacatgaa    11580
caagatgcct gatgtcgcca tgactcttgc tgtggttgcc ctctttgccg atggcccgac   11640
agccatcaga gacgtggctt cctggagagt aaaggagacc gagaggatgg ttgcgatccg   11700
gacggagcta accaagctgg gagcatctgt tgaggaaggg ccggactact gcatcatcac   11760
gccgccggag aagctgaacg tgacggcgat cgacacgtac gacgaccaca ggatggcgat   11820
ggctttctcc cttgccgcct gtgccgaggt ccccgtcacc atccgggacc tgggtgcac    11880 ccggaagacc ttccccgact acttcgatgt gctgagcact ttcgtcaaga attaagctct   11940
agaactagtg atcccccga tccgcgtttg tgttttctgg gtttctcact taagcgtctg    12000
cgttttactt ttgtattggg tttggcgttt agtagtttgc ggtagcgttc ttgttatgtg   12060
taattacgct ttttcttctt gcttcagcag tttcggttga aatataaatc gaatcaagtt   12120
tcactttatc agcgttgttt taaattttgg cattaaattg gtgaaaattg cttcaatttt   12180
gtatctaaat agaagagaca acatgaaatt cgacttttga cctcaaatct tcgaacattt   12240
atttcctgat ttcacgatgg atgaggataa cgaaagggcg gttcctatgt ccgggaaagt   12300
tcccgtagaa gacaatgagc aaagctactg aaacgcggac acgacgtcgc attggtacgg   12360
atatgagtta aaccgactca attcctttat taagacataa accgattttg gttaaagtgt   12420
aacagtgagc tgatataaaa ccgaaacaaa ccggtacaag tttgattgag caacttgatg   12480
acaaacttca gaattttggt tattgaatga aaatcatagt ctaatcgtaa aaaatgtaca   12540
gaagaaaagc tagagcagaa caaagattct atattctggt tccaatttat catcgcttta   12600
acgtccctca gatttgatcg ggaaaccaaa acgtcgtgag acagtttggt taactataac   12660
ggtcctaagg tagcgatcga ggcattacgg cattacggca ctcgcgaggg tccgaattcg   12720
agcatggagc catttacaat tgaatatatc ctgccg                             12756
```

<210> SEQ ID NO 25
<211> LENGTH: 13770
<212> TYPE: DNA
<213> ORGANISM: Artificial
<220> FEATURE:
<223> OTHER INFORMATION: T-DNA of pTEA10

<400> SEQUENCE: 25

```
aattacaacg gtatatatcc tgccagtact gggcccctc gagggcgatc gcgcggccgc      60
ttcacggaaa gttgttatat ataagttcag taaataataa tgaaatataa attttaatta   120
tatctagtac tcaataagaa gatggagaaa gttatgttaa ttatagttat aaattattta   180
taaatttaat atatatatat aaagaaaata gttgtataac taataattat ttttacaata   240
ctttatatag ttatatttaa aaaaatttta aaattaaaat actattattt tgttcaatat   300
```

```
attaatattt atattattta atttattatt gaatatgaat aaattttttt tgaaaattat      360
atttttaatt tttagaaatt ttatataact ttccatatat atatttctga tttgtcaatt      420
tcttttgaga tttatctaaa ttgatttgaa tttttttat ttttaaaaaa taaaataatt       480
ttaaaatttc ttggaattt atataaattt ttggattttt caaaaaaaat tgagattttt       540
ttcttttttt tcgattttt aaatttattt caggaaaata taaactaact tttctttgct       600
ttgggtataa ttaatattag ataacccaca aattagatca ataggagctt catgtcctaa      660
tcccatttaa ttacttttgt tgtatcatta atttagtcga ccttacatag tagctctatg      720
gggcaaatag ttataaatgt taaattagta tttaaatctt gaagttttta atttaaagtt      780
cagactatta gtattatatc aaatatttaa gggtaaatat atattctaat atctaagctt      840
gggtcaaggt ttaaattaag tacttaaact tggttttata gttcaaattg atttaaataa      900
ctaagtatta atttgaatta agaagcaaag ttcaagtacc taattagact ataaaaaaaa      960
cttttgctag taaattgaac cttaaagtcg agtttagtta tctaattgga caaaaaaatc     1020
ttaaatacca atttaaaccc taaagtcaag tttaggtacc aaagtgtata tttatctaat     1080
atttaaattt gatccaccta atttaaattt ttttggtcca atgcaataag agaattaatt     1140
aatacttaca cacatgatag agatatacc acaacagata cacactacaa aaaacattaa      1200
aaaatagaaa gatatatttc ctacaaaatt taaaagcatt taattttta actaacatta     1260 gacaaatgga aatggaaaga cttattttta agtttatgga tgaatctaat ttatctaaac     1320
attgggtttt tttttttgt gacgaaatat gggtgagaga aggtagtaag ctaagtaggg     1380
gagtaatatc tcaaacaaat aattaaaaaa ctcctttaaa tgtggctata aatacctgaa     1440
accaatcctt ctttcctcaa ctcaaatctt caatctttag atcatctctc caaaaaata     1500 ccatgagtaa acggaatccg aagattctga agatttttct gtatatgtta cttctcaact     1560
ctctctttct catcatctac ttcgtttttc actcatcgtc gttttcagag tccagaatca     1620
gcaaccggtt atcgagttcc gccacaagga cggtacgagc cttcagaaat cgatgtcatg     1680
ccaggccagg gacaccggga tcgagttacg gaaatgcgag gcgaccgctt ccctcggcac     1740
cagcgccttt acactacaat agcccaagtc gcgcagcgag tcattatcca cggtaccatg     1800
gaggttatgc ggacgacgtg acagttagca tgggaccgga cgacgatcgt acagatatct     1860
ttggccccga aaccgatctc agcgaaacgc gccacctcaa cgacgcatac gggtttcggt     1920
catcccagat caccctcagc gaagatcccc acggcaccca cgcgcgttcc cggtacgacg     1980
acgaagacga tgtgagcacc acttattcct ccaacacggg caccagcgct tcaggtgtcg     2040
acaagttcga gcattacggt cccattccgg aggaaggcaa gcacgagcgg cgcggcgtgc     2100
gaccaccaca gatgtcgagg aaggaagtcc agctcatcaa cggcgaactc gttctcgagt     2160
gcaagattcc gactatattg tattcgtttt tgcccaggag agacgaagtg gagtttacgc     2220
acatgcggta cacagccgtc acttgtgacc ctgatgactt tgttgccagg ggttacaagt     2280
tgcgccagaa tatcggtcgt accgccaggg agacggagct gttcatctgc gtgaccatgt     2340
acaacgagga cgagttcgga ttcacacgga ctatgcacgc agtgatgaag aacatttcgc     2400 attttttgttc ccgaaacaag agtaggacgt ggggagcgga tgggtggcag aagattgtgg    2460
tctgtgtggt ttcggatgga cgagagatca ttcaccccg gaccttggac gccctcgcag      2520
ccatgggcgt ttaccagcac ggtatcgcca agaactttgt caaccagaag gcggtgcagg     2580
cccacgttta cgagtacacg acacaagtgt ctctggacag cgacctcaag ttcaagggcg     2640
```

```
ccgagaaggg catcgtgccc tgccagatga ttttttgctt gaaggagaag aaccaaaaga    2700
aactcaactc gcatagatgg ttcttcaacg cctttggcaa agccttgaac ccgaatgtgt    2760
gtatcctcct agacgtcggc acccgccccg gcggcacaag tctctaccat ctctggaaag    2820
ccttcgacac ggattccaac gtggcggggg cctgcgggga aatcaaagcg atgaaggggc    2880
ggtttggcgg gaatttgctc aaccctctgg tggctagtca gaactttgag tacaagatga    2940
gcaatattct ggacaaaccg ttggagtcgg tgtttgggta catcacggtg ttgccgggcg    3000
ccttgtcggc gtatcggtac catgcgctgc agaacgatga gacgggccat gggccgttga    3060
gtcagtattt caagggcgag acgctccatg ggcagcacgc ggatgtgttt acggcgaaca    3120
tgtacttggc cgaggaccga attctgtgtt gggagttggt ggccaagagg ggtgagaggt    3180
gggtgttgaa gtatgtgaag gggtgtacgg gtgagacgga tgtgcctgac accgtcccgg    3240
aattcgtctc gcaacgtcgt cgttggctca acggtgcctt cttcgccgcc gtctactccc    3300
tcgtccactt tcgacaaatc tggaaaaccg accacccttt atgcgcaaa gcccttctcc     3360
acgtcgaatt cctctaccac ctcctgcaac tcctcttcac ctacttctcc ctggccaact    3420
tctacctcgc cttctacttt atcgccggcg gactcgccga tccccacgtc gaccctttta   3480
actcggacgg ccacgtcgcg cgcatcatct tcaacatcct ccgctacgtc tgcgtcctgc    3540
tgatctgcac acaattcatc ttgtccctcg gcaaccgtcc gcagggtgcc aaaagaatgt    3600
atctcgcatc catgatcatc tacgccgtca tcatggtgta caccaccttc gccaccatct    3660
tcatcgtcgt gcgacaaatc caaccctctc aaaaatccga cgacaagccc gacctcgaac    3720
tcggcaacaa cgtcttcacc aacctgatcg tctccgtggc tagtaccctc gggctctact    3780
tcgtcatgtc ctttctctat ctcgacccct ggcacatgtt cacctcggcc atccagtact    3840
ttgtcctgct gccttcctac atctgcacgc tccagatcta cgccttttgc aacacccacg    3900
acgtcacatg gggcaccaaa ggcgacaacg tgatgcgcac cgatctcgga ggcgccattg    3960
gcaagggaag caccgtcgaa ctggaaatgc cttcggacca actcgacatc gactcgggat    4020
acgacgaatg tctacgaaat ctccgggatc gcgtcatggt ccctgccgtt cccgtgtccg    4080
aggaccagct gcagcaggat tactacaagt cggtgcgcac gtacatggtg gtgtcgtgga    4140
tggtggccaa cgcgacgctg gccatggcgg tgtcggaagc gtatggcgat tcggaaattg    4200
gggataattt ttacttgcgg tttatcctgt gggcggtggc ggccctggcg ctgtttagag    4260
cgttggggtc gacgacgttt gcggcgatta atctggtgag tgctctcgtg gagggcaggg    4320
tcaggctgag gttgaatatg aaagggttta ggtggattaa ggagaagtgg ggggatgcgg    4380
atgtgaaggg caagtttgag gggttggggg atcgggcgag ggggttggcg aggcggtgag    4440
agctcagttt taaagtagtg tcatgcaaag ccagcaatgg ctagcaagct tggacacgct    4500
gaaatcacca gtctctctct acaaatctat ctctctctat tttctccata ataatgtgtg    4560
agtagttccc agataaggga attagggttc ctatagggtt tcgctcatgt gttgagcata    4620
taagaaaccc ttagtatgta tttgtatttg taaaatactt ctatcaataa aatttctaat    4680
tcctaaaacc aaaatccagt actaaaatcc agatcatgca tggtacagca cgcgtcctgc    4740
aggcccgggt taattaagcg gccgcttcac ggaaagttgt tatatataag ttcagtaaat    4800
aataatgaaa tataaatttt aattatatct agtactcaat aagaagatgg agaaagttat    4860
gttaattata gttataaatt atttataaat ttaatatata tataaaga aaatagttgt      4920
ataactaata attattttta caatacttta tatagttata tttaaaaaaa ttttaaaatt    4980
aaaatactat tattttgttc aatatattaa tatttatatt atttaattta ttattgaata    5040
```

```
tgaataaatt ttttttgaaa attatatttt taatttttag aaattttata taacttcca      5100
tatatatatt tctgatttgt caatttcttt tgagatttat ctaaattgat ttgaatttt      5160
tttatttta  aaaaataaaa taattttaaa atttcttgga attttatata aattttgga      5220
tttttcaaaa aaaattgaga ttttttcctt tttttcgat tttaaatt tatttcagga       5280
aaatataaac taacttttct ttgctttggg tataattaat attagataac ccacaaatta    5340
gatcaatagg agcttcatgt cctaatccca tttaattact tttgttgtat cattaattta    5400
gtcgacctta catagtagct ctatgggca aatagttata aatgttaaat tagtatttaa     5460
atcttgaagt tttaaattta aagttcagac tattagtatt atatcaaata tttaagggta    5520
aatatatatt ctaatatcta agcttgggtc aaggtttaaa ttaagtactt aaacttggtt    5580
ttatagttca aattgattta aataactaag tattaatttg aattaagaag caaagttcaa    5640
gtacctaatt agactataaa aaaactttt gctagtaaat tgaaccttaa agtcgagttt     5700
agttatctaa ttggacaaaa aaatcttaaa taccaattta aaccctaaag tcaagtttag    5760
gtaccaaagt gtatatttat ctaatattta aatttgatcc acctaattta aatttttttg    5820
gtccaatgca ataagagaat taattaatac ttacacacat gatagagata tacccacaac    5880
agatacacac tacaaaaaac attaaaaaat agaaagatat atttcctaca aaatttaaaa    5940
gcatttaatt ttttaactaa cattagacaa atggaaatgg aaagacttat ttttaagttt    6000
atggatgaat ctaatttatc taaacattgg gttttttttt tttgtgacga aatatgggtg    6060
agagaaggta gtaagctaag taggggagta atatctcaaa caataatta aaaaactcct    6120
ttaaatgtgg ctataaatac ctgaaaccaa tccttctttc ctcaactcaa atcttcaatc    6180
tttagatcat ctctccaaaa aaataccatg tgcggaattg ttggtgctat cgcccaaaga    6240
gacgttgctg agattttgtt agagggtctg cgaaggctag agtatagagg atatgactcc    6300
gctggtctgg ctgtcgttga tgctgagggt catatgacaa ggctaagaag gttaggaaag    6360
gttcagatgc ttgctcaggc agctgaggaa catccattgc atggaggtac tggtattgca    6420
cataccaggt gggctactca tggggagcca tcagaagtta atgctcatcc acatgtgagt    6480
gagcatatcg ttgtagttca caatgggata attgaaaacc acgaaccatt gagggaagag    6540
ttaaaggcaa gaggatatac ttttgtgagt gagactgaca ctgaggttat tgcacattta    6600
gtgaactggg aactcaaaca gggggcaca ttgcgtgagg ctgtgttaag agctattcct    6660
caacttagag gtgcatacgg tactgttatt atggattcaa gacacccaga tactctcctt    6720
gcagctagat caggtagtcc cttggtcata ggacttggaa tgggtgaaaa ttttatcgct    6780
agcgaccaat tggccttatt gccagttaca agacgattta ttttccttga agagggcgat    6840
attgctgaga ttactagaag gtctgtgaac atctttgata agactggcgc tgaggttaaa    6900
cgtcaggata tcgagtctaa ccttcaatac gatgctggtg ataaaggaat ttacaggcat    6960
tatatgcaaa aggaaattta tgaacaacca aatgctatca aaaacacact tactggccgt    7020
atttctcatg gacaggtcga tttaagcgag cttggtccta atgcagacga actgctatca    7080
aaagttgagc acatacagat actggcatgc ggaactagtt ataattcagg aatggtgtct    7140
agatactggt tcgaaagctt ggcaggtata ccttgtgatg tagagatcgc ttctgagttt    7200
aggtatagaa agtctgctgt gcgtagaaat tcattaatga ttacattatc tcaatccgga    7260
gaaacagcag atacactggc tggattgagg ctttctaagg aactcggata tctgggttca    7320
cttgctattt gtaatgtacc aggttcctca ttggttcgtg aatcagatct agcacttatg    7380
```

```
acaaatgcag gaactgaaat aggtgtggca agtaccaagg ctttcacaac ccaactgacc    7440
gtactttnaa tgttggtagc aaaactcagt cgattaaagg ggctagatgc atctatcgaa    7500
catgatattg ttcacgggct tcaagctctc ccttcaagaa ttgaacaaat gctttcacaa    7560
gataagagaa tagaggcatt ggctgaagat ttttccgaca acatcacgc attgtttctt     7620 ggacgtggcg atcaatatcc aattgcattg gaaggagctt tgaagttgaa agaaataagt    7680
tacattcacg cagaagcata tgcagctgga gaactcaagc atggtccttt ggcactcatc    7740
gacgctgaca tgcccgtgat cgtagtggct cctaataacg aactgctcga aaagcttaaa    7800
tcaaatatcg aagaggttcg agctagagga ggtcagcttt acgttttcgc tgaacaagat    7860
gctggattcg tgtcaagcga taatatgcat ataattgaaa tgcctcacgt tgaagaagtg    7920
attgcaccta tattttatac agtcccattg caacttctag cttaccatgt tgcacttatt    7980
aaaggaactg atgttgatca gcctagaaac ctagcaaaat ctgtaacagt cgaataaacg    8040
cgtaggccta gttttaaagt agtgtcatgc aaagccagca atgggcgcgc ccccgatccg    8100
cgtttgtgtt ttctgggttt ctcacttaag cgtctgcgtt ttactttttgt attgggtttg    8160 gcgtttagta gtttgcggta gcgttcttgt tatgtgtaat tacgcttttt cttcttgctt    8220
cagcagtttc ggttgaaata taaatcgaat caagtttcac tttatcagcg ttgttttaaa    8280
ttttggcatt aaattggtga aaattgcttc aattttgtat ctaaatagaa gagacaacat    8340
gaaattcgac ttttgacctc aaatcttcga acatttattt cctgatttca cgatggatga    8400
ggataacgaa agggcggttc ctatgtccgg gaaagttccc gtagaagaca atgagcaaag    8460
ctactgaaac gcggacacga cgtcgcattg gtacggatat gagttaaacc gactcaattc    8520
ctttattaag acataaaccg attttggtta aagtgtaaca gtgagctgat ataaaaccga    8580
aacaaaccgg tacaagtttg attgagcaac ttgatgacaa acttcagaat tttggttatt    8640
gaatgaaaat catagtctaa tcgtaaaaaa tgtacagaag aaaagctaga gcagaacaaa    8700
gattctatat tctggttcca atttatcatc gctttaacgt ccctcagatt tgatcgggga    8760
attcgatatc attaccctgt tatccctaaa gcttattaat gtttgtcgag gagaaatatg    8820
agtcgaggca tggatacact aagttcccct gaagtgagca tgatctttga tgctgagatg    8880
attcccagag caagatagtt tgtgctgcaa gtgacacaat tgtaatgaaa ccaccactca    8940
acgaatttac ttgtggcttt gacatgtcgt gtgctctgtt tgtatttgtg agtgccggtt    9000
ggtaattatt tttgttaatg tgatttttaaa acctcttatg taaatagtta ctttatctat    9060
tgaagtgtgt tcttgtggtc tatagtttct caaagggaaa ttaaaatgtt gacatcccat    9120
ttacaattga taacttggta tacacaaact ttgtaaattt ggtgatattt atggtcgaaa    9180
gaaggcaata cccattgtat gttccaatat caatatcaat acgataactt gataatacta    9240
acatatgatt gtcattgttt ttccagtatc aatatacatt aagctactac aaaattagta    9300
taaatcacta tattataaat ctttttcggt tgtaacttgt aattcgtggg tttttaaaat    9360
aaaagcatgt gaaaattttc aaataatgtg atggcgcaat tttatttcc gagttccaaa    9420 atattgccgc ttcattaccc taatttgtgg cgccacatgt aaaacaaaag acgattctta    9480
gtggctatca ctgccatcac gcggatcact aatatgaacc gtcgattaaa acagatcgac    9540
ggtttataca tcattttatt gtacacacgg atcgatatct cagccgttag atttaatatg    9600
cgatctgatt gctcaaaaaa tagactctcc gtctttgcct ataaaacaa tttcacatct    9660 ttctcaccca aatctactct taaccgttct tcttcttcta cagacatcaa tttctctcga    9720
ctctagagga tccaagctta tcgatttcga acccctcagg cgaagaacag gtatgatttg    9780
```

```
tttgtaatta gatcaggggt ttaggtcttt ccattacttt ttaatgtttt ttctgttact    9840
gtctccgcga tctgatttta cgacaataga gtttcgggtt ttgtcccatt ccagtttgaa    9900
aataaaggtc cgtcttttaa gtttgctgga tcgataaacc tgtgaagatt gagtctagtc    9960
gatttattgg atgatccatt cttcatcgtt tttttcttgc ttcgaagttc tgtataacca   10020
gatttgtctg tgtgcgattg tcattaccta gccgtgtatc gagaactagg gttttcgagt   10080
caattttgcc ccttttggtt atatctggtt cgataacgat tcatctggat tagggtttta   10140
agtggtgacg tttagtattc caatttcttc aaaatttagt tatggataat gaaaatcccc   10200
aattgactgt tcaatttctt gttaaatgcg cagatcacaa tggcttcgat ctcctcctca   10260
gtcgcgaccg ttagccggac cgcccctgct caggccaaca tggtggctcc gttcaccggc   10320
cttaagtcca acgccgcctt ccccaccacc aagaaggcta acgacttctc cacccttccc   10380
agcaacggtg aaagagttca atgtatgcag gtgtggccgg cctacggcaa caagaagttc   10440
gagacgctgt cgtacctgcc gccgctgtct atggcgccca ccgtgatgat ggcctcgtcg   10500
gccaccgccg tcgctccgtt ccaggggctc aagtccaccg ccagcctccc cgtcgcccgc   10560
cgctcctcca gaagcctcgg caacgtcagc aacggcggaa ggatccggtg catggccggc   10620
gccgaggaga tcgtgctgca gcccatcaag gagatctccg gcaccgtcaa gctgccgggg   10680
tccaagtcgc tttccaaccg gatcctccta ctcgccgccc tgtccgaggg gacaacagtg   10740
gttgataacc tgctgaacag tgaggatgtc cactacatgc tcggggcctt gaggactctt   10800
ggtctctctg tcgaagcgga caaagctgcc aaaagagctg tagttgttgg ctgtggtgga   10860
aagttcccag ttgaggatgc taaagaggaa gtgcagctct tcttggggaa tgctggaatc   10920
gcaatgcggt ccttgacagc agctgttact gctgctggtg gaaatgcaac ttacgtgctt   10980
gatggagtac caagaatgag ggagagaccc attggcgact tggttgtcgg attgaagcag   11040
cttggtgcag atgttgattg tttccttggc actgactgcc cacctgttcg tgtcaatgga   11100
atcggagggc tacctggtgg caaggtcaag ctgtctggct ccatcagcag tcagtacttg   11160
agtgccttgc tgatggctgc tccttttggct cttggggatg tggagattga aatcattgat   11220
aaattaatct ccattccgta cgtcgaaatg acattgagat tgatgagcg ttttggtgtg   11280
aaagcagagc attctgatag ctgggacaga ttctacatta agggaggtca aaaatacaag   11340
tccccctaaaa atgcctatgt tgaaggtgat gcctcaagcg caagctattt cttggctggt   11400
gctgcaatta ctggagggac tgtgactgtg gaaggttgtg gcaccaccag tttgcagggt   11460
gatgtgaagt ttgctgaggt actggagatg atgggagcga aggttacatg gaccgagact   11520
agcgtaactg ttactggccc accgcgggag ccatttggga ggaaacacct caaggcgatt   11580
gatgtcaaca tgaacaagat gcctgatgtc gccatgactc ttgctgtggt tgccctcttt   11640
gccgatggcc cgacagccat cagagacgtg gcttcctgga gagtaaagga gaccgagagg   11700
atggttgcga tccggacgga gctaaccaag ctgggagcat ctgttgagga agggccggac   11760
tactgcatca tcacgccgcc ggagaagctg aacgtgacgg cgatcgacac gtacgacgac   11820
cacaggatgg cgatggcttt ctcccttgcc gcctgtgccg aggtcccgt caccatccgg   11880
gaccctgggt gcacccggaa gaccttcccc gactacttcg atgtgctgag cactttcgtc   11940
aagaattaag ctctagaact agtggatccc ccgatccgcg tttgtgtttt ctgggtttct   12000
cacttaagcg tctgcgtttt acttttgtat tgggttggc gttagtagt ttgcggtagc   12060
gttcttgtta tgtgtaatta cgcttttct tcttgcttca gcagtttcgg ttgaaatata   12120
```

```
aatcgaatca agtttcactt tatcagcgtt gttttaaatt ttggcattaa attggtgaaa   12180
attgcttcaa ttttgtatct aaatagaaga gacaacatga aattcgactt ttgacctcaa   12240
atcttcgaac atttatttcc tgatttcacg atggatgagg ataacgaaag ggcggttcct   12300
atgtccggga agttcccgt agaagacaat gagcaaagct actgaaacgc ggacacgacg    12360
tcgcattggt acggatatga gttaaaccga ctcaattcct ttattaagac ataaaccgat   12420
tttggttaaa gtgtaacagt gagctgatat aaaaccgaaa caaaccggta caagtttgat   12480
tgagcaactt gatgacaaac ttcagaattt tggttattga atgaaaatca tagtctaatc   12540
gtaaaaaatg tacagaagaa aagctagagc agaacaaaga ttctatattc tggttccaat   12600
ttatcatcgc tttaacgtcc ctcagatttg atcgggaaac caaaacgtcg tgagacagtt   12660
tggttaacta taacggtcct aaggtagcga tcgaggcatt acggcattac ggcactcgcg   12720
agggtccgaa ttcgagcatg gagccattta caattgaata tatcctgccg ccgctgccgc   12780
tttgcacccg gtggagcttg catgttggtt tctacgcaga actgagccgg ttaggcagat   12840
aatttccatt gagaactgag ccatgtgcac cttcccccca acacggtgag cgacgggca    12900 acggagtgat ccacatggga cttttaaaca tcatccgtcg gatggcgttg cgagagaagc   12960
agtcgatccg tgagatcagc cgacgcaccg ggcaggcgcg caacacgatc gcaaagtatt   13020
tgaacgcagg tacaatcgag ccgacgttca cggtaccgga acgaccaagc aagctagctt   13080
agtaaagccc tcgctagatt ttaatgcgga tgttgcgatt acttcgccaa ctattgcgat   13140
aacaagaaaa agccagcctt tcatgatata tctcccaatt tgtgtagggc ttattatgca   13200
cgcttaaaaa taataaaagc agacttgacc tgatagtttg gctgtgagca attatgtgct   13260
tagtgcatct aacgcttgag ttaagccgcg ccgcgaagcg gcgtcggctt gaacgaattg   13320
ttagacatta tttgccgact accttggtga tctcgccttt cacgtagtgg acaaattctt   13380
ccaactgatc tgcgcgcgag gccaagcgat cttcttcttg tccaagataa gcctgtctag   13440
cttcaagtat gacgggctga tactgggccg gcaggcgctc cattgcccag tcggcagcga   13500
catccttcgg cgcgattttg ccggttactg cgctgtacca aatgcgggac aacgtaagca   13560
ctacatttcg ctcatcgcca gcccagtcgg cggcgagtt ccatagcgtt aaggtttcat    13620
ttagcgcctc aaatagatcc tgttcaggaa ccggatcaaa gagttcctcc gccgctggac   13680
ctaccaaggc aacgctatgt tctcttgctt ttgtcagcaa gatagccaga tcaatgtcga   13740
tcgtggctgg ctcgaagata cctgcaagaa                                    13770
```

<210> SEQ ID NO 26
<211> LENGTH: 5
<212> TYPE: PRT
<213> ORGANISM: Arabidopsis thaliana

<400> SEQUENCE: 26

Tyr Tyr His Asp Leu
1               5

<210> SEQ ID NO 27
<211> LENGTH: 5
<212> TYPE: PRT
<213> ORGANISM: Arabidopsis thaliana

<400> SEQUENCE: 27

Leu Lys Leu Glu Ile
1               5